United States Patent
Nirogi et al.

(10) Patent No.: US 9,790,211 B2
(45) Date of Patent: Oct. 17, 2017

(54) 5-AMINO-QUINOLINE-8-CARBOXAMIDE DERIVATIVES AS 5-HT4 RECEPTOR AGONISTS

(71) Applicant: SUVEN LIFE SCIENCES LIMITED, Andhra Pradesh (IN)

(72) Inventors: Ramakrishna Nirogi, Andhra Pradesh (IN); Anil Karbhari Shinde, Andhra Pradesh (IN); Venkateswarlu Jasti, Andhra Pradesh (IN)

(73) Assignee: Suven Life Sciences Limited, Hyderabad (IN)

( * ) Notice: Subject to any disclaimer, the term of this patent is extended or adjusted under 35 U.S.C. 154(b) by 0 days.

(21) Appl. No.: 14/777,925

(22) PCT Filed: Oct. 18, 2013

(86) PCT No.: PCT/IN2013/000639
§ 371 (c)(1),
(2) Date: Sep. 17, 2015

(87) PCT Pub. No.: WO2014/147636
PCT Pub. Date: Sep. 25, 2014

(65) Prior Publication Data
US 2016/0280694 A1 Sep. 29, 2016

(30) Foreign Application Priority Data
Mar. 20, 2013 (IN) ............ 1199/CHE/2013

(51) Int. Cl.
| | |
|---|---|
| C07D 401/12 | (2006.01) |
| C07D 405/14 | (2006.01) |
| A61K 31/4709 | (2006.01) |
| G01N 33/558 | (2006.01) |
| G01N 33/574 | (2006.01) |

(52) U.S. Cl.
CPC ......... *C07D 405/14* (2013.01); *C07D 401/12* (2013.01); *G01N 33/558* (2013.01); *G01N 33/57426* (2013.01); *G01N 2333/82* (2013.01); *G01N 2800/52* (2013.01)

(58) Field of Classification Search
None
See application file for complete search history.

(56) References Cited

U.S. PATENT DOCUMENTS

| | | |
|---|---|---|
| 2008/0207690 A1 | 8/2008 | Noguchi et al. |
| 2008/0269211 A1 | 10/2008 | Ishibashi et al. |

FOREIGN PATENT DOCUMENTS

| | | |
|---|---|---|
| WO | 94/08994 | 4/1994 |
| WO | 94/10174 | 5/1994 |
| WO | 2005/003122 A1 | 1/2005 |
| WO | 2005/049608 A1 | 6/2005 |
| WO | 2005/061483 A2 | 7/2005 |
| WO | 2005/092882 A1 | 10/2005 |
| WO | 2006/090224 A1 | 8/2006 |
| WO | 2007/068739 A1 | 6/2007 |
| WO | 2011/099305 A1 | 8/2011 |
| WO | 2011/101774 A1 | 8/2011 |

OTHER PUBLICATIONS

Claeysen et al. ACS Chem. Neurosci. 2015, 6, 940-943.*
Leiser et al. ACS Chem. Neurosci. 2015, 6, 970-986.*
"Study of PRX-03140 Monotherapy in Subjects With Alzheimer's Disease" downloaded at ClinicalTrials.gov Identifier: NCT00693004 on Feb. 25, 2017.*
Bockaert, J., et al. 5-HT$_4$ Receptors. Current Drug Targets—CNS & Neurological Disorder, 2004, 3, p. 39-51.
Langlois, Michel, et al. 5-Ht$_4$ Receptor Ligands: Applications and New Prospects. Journal of Medicinal Chemistry, vol. 46, No. 3, Jan. 30, 2003, p. 319-344.
Johnson, David E, et al. The 5-Hydroxytryptamine$_4$ Receptor Agonists Prucalopride and PRX-03140 Increase Acetylcholine and Histamine Levels in the Rat Prefrontal Cortex and the Power of Stimulated Hippocampal θ Oscillations. The Journal of Pharmacology and Experimental Therapeutics (JPET), vol. 341, No. 3, p. 681-691, 2012.
Lucas, Guillaume, et al. Serotonin$_4$ (5-HT$_4$) Receptor Agonists are Putative Antidepressant with a Rapid Onset of Action. Neuron, 55, p. 712-725, Sep. 6, 2007.
Ahmad, Ishtiyaque, et al. 5-HT$_4$ Receptor Agonists for the Treatment of Alzheimer's Disease. Neuroscience & Medicine, 2011, 2, p. 87-92.
Asai, Hirohide, et al. Increased gastric motility during 5-HT$_4$ agonist therapy reduces response fluctuations in Parkinson's disease. Parkinsonism and Related Disorders 11 (2005), p. 499-502.
Epix Pharmaceuticals, Inc. ClinicalTrials.gov identifier NCT00384423, Jan. 2008.

* cited by examiner

*Primary Examiner* — Emily Bernhardt
(74) *Attorney, Agent, or Firm* — Ladas & Parry LLP

(57) ABSTRACT

The present invention relates to novel quinoline compounds of formula (I), and their pharmaceutically acceptable salts and process for their preparation. The compounds of formula (I) are useful in the treatment of various disorders that are related to 5-HT$_4$ receptor agonists.

20 Claims, 5 Drawing Sheets

5-AMINO-QUINOLINE-8-CARBOXAMIDE DERIVATIVES AS 5-HT4 RECEPTOR AGONISTS

CROSS-REFERENCE TO RELATED APPLICATION

Figure 1:
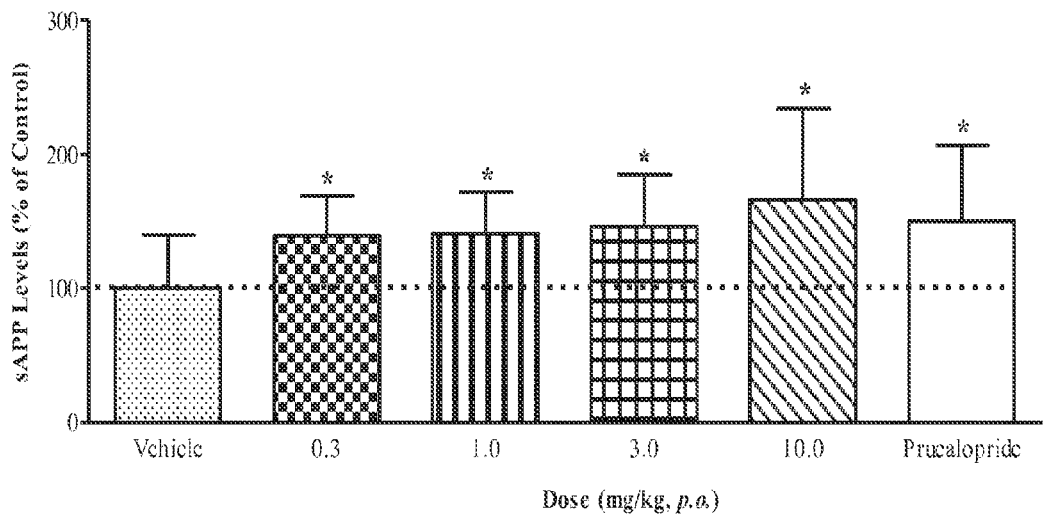

This U.S. application claims priority under 35 U.S.C. 371 to, and is a U.S. National Phase application of, the International Patent Application No. PCT/IN2013/000639, filed 18 Oct. 2013 which claims priority from India Application No. 1199/CHE/2013 filed on 20 Mar. 2013, the disclosures of which are incorporated in their entirety by reference herein.

FIELD OF INVENTION

The present invention relates to novel quinoline compounds of formula (I) and their pharmaceutically acceptable salts, for treatment of various disorders that are related to 5-HT$_4$ receptor agonists.

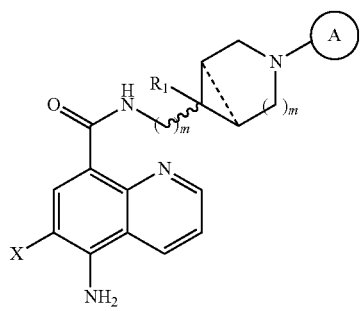

(I)

BACKGROUND OF THE INVENTION

5-HT$_4$ receptor (5-HT$_4$R), belonging to serotonin (5-HT) receptor superfamily is positively coupled to adenylate cyclase thereby increasing the cAMP production. 5-HT$_4$Rs are widely expressed throughout the body, but in all species studied so far the highest density of 5-HT$_4$R is observed in the brain regions associated with learning like cortex and hippocampus (Lezoualc'h, F. et. al. The Serotonin Receptors: From Molecular Pharmacology to Human Therapeutics, The Humana Press, Chapter 15, 2006, 459-479). Brain microdialysis has shown increased release of acetylcholine in the rat frontal cortex and hippocampus following intracerebroventricular injection of 5-HT$_4$R agonists (Journal of Pharmacology and Experimental Therapeutics, 2001, 296 (3), 676-682). Behavioral studies in animal models of learning and memory also support the role of 5-HT$_4$R in cognition.

Interestingly, 5-HT$_4$R also regulates the production of the neurotoxic amyloid β-peptide (Aβ), which is one of the major pathogenetic pathways in Alzheimer's disease (Experimental Neurology, 2007, 203(1), 274-278). Indeed, 5-HT$_4$R agonists can stimulate the non-amyloidogenic pathway leading to the release of the soluble form of the amyloid precursor protein (sAPPα), which in contrast to Aβ, has putative neurotrophic and neuroprotective properties (Journal biological chemistry, 2001, 276(48), 44881-44888). 5-HT$_4$ receptors are, therefore, an exciting potential target for the treatment of Alzheimer's disease symptomatology and pathology (Experimental Neurology, 2007, 205(2), 325-329). Besides this neurodegenerative disorder, 5-HT$_4$R has been described as having mood modulating properties, and these features might be exploited for the treatment of depression (Neuron, 2007, 55(5), 712-725). Thus, 5-HT$_4$R agonists are found to have potential for the treatment of dementia related disorders such as alzheimer's disease, schizpherenia, attention deficit hyperactivity disorder, huntington's disease, parkinson's disease and several other psychiatric disorders (Behavioral brain research, 1996, 73(1-2), 249-52; Schizophrenia Bulletin, 2007, 33 (5), 1100-1119 and Neuroscience & Medicine, 2011, 2, 87-92) and pain (Neuroscience, 2011, 174, 224-233).

5-HT$_4$R agonists also have utility in the treatment of gastrointestinal disorders, especially those associated with reduced esophageal, gastric motility disorders, dyspepsia condition, functional dyspepsia, conditions associated with constipation and irritable bowel syndrome (IBS) and esophagitis (Expert Opinion on Investigational Drugs, 2010, 19(6), 765-775).

Patent publications WO9410174, WO9408994, WO2005049608, WO2006090224, WO2011099305, WO2011101774, US20080207690 and US20080269211 disclosed some 5-HT$_4$ receptor compounds. While several 5-HT$_4$ receptor agonistspartial agonists have been disclosed in the literature, no compound, either agonist or partial agonist targeting 5-HT$_4$ receptor is launched in the market until now for treatments of dementia related disorders. Thereofore, there is need and scope to discover new 5-HT$_4$ receptor agonistspartial agonists with novel chemical structures for treatment of dementia related disorders.

Our quest for finding novel and potent ligands as 5-HT$_4$ agonistspartial agonists had resulted in the discovery of quinoline compounds of the formula (I) which are demonstrating very high affinity and agonist activity towards 5-HT$_4$R with other druggable properties like adequate brain penetration, good oral bioavailability, activity in animal models of cognition, ability to increase cortical sAPPα levels in mice brain significantly and decreasing the levels of Aβ$_{1-40}$ and Aβ$_{1-42}$ levels in the rat brain. Therefore, it is an object of this invention to provide compounds, which are useful as therapeutic agents in the treatment of disorders that are affected by the 5-HT$_4$ receptor agonists.

SUMMARY OF THE INVENTION

The present invention relates to novel 5-HT$_4$ receptor agonists of formula (I),

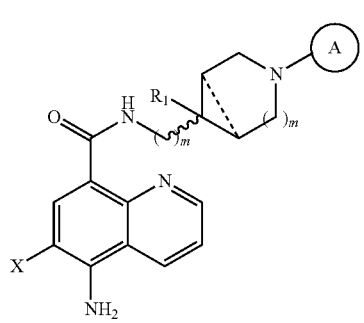

(I)

or a pharmaceutically acceptable salt thereof,
wherein,
"X" is hydrogen or halogen;

" ⁓⁓⁓ " is a bond representing racemic mixture, R-enantiomer, S-enantiomer, exo isomer, endo isomer or achiral;

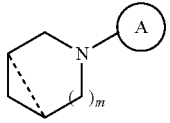

is

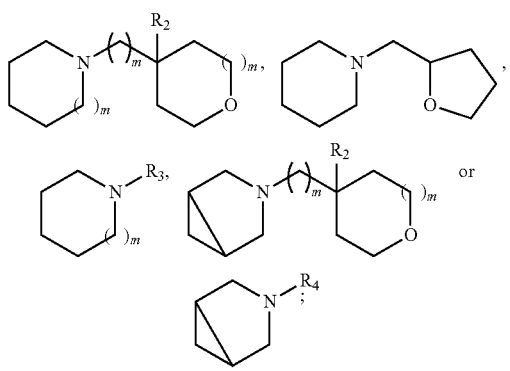

R₁ is hydrogen, hydroxy or halogen;
R₂ is hydrogen, hydroxy or halogen;
R₃ is

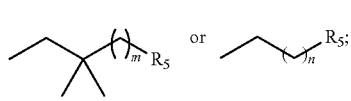

R₄ is alkyl, cycloalkyl, cycloalkylalkyl,

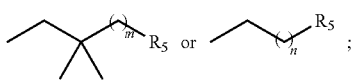

R₅ is halogen, hydroxy, alkoxy,

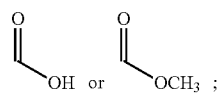

"m" is an integer ranging from 0 to 1, both inclusive;
"n" is an integer ranging from 0 to 3, both inclusive.

The compounds of formula (I) may involve below mentioned embodiments. It is to be understood that the embodiments below are illustrative of the present invention and are not intended to limit the claims to the specific embodiment's exemplified.

According to one embodiment, there is provided a compound of the formula (Ia):

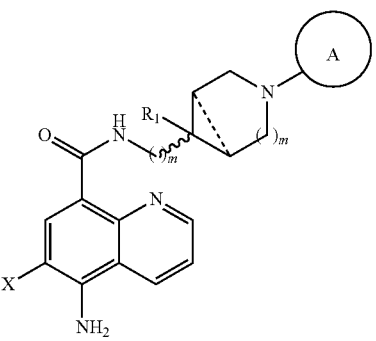

or a pharmaceutically acceptable salt thereof,
wherein,
"X" is halogen;
" ⁓⁓⁓ " a bond represents racemic mixture, R-enantiomer, S-enantiomer, exo isomer, endo isomer or achiral;

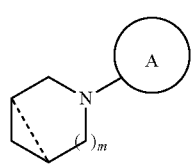

is

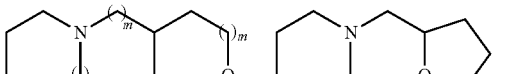
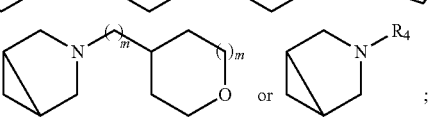

R₁ is hydrogen, hydroxy or halogen;
R₄ is alkyl, cycloalkyl or cycloalkylalkyl;
"m" is an integer ranging from 0 to 1, both inclusive.

According to one embodiment, there is provided a compound of the formula (Ib-1):

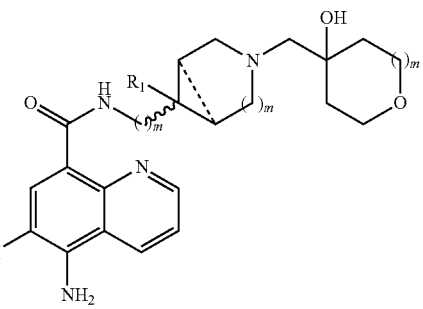

or a pharmaceutically acceptable salt thereof,
wherein,
"X" is halogen;
"⁓" is a bond represents racemic mixture, R-enantiomer, S-enantiomer, exo isomer, endo isomer or achiral;
$R_1$ is hydrogen, hydroxy or halogen;
"m" is an integer ranging from 0 to 1, both inclusive.

According to one embodiment, there is provided a compound of the formula (Ib-2):

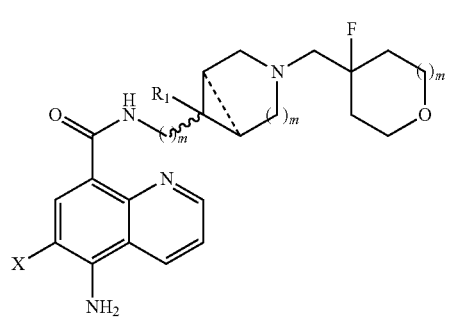

(Ib-2)

or a pharmaceutically acceptable salt thereof,
wherein,
"X" is halogen;
"⁓" is a bond represents racemic mixture, R-enantiomer, S-enantiomer, exo isomer, endo isomer or achiral;
$R_1$ is hydrogen, hydroxy or halogen;
"m" is an integer ranging from 0 to 1, both inclusive.

According to one embodiment, there is provided a compound of the formula (Ic-1):

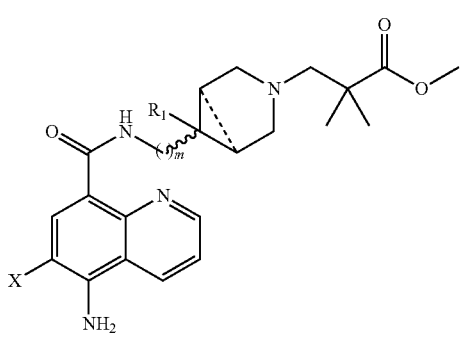

(Ic-1)

or a pharmaceutically acceptable salt thereof,
wherein,
"X" is halogen;
"⁓" is a bond represents racemic mixture, R-enantiomer, S-enantiomer, exo isomer, endo isomer or achiral;
$R_1$ is hydrogen, hydroxy or halogen;
"m" is an integer ranging from 0 to 1, both inclusive.

According to one embodiment, there is provided a compound of the formula (Ic-2):

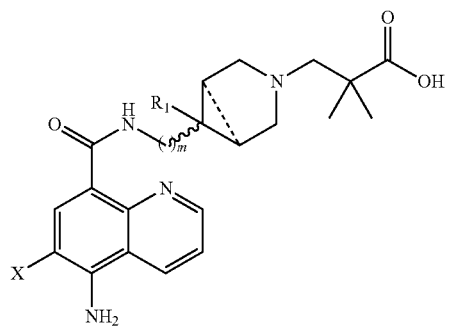

(Ic-2)

or a pharmaceutically acceptable salt thereof,
wherein,
"X" is halogen;
"⁓" is a bond represents racemic mixture, R-enantiomer, S-enantiomer, exo isomer, endo isomer or achiral;
$R_1$ is hydrogen, hydroxy or halogen;
"m" is an integer ranging from 0 to 1, both inclusive.

According to one embodiment, there is provided a compound of the formula (Ic-3):

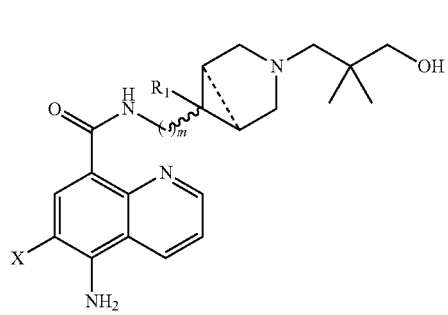

(Ic-3)

or a pharmaceutically acceptable salt thereof,
wherein,
"X" is halogen;
"⁓" is a bond represents racemic mixture, R-enantiomer, S-enantiomer, exo isomer, endo isomer or achiral;
$R_1$ is hydrogen, hydroxy or halogen;
"m" is an integer ranging from 0 to 1, both inclusive.

According to one embodiment, there is provided a compound of the formula (Ic-4):

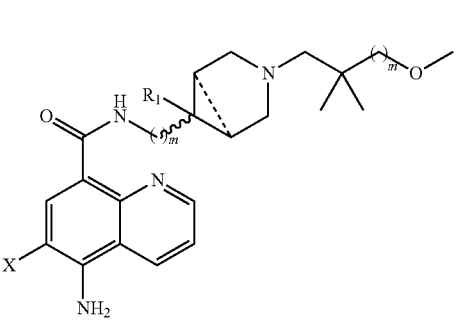

(Ic-4)

or a pharmaceutically acceptable salt thereof,
wherein,
"X" is halogen;
"⁓" is a bond represents racemic mixture, R-enantiomer, S-enantiomer, exo isomer, endo isomer or achiral;
$R_1$ is hydrogen, hydroxy or halogen;
"m" is an integer-ranging from G to 1, both inclusive.

According to one embodiment, there is provided a compound of the formula (Id-1):

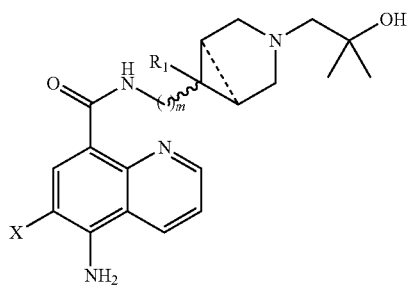

(Id-1)

or a pharmaceutically acceptable salt thereof,
wherein,
"X" is halogen;
"⁓" is a bond represents racemic mixture, R-enantiomer, S-enantiomer, exo isomer, endo isomer or achiral;
$R_1$ is hydrogen, hydroxy or halogen;
"m" is an integer ranging from 0 to 1 both inclusive;

According to one embodiment, there is provided a compound of the formula (Id-2):

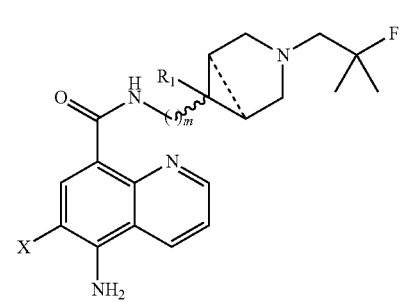

(Id-2)

or a pharmaceutically acceptable salt thereof,
wherein,
"X" is halogen;
"⁓" is a bond represents racemic mixture, R-enantiomer, S-enantiomer, exo isomer, endo isomer or achiral;
$R_1$ is hydrogen, hydroxy or halogen;
"m" is an integer ranging from 0 to 1, both inclusive;

According to one embodiment, there is provided a compound of the formula (Ie-1):

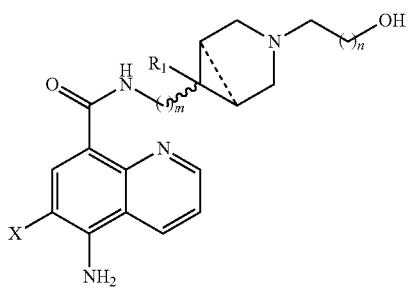

(Ie-1)

or a pharmaceutically acceptable salt thereof,
wherein,
"X" is halogen;
"⁓" is a bond represents racemic mixture, R-enantiomer, S-enantiomer, exo isomer, endo isomer or achiral;
$R_1$ is hydrogen, hydroxy or halogen;
"m" is an integer ranging from 0 to 1, both inclusive;
"n" is an integer ranging from 0 to 3, both inclusive;

According to one embodiment, there is provided a compound of the formula (Ie-2):

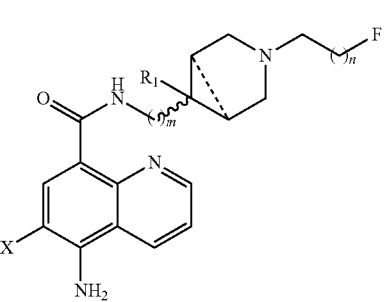

(Ie-2)

or a pharmaceutically acceptable salt thereof,
wherein,
"X" is halogen;
"⁓" is a bond represents racemic mixture, R-enantiomer, S-enantiomer, exo isomer, endo isomer or achiral;
$R_1$ is hydrogen, hydroxy or halogen;
"m" is an integer ranging from 0 to 1, both inclusive;
"n" is an integer ranging from 0 to 3, both inclusive;

According to one embodiment, there is provided a compound of the formula (Ie-3):

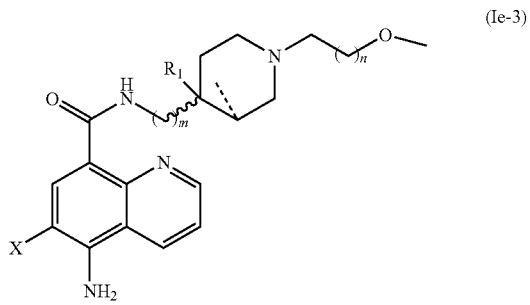

(Ie-3)

or a pharmaceutically acceptable salt thereof,
wherein,
"X" is halogen;
"⌇" is a bond represents racemic mixture, R-enantiomer, S-enantiomer, exo isomer, endo isomer or achiral;
$R_1$ is hydrogen, hydroxy or halogen;
"m" is an integer ranging from 0 to 1, both inclusive;
"n" is an integer ranging from 0 to 3, both inclusive;

The present invention relates to use of a therapeutically effective amount of compound of formula (I), to manufacture a medicament in the treatment of various disorders that are related to 5-HT$_4$ receptor agonists.

Specifically, the compounds of this invention are useful in the treatment of various disorders such as alzheimer's disease, schizpherenia, attention deficit hyperactivity disorder, huntington's disease, parkinson's disease, psychiatric disorders or gastrointestinal disease and symptoms thereof.

In another aspect, the invention relates to pharmaceutical compositions containing a therapeutically effective amount of at least one compound of formula (I), and their pharmaceutically acceptable salts thereof, in admixture with pharmaceutical acceptable excipient.

In still another aspect, the invention relates to methods for using compounds of formula (I).

In yet another aspect, the invention further relates to the process for preparing compounds of formula (I) and their pharmaceutically acceptable salts.

Representative compounds of the present invention include those specified below and their pharmaceutically acceptable salts. The present invention should not be construed to be limited to them.

5-Amino-6-chloro-N-{[1-(tetrahydro-2H-pyran-4-ylmethyl)-4-piperidinyl]methyl}quinoline-8-carboxamide hemifumarate;
5-Amino-6-chloro-N-{[3-(tetrahydro-2H-pyran-4-ylmethyl)-3-azabicyclo[3.1.0]hex-6-yl]methyl} quinoline-8-carboxamide L(+)-tartarate;
5-Amino-6-chloro-N-[1-(tetrahydro-2H-pyran-4-ylmethyl)-4-piperidinyl] quinoline-8-carboxamide;
(R,S) 5-Amino-6-chloro-N-{[1-(tetrahydro-3-furanylmethyl)-4-piperidinyl]methyl}quinoline-8-carboxamide L(+)-tartarate;
(R,S) 5-Amino-6-chloro-N-{[1-(tetrahydro-2-furanylmethyl)-4-piperidinyl]methyl}quinoline-8-carboxamide;
5-Amino-6-chloro-N-{[1-(tetrahydro-2H -pyran-4-yl)-4-piperidinyl]methyl}quinoline-8-carboxamide L(+)-tartarate;
5-Amino-6-chloro-N-{[3-(tetrahydro-3-furanylmethyl)-3-azabicyclo[3.1.0]hex-6-yl]methyl}quinoline-8-carboxamide;
5-Amino-6-chloro-N-{[3-isobutyl-3-azabicyclo[3.1.0]hex-6-yl]methyl}quinoline-8-carboxamide L(+)-tartarate;
5-Amino-6-chloro-N-{[3-cyclopropylmethyl-3-azabicyclo[3.1.0]hex-6-yl]methyl}quinoline-8-carboxamide L(+)-tartarate;
5-Amino-6-chloro-N-{[3-isopropyl-azabicyclo[3.1.0]hex-6-yl]methyl}quinoline-8-carboxamide L(+)-tartarate;
5-Amino-6-fluoro-N-{[1-tetrahydro-2H-pyran-4-ylmethyl)-4-piperidinyl]methyl}quinoline-8-carboxamide L(+)-tartarate;
5-Amino-6-chloro-N-{[1-(tetrahydro-2H-pyran-4-ylmethyl)-3-pyrrolidinyl]methyl}quinoline-8-carboxamide L(+)-tartarate;
5-Amino-6-chloro-N-{[1-(tetrahydro-2H-pyran-4-ylmethyl)-4-piperidinyl]methyl}quinoline-8-carboxamide L(+)-tartarate;
(Exo) 5-Amino-6-chloro-N-{[3-(tetrahydro-2H-pyran-4-ylmethyl)-3-azabicyclo[3.1.0]hex-6-yl]methyl}quinoline-8-carboxamide;
5-Amino-6-chloro-N-{[1-tetrahydro-2H-pyran-4-ylmethyl)-3-azabicyclo[3.1.0]hex-6-yl]methyl}quinoline-8-carboxamide (exo/endo mixture);
5-Amino-6-bromo-N-{[1-(tetrahydro-2H-pyran-4-ylmethyl)-4-piperidinyl]methyl}quinoline-8-carboxamide L(+)-tartarate;
5-Amino-6-bromo-N-{[3-(tetrahydro-2H-pyran-4-yl methyl)-3-azabicyclo[3.1.0]hex-6-yl]methyl}quinoline-8-carboxamide L(+)-tartarate;
5-Amino-6-chloro-N-{[1-(tetrahydro-2-furanylmethyl)-4-piperidinyl]methyl}quinoline-8-carboxamide L(+)-tartarate;
5-Amino-6-fluoro-N-{[3-(tetrahydro-2H-pyran-4-yl methyl)-3-azabicyclo[3.1.0]hex-6-yl]methyl}quinoline-8-carboxamide L(+)-tartarate;
5-Amino-6-chloro-N-{[4-fluoro-1-(tetrahydro-2H-pyran-4-ylmethyl)-4-piperidinyl]methyl}quinoline-8-carboxamide L(+)-tartarate;
(R,S) 5-Amino-6-chloro-N-{[4-fluoro-1-(tetrahydro-3-furanylmethyl)-4-piperidinyl]methyl}quinoline-8-carboxamide L(+)-tartarate;
5-Amino-6-chloro-N-{[4-hydroxy-1-(tetrahydro-2H-pyran-4-yl methyl)-4-piperidinyl]methyl}quinoline-8-carboxamide L(+)-tartarate;
5-Amino-6-chloro-N-{[1-(4-hydroxytetrahydro-2H-pyran-4-ylmethyl)-4-piperidinyl]methyl}quinoline-8-carboxamide L(+)-tartarate;
5-Amino-6-chloro-N-[1-(4-hydroxytetrahydro-2H-pyran-4-ylmethyl)-4-piperidinyl] quinoline-8-carboxamide;
5-Amino-6-chloro-N-{[3-(4-hydroxytetrahydro-2H-pyran-4-ylmethyl)-3-azabicyclo[3.1.0]hex-6-yl]methyl}quinoline-8-carboxamide L(+)-tartarate;
5-Amino-6-chloro-N-{[1-(4-hydroxytetrahydro-2H-pyran-4-ylmethyl)-4-piperidinyl]methyl}quinoline-S-carboxamide;
5-Amino-6-chloro-N-{[4-fluoro-1-(4-hydroxytetrahydro-2H-pyran-4-ylmethyl)-4-piperidinyl]methyl}quinoline-8-carboxamide L(+)-tartarate;
5-Amino-6-fluoro-N-{[1-(4-hydroxytetrahydro-2H-pyran-4-ylmethyl)-4-piperidinyl]methyl}quinoline-8-carboxamide L(+)-tartarate;
5-Amino-6-chloro-N-{[4-hydroxy-1-(4-hydroxy tetrahydro-2H-pyran-4-yl methyl)-4-piperidinyl]methyl}quinoline-8-carboxamide L(+)-tartarate;
5-Amino-6-chloro-N-{[1-(4-fluorotetrahydro-2-pyran-4-yl-methyl)-4-piperidinyl]methyl}quinoline-8-carboxamide L(+)-tartarate;
5-Amino-6-chloro-N-{[1-(2-methoxy carbonyl-2-methyl propan-1-yl)-4-piperidinyl]methyl}quinoline-8-carboxamide;
5-Amino-6-chloro-N-{[1-(2,2-dimethyl proponic acid-3-yl)-4-piperidinyl]methyl}quinoline-8-carboxamide L(+)-tartarate;
5-Amino-6-chloro-N-{[1-(3-hydroxy-2,2-dimethyl propyl)-4-piperidinyl]methyl}quinoline-8-carboxamide L(+)-tartarate;
5-Amino-6-chloro-N-{[3-(3-hydroxy-2,2-dimethyl propyl)-3-azabicyclo[3.1.0]hex-6-yl]methyl}quinoline-8-carboxamide L(+)-tartarate;
5-Amino-6-chloro-N-{[1-(2-hydroxy-2-methyl propyl)-4-piperidinyl]methyl}quinoline-8-carboxamide L(+)-tartarate;
5-Amino-6-chloro-N-{[4-fluoro-1-(2-hydroxy-2-methyl propyl)-4-piperidinyl]methyl}quinoline-8-carboxamide;

5-Amino-6-chloro-N-{[4-fluoro-1-(2-hydroxy-2-methyl propyl)-4-piperidinyl]methyl}quinoline-8-carboxamide L(+)-tartarate;
5-Amino-6-chloro-N-{[4-fluoro-1-(2-hydroxy-2-methyl propyl)-4-piperidinyl]methyl}quinoline-8-carboxamide hydrochloride;
5-Amino-6-chloro-N-{[4-fluoro-1-(2-hydroxy-2-methyl propyl)-4-piperidinyl]methyl}quinoline-8-carboxamide fumarate;
5-Amino-6-chloro-N-{[3-(2-hydroxy-2-methyl propyl)-3-azabicyclo[3.1.0]hex-6-yl]methyl}quinoline-8-carboxamide L(+)-tartarate;
5-Amino-6-fluoro-N-{[1-(2-hydroxy-2-methyl propyl)-4-piperidinyl]methyl}quinoline-8-carboxamide L(+)-tartarate;
5-Amino-6-fluoro-N-{[4-fluoro-1-(2-hydroxy-2-methyl propyl)-4-piperidinyl]methyl}quinoline-8-carboxamide;
5-Amino-6-fluoro-N-{[4-fluoro-1-(2-hydroxy-2-methyl propyl)-4-piperidinyl]methyl}quinoline-8-carboxamide L(+)-tartarate;
5-Amino-6-bromo-N-{[1-(2-hydroxy-2-methyl propyl)-4-piperidinyl]methyl}quinoline-8-carboxamide L(+)-tartarate;
5-Amino-6-bromo-N-{[4-fluoro-1-(2-hydroxy-2-methyl propyl)-4-piperidinyl]methyl}quinoline-8-carboxamide L(+)-tartarate;
5-Amino-6-chloro-N-{[1-(2-fluoro-2-methyl propyl)-4-piperidinyl]methyl}quinoline-8-carboxamide;
5-Amino-6-chloro-N-{[3-(2-fluoro-2-methyl propyl)-3-azabicyclo[3.1.0]hex-6-yl]methyl}quinoline-8-carboxamide;
5-Amino-6-chloro-N-{[4-fluoro-1-(2-fluoro-2-methyl propyl)-4-piperidinyl]methyl}quinoline-8-carboxamide;
5-Amino-6-chloro-N-{[1-(2-hydroxy ethyl)-4-piperidinyl]methy)}quinoline-8-carboxamide;
5-Amino-6-chloro-N-{[3-(2-hydroxy ethyl)-3-azabicyclo[3.1.0]hex-6-yl]methyl}quinoline-8-carboxamide;
5-Amino-6-chloro-N-{[3-(3-hydroxy propyl)-3-azabicyclo[3.1.0]hex-6-yl]methyl}quinoline-8-carboxamide;
5-Amino-6-chloro-N-{[1-(2-fluoro ethyl)-4-piperidinyl]methyl}quinoline-8-carboxamide;
5-Amino-6-chloro-N-{[3-(2-hydroxy ethyl)-3-azabicyclo[3.1.0]hex-6-yl]methyl}quinoline-8-carboxamide;
5-Amino-6-chloro-N-{[3-(3-methoxy propyl)-3-azabicyclo[3.1.0]hex-6-yl]methyl}quinoline-8-carboxamide L(+)-tartarate;
5-Amino-6-chloro-N-{[1-(3-methoxy-2,2-dimethyl propyl)-4-piperidinyl]methyl}quinoline-8-carboxamide L(+)-tartarate;
5-Amino-6-chloro-N-{[1-(2-methoxy-2-methyl propyl)-4-piperidinyl]methyl}quinoline-8-carboxamide;
5-Amino-6-fluoro-N-{[1-(2-methoxy-2-methyl propyl)-4-piperidinyl]methyl}quinoline-8-carboxamide;
5-Amino-6-bromo-N-{[1-(2-methoxy-2-methyl propyl)-4-piperidinyl]methyl}quinoline-8-carboxamide;
5-Amino-6-chloro-N-{[4-fluoro-1-(3-methoxy-2,2-dimethyl propyl)-4-piperidinyl]methyl}quinoline-8-carboxamide;
5-Amino-6-chloro-N-{[4-fluoro-1-(2-methoxy-2-methyl propyl)-4-piperidinyl]methyl}quinoline-8-carboxamide;
5-Amino-6-fluoro-N-{[4-fluoro-1-(2-methoxy-2-methyl propyl)-4-piperidinyl]methyl}quinoline-8-carboxamide; and
5-Amino-6-bromo-N-{[4-fluoro-1-(2-methoxy-2-methyl propyl)-4-piperidinyl]methyl}quinoline-8-carboxamide.

DETAILED DESCRIPTION OF THE INVENTION

Unless otherwise stated, the following terms used in the specification and claims have the meanings given below:

The term "alkyl" means straight or branched hydrocarbon chain radical consisting solely of carbon and hydrogen atoms, containing no unsaturation, having from one to eight carbon atoms, and which is attached to the rest of the molecule by a single bond. Exemplary "alkyl" groups include methyl, ethyl, n-propyl, iso-propyl and the like.

The term "Cycloalkyl" means non-aromatic mono or multi cyclic ring systems of 3 to 12 carbon atoms. Exemplary "Cycloalkyl" groups include cyclopropyl, cyclobutyl, cyclopentyl and the like.

The term "Cycloalkylalky" means cycloalkyl group directly attached to alkyl group. Exemplary "Cycloalkylalkyl" groups include cyclopropylmethyl, cyclobutylethyl, cyclopentylethyl and the like.

The term "agonist" means full agonist or partial agonist.

The phrase "therapeutically effective amount" is defined as an amount of a compound of the present invention that (i) treats the particular disease, condition or disorder (ii) eliminates one or more symptoms of the particular disease, condition or disorder (iii) delays the onset of one or more symptoms of the particular disease, condition or disorder described herein.

Commercial reagents were utilized without further purification. RT refers to 25-40° C. Unless otherwise stated, all mass spectra were obtained using ESI conditions. $^1$H-NMR spectra were recorded at 400 MHz on a Bruker instrument. Deuterated chloroform, methanol or dimethylsulfoxide was used as solvent. TMS was used as internal reference standard. Chemical shift values are expressed in parts per million (δ) values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. Chromatography refers to column chromatography performed using 100-200 mesh silica gel and executed under nitrogen pressure (flash chromatography) conditions.

Pharmaceutical Compositions

In order to use the compounds of formula (I) in therapy, they will normally be formulated into a pharmaceutical composition in accordance with standard pharmaceutical practice.

The pharmaceutical compositions of the present invention may be formulated in a conventional manner using one or more pharmaceutically acceptable excipients. The pharmaceutically acceptable excipient is carrier or diluent. Thus, the active compounds of the invention may be formulated for oral dosing. Such pharmaceutical compositions and processes for preparing same are well known in the art (The Science and Practice of Pharmacy, D. B. Troy, 21$^{st}$ Edition. Williams & Wilkins. 2006).

The dose of the active compounds can vary depending on factors such as age and weight of patient, nature and severity of the disease to be treated and such other factors. Therefore, any reference regarding pharmacologically effective amount of the compounds of general formula (I) refers to the aforementioned factors.

Methods of Preparation

The compounds of formula (I) can be prepared by using Schemes I to V as shown below:

Scheme I:

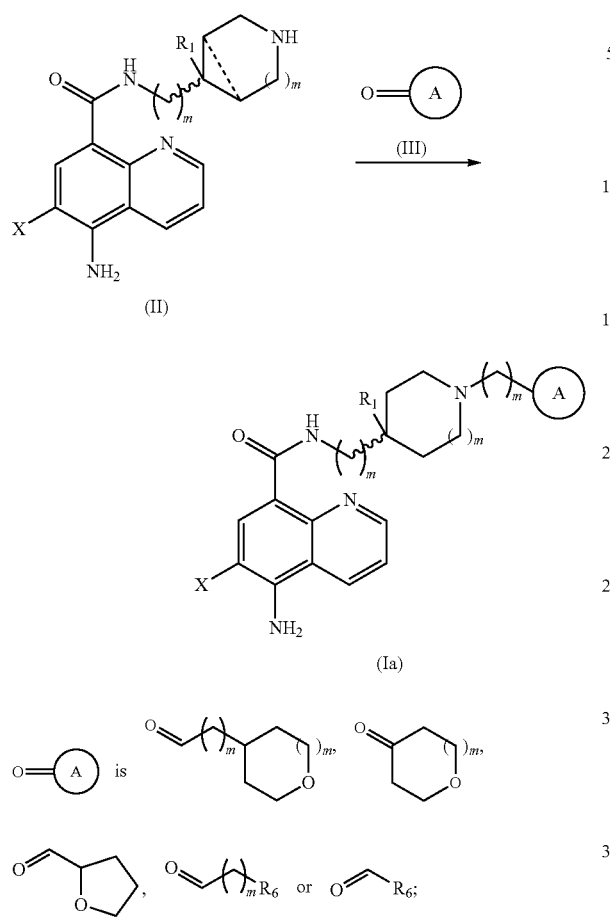

R$_6$ is alkyl, cycloalkyl or cycloalkylalkyl.

In above Scheme I, all remaining symbols are as defined above.

The compound of formula (II) is coupled with compound of formula (III) by reductive amination to form compound of formula (Ia). The reaction may be affected in the presence of a reducing agent such as sodium triacetoxyborohydride, sodium bis(2-methoxyethoxy)aluminumhydride, sodium hydrosulfite, sodium borohydride, sodium cyanoborohydride, sodium dithionite and preferably by using sodium triacetoxyborohydride.

This reaction is preferably carried out in a solvent such as methanol, dichloroethane, dichloromethane, tetrahydrofuran, toluene, diethyl ether and the like or a mixture thereof and preferably by using dichloroethane or dichloromethane. The reaction is carried out at room temperature. The duration of the reaction may range from 10 to 14 hours, preferably for the period of 11 to 13 hours.

The compounds of formula (II) may be prepared by using preparation 2.

The compounds of formula's (II) and (III) may be commercially available or can be prepared by conventional methods or by modification, using known process.

Scheme II:

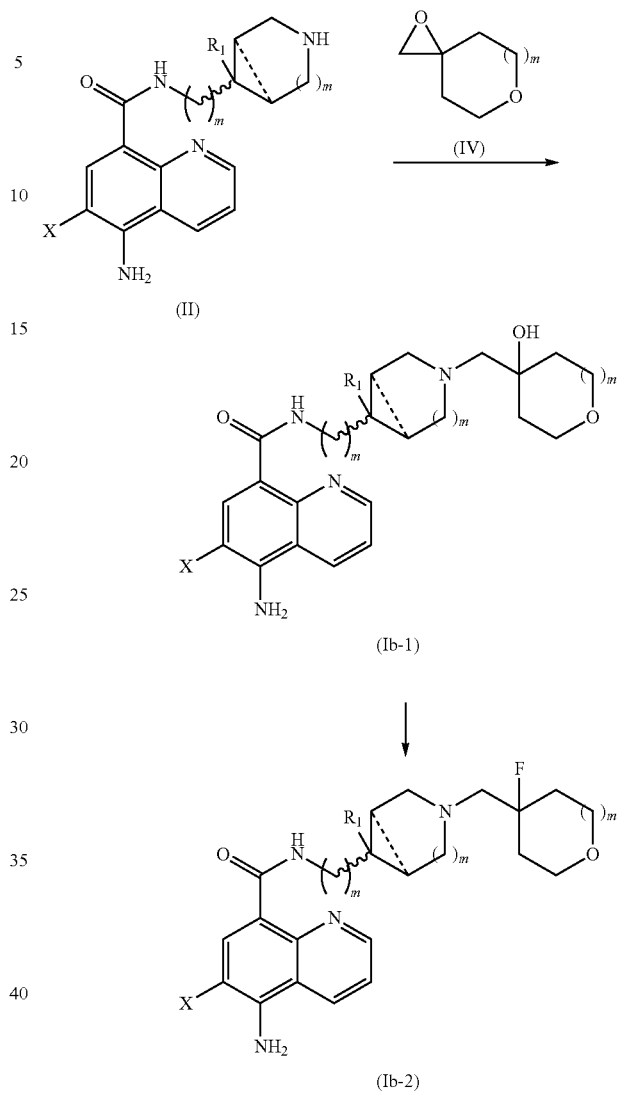

In Scheme II, all symbols are as defined above.

The compounds of formula (Ib-1) and (Ib-2) are prepared according to Scheme II.

The compound of formula (II) is coupled with compound of formula (IV) to form compound of formula (Ib-1). This reaction is carried out in a solvent such as methanol, tetrahydrofuran, toluene, dimethylformamide, dimethyl sulfoxide, diethyl ether and the like or a mixture thereof and preferably by using methanol. The reaction may be affected in the presence of a base such as triethylamine, potassium carbonate, diisopropylethylamine, pyridine and the like or a mixture thereof and preferable by using triethylamine. The reaction temperature may range from 70° C. to 86° C. based on the choice of solvent and preferably at a temperature in the range from 74° C. to 82° C. The duration of the reaction may range from 10 to 14 hours, preferably for the period of 11 to 13 hours.

The compound of formula (Ib-1) is converted to the compound of formula (Ib-2) in presence of diethylaminosulfur trifluoride. This reaction is carried out in a solvent such as methanol, dichloroethane, dichloromethane, tetrahydrofuran, toluene, diethyl ether and the like or a mixture thereof and preferably by using dichloromethane. The reaction is carried out at room temperature. The duration of the reaction may range from 10 to 14 hours, preferably for the period of 11 to 13 hours.

The compounds of formula (II) may be prepared by using preparation 2.

The compounds of formula's (II) and (IV) may be commercially available or can be prepared by conventional methods or by modification, using known process.

In Scheme III, all symbols are as defined above. The compounds of formula (Ic-1), (Ic-2), (Ic-3) and (Ic-4) are prepared according to Scheme III.

The compound of formula (II) is coupled with compound of formula (V) to form compound of formula (Ic-1). This reaction is carried out in a solvent such as methanol, dichloroethane, dichloromethane, tetrahydrofuran, toluene, diethyl ether and the like or a mixture thereof and preferably by using dichloroethane. The reaction may be affected in the presence of a base such as sodium triacetoxyborohydride, sodium bis(2-methoxyethoxy)aluminumhydride, sodium hydrosulfite, sodium borohydride, sodium cyanoborohydride, sodium dithionite and preferably by using sodium triacetoxyborohydride and the like or a mixture thereof and Scheme III:

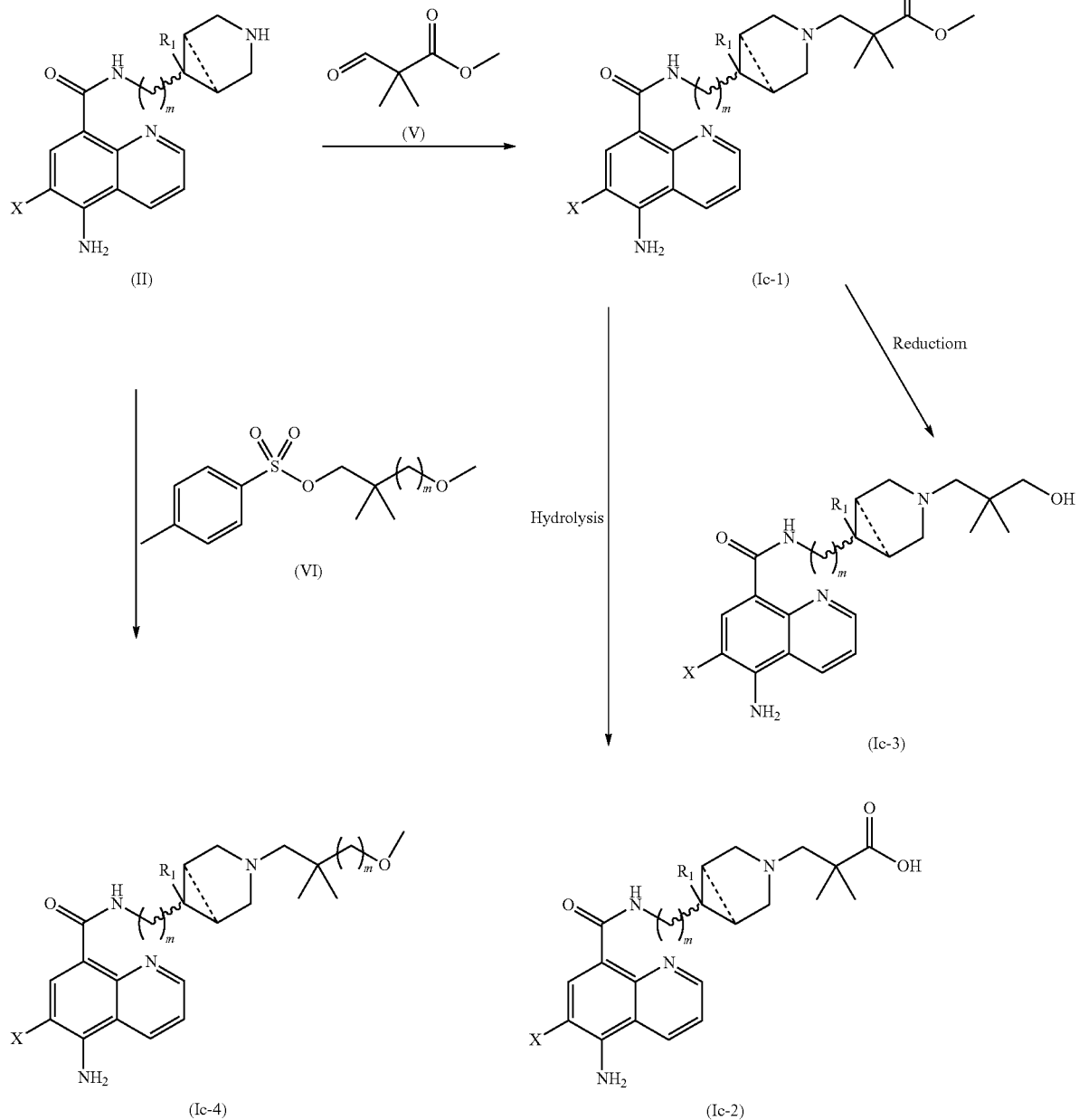

preferable by using sodium triacetoxyborohydride. The reaction is carried out at room temperature. The duration of the reaction may range from 10 to 14 hours, preferably for the period of 11 to 13 hours.

The compound of formula (Ic-1) is hydrolyzed to form compound of formula (Ic-2). This reaction is carried out in a solvent such as methanol, water, dichloroethane, dichloromethane, tetrahydrofuran, toluene, dimethylformamide, dimethyl sulfoxide, diethyl ether and the like or a mixture thereof and preferably by using methanol. The reaction may be affected in the presence of a base such as lithium hydroxide monohydrate, sodium hydroxide, potassium hydroxide, sodium carbonate, potassium carbonate and the like or a mixture thereof and preferable by using lithium hydroxide monohydrate. The reaction is carried out at room temperature. The duration of the reaction may range from 10 to 14 hours, preferably for the period of 11 to 13 hours.

The compound of formula (Ic-1) is reduced to form compound of formula (Ic-3). This reaction is carried out in a solvent such as methanol, tetrahydrofuran, toluene, diethyl ether and the like or a mixture thereof and preferably by using tetrahydrofuran. The reaction may be affected in the presence of a base such as lithium aluminum hydride, lithium borohydride, diisobutylaluminum hydride, sodium borohydride and the like or a mixture thereof and preferable by using lithium hydroxide monohydrate. The reaction is carried out at room temperature. The duration of the reaction may range from 3 to 6 hours, preferably for the period of 4 to 5 hours.

The compound of formula (II) is coupled with compound of formula (VI) in presence of cesium carbonate and potassium iodide to form compound of formula (Ic-4). This reaction is carried out in a solvent such as dimethylformamide, methanol, dichloroethane, dichloromethane, tetrahydrofuran, toluene, diethyl ether and the like or a mixture thereof and preferably by using dimethylformamide. The reaction temperature may range from 110° C. to 130° C. based on the choice of solvent and preferably at a temperature in the range of 115° C. to 125° C. The reaction is carried out at room temperature. The duration of the reaction may range from 23 to 25 hours, preferable for the period of 24 hours.

The compounds of formula (II) and (VI) may be prepared by using preparations 2 and 7.

The compounds of formula's (II), (V) and (VI) may be commercially available or can be prepared by conventional methods or by modification, using known process.

Scheme IV:

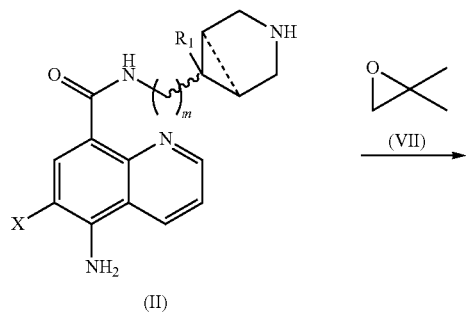

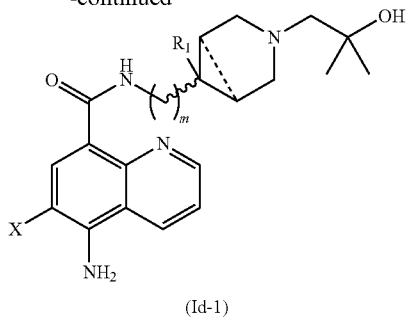

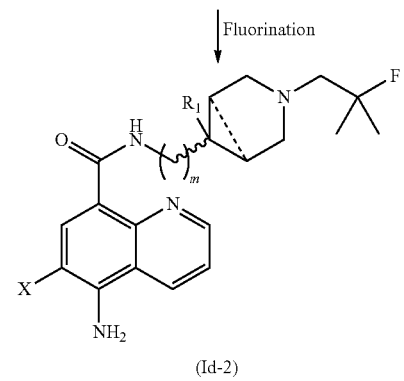

In Scheme IV, all symbols are as defined above.

The compounds of formula (Id-1) and (Id-2) are prepared according to Scheme IV.

The compound of formula (II) is coupled with compound of formula (VII) to form compound of formula (Id-1). This reaction is carried out in a solvent such as methanol, dichloroethane, dichloromethane, tetrahydrofuran, toluene, diethyl ether and the like or a mixture thereof and preferably by using methanol. The reaction may be affected in the presence of a base such as triethylamine, potassium carbonate, diisopropylethylamine, pyridine and the like or a mixture thereof and preferable by using triethylamine. The reaction temperature may range from 65° C. to 85° C. based on the choice of solvent and preferably at a temperature in the range from 70° C. to 80° C. The reaction is carried out at room temperature. The duration of the reaction may range from 10 to 14 hours, preferably for the period of 11 to 13 hours.

The compound of formula (Id-1) is fluorinated to form compound of formula (Id-2) in presence of diethylaminosulfur trifluoride. This reaction is carried out in a solvent such as methanol, dichloroethane, dichloromethane, tetrahydrofuran, toluene, diethyl ether and the like or a mixture thereof and preferably by using dichloromethane. The reaction is carried out at room temperature. The duration of the reaction may range from 10 to 14 hours, preferably for the period of 11 to 13 hours.

The compounds of formula (II) may be prepared by using preparation 2.

The compounds of formula's (II) and (VII) may be commercially available or can be prepared by conventional methods or by modification, using known process.

Scheme V:

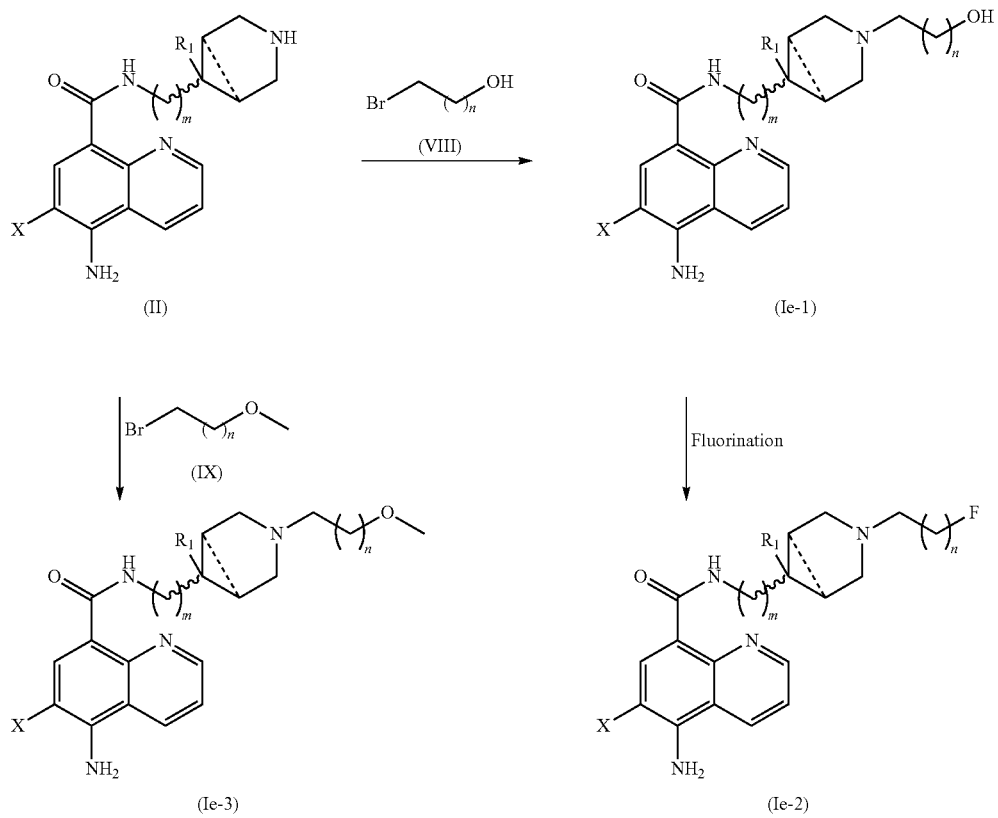

In Scheme V, all symbols are as defined above. The compounds of formula (Ie-1), (Ie-2) and (Ie-3) are prepared according to Scheme V.

The compound of formula (II) is coupled with compound of formula (VIII) to form compound of formula (Ie-1). This reaction is carried out in a solvent such as acetonitrile, methanol, dichloroethane, dichloromethane, tetrahydrofuran, toluene, dimethylformamide, dimethyl sulfoxide, diethyl ether and the like or a mixture thereof and preferably by using acetonitrile. The reaction may be affected in the presence of a base such as potassium bicarbonate, triethylamine, potassium carbonate, diisopropylethylamine, pyridine and the like or a mixture thereof and preferable by using potassium bicarbonate. The reaction temperature may range from 75° C. to 95° C. based on the choice of solvent and preferably at a temperature in the range from 82° C. to 88° C. The duration of the reaction may range from 10 to 14 hours, preferably for the period of 11 to 13 hours.

The compound of formula (Ie-1) is fluorinated to form compound of formula (Ie-2) in presence of diethylaminosulfur trifluoride. This reaction is carried out in a solvent such as methanol, dichloroethane, dichloromethane, tetrahydrofuran, toluene, dimethylformamide, dimethyl sulfoxide, dimethyl ether and the like or a mixture thereof and preferably by using dichloromethane. The reaction is carried out at room temperature. The duration of the reaction may range from 10 to 14 hours, preferably for the period of 11 to 13 hours.

The compound of formula (II) is coupled with compound of formula (IX) to form compound of formula (Ie-3). This reaction is carried out in a solvent such as acetonitrile methanol, dichloroethane, dichloromethane, tetrahydrofuran, toluene, dimethylformamide, dimethyl sulfoxide, dimethyl ether and the like or a mixture thereof and preferably by using acetonitrile. The reaction may be affected in the presence of a base such as potassium bicarbonate, sodium triacetoxyborohydride, triethylamine, potassium carbonate, diisopropylethylamine, pyridine and the like or a mixture thereof and preferable by using potassium carbonate. The reaction temperature may range from 75° C. to 95° C. based on the choice of solvent and preferably at a temperature in the range from 82° C. to 88° C. The duration of the reaction may range from 4 to 8 hours, preferably for the period of 5 to 7 hours.

The compounds of formula (II) may be prepared by using preparation 2.

The compounds of formula's (II). (VIII) and (IX) may be commercially available or can be prepared by conventional methods or by modification, using known process.

If necessary, pharmaceutically acceptable salts for compounds of formula (I) may be prepared conventionally by reaction with the appropriate acid or acid derivative.

Suitable pharmaceutically acceptable salts will be apparent to those skilled in the art and include those described in Journal of Pharmaceutical Science, 1977, 66, 1-19, such as acid addition salts formed with inorganic acids e. g. hydrochloric, hydrobromic, sulfuric, nitric or phosphoric acid and organic acids e.g., succinic, maleic, acetic, fumaric, citric, malic, tartaric, benzoic, p-toluic, p-toluenesulfonic, benzenesulfonic acid, methanesulfonic or naphthalenesulfonic acid. The most preferred salts of compounds of formula (I) are tartarate, fumarate and hydrochloride. Based on the clinical development of the compounds of formula (I), we will select the exact salt form for the compounds of formula (I).

Certain compounds of formula (I) are capable of existing in stereoisomeric forms (e. g. R-enantiomer, S-enantiomer, exo isomer or endo isomers) and the invention extends to each of these stereoisomeric forms and to mixtures thereof including racemates. The different stereoisomeric forms may be separated from one another by the usual methods or any given isomer may be obtained by stereospecific or asymmetric synthesis.

The stereoisomers as a rule are generally obtained as racemates that can be separated into the optically active isomers in a manner known per se. In the case of the compounds of general formula (I) having an asymmetric carbon atom the present invention relates to the D-form, the L-form and D,L-mixtures and in the case of compound of general formula (I) containing a number of asymmetric carbon atoms, the diastereomeric forms and the invention extends to each of these stereo isomeric forms and to mixtures thereof including racemates. Those compounds of general formula (I) which have an asymmetric carbon and as a rule are obtained as racemates can be separated one from the other by the usual methods, or any given isomer may be obtained by stereospecific or asymmetric synthesis. However, it is also possible to employ an optically active compound from the start, a correspondingly optically active enantiomeric or diastereomeric compound then being obtained as the final compound.

The stereoisomers of compounds of general formula (I) may be prepared by one or more ways presented below:
i) One or more of the reagents may be used in their optically active form.
ii) Optically pure catalyst or chiral ligands along with metal catalyst may be employed in the reduction process. The metal catalyst may be Rhodium, Ruthenium, Indium and the like. The chiral ligands may preferably be chiral phosphines.
iii) The mixture of stereoisomers may be resolved by conventional methods such as forming diastereomeric salts with chiral acids or chiral amines or chiral amino alcohols, chiral amino acids. The resulting mixture of diastereomers may then be separated by methods such as fractional crystallization, chromatography and the like, which is followed by an additional step of isolating the optically active product by adopting an appropriate method well known in the art.
iv) The mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like.

Preparations

Preparation 1: Preparation of 6-Chloro-5-nitro quinoline-8-carboxylic acid

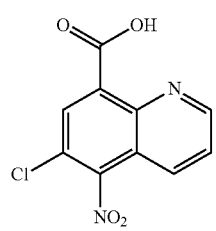 [SMILES: O=C(O)c1cc(Cl)c([N+](=O)[O-])c2cccnc12]

Step (i): Preparation of 6-Chloro-8-methyl quinoline

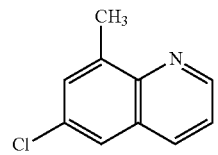

To a stirred solution of 4-chloro-2-methyl aniline (100 grams, 0.706 mole) and glycerol (260 grams, 2.82 mole) in nitrobenzene (200 mL) was added concentrated sulfuric acid (200 mL) drop wise at room temperature (RT). Then reaction mass was slowly heated to 140° C., at which temperature a vigorous reaction was observed. Mass temperature went up to reflux temperature (~200° C.) due to sudden exotherm. The reaction mass was further stirred for 6 hours at 140° C., while monitoring the progress of the reaction by thin layer chromatography (TLC). After completion of reaction, the mass was cooled to RT and stirred over night. Reaction mass was quenched onto chilled water (5 L) and the pH was adjusted to ~9 using 40% aqueous sodium hydroxide solution. Ethyl acetate (3 L) was added to the reaction mass and stirred further for 30 minutes. The resulting solution was filtered through celite bed. Organic layer was separated and the aqueous phase was extracted with ethyl acetate (5×2 L). The combined organic layer (13 L) was washed with water (3 L) and brine solution (3 L). The organic phase was dried over sodium sulfate and concentrated under vacuum to obtain the crude residue, which was further purified by flash chromatography using ethyl acetate: n-hexane (5:95) to afford the title compound.

Yield: 100.8 grams (80%).

$^1$H-NMR ($\delta$ ppm): 2.82 (3H, s), 7.43-7.46 (1H, m), 7.55 (1H, s), 7.67-7.68 (1H, d, J=1.96 Hz), 8.06-8.08 (1H, dd, J=8.28, 1.56 Hz), 8.94-8.95 (1H, m);

Mass (m/z): 178.2 (M+H)$^+$, 180.2 (M+H)$^+$.

Step (ii): Preparation of 6-Chloro-8-methyl-5-nitro quinoline

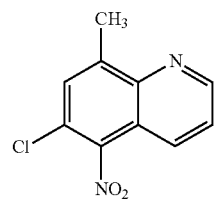

Nitric acid (400 mL) was added to precooled concentrated sulfuric acid (400 mL) at 10° C. over a period of 1 hour, followed by addition of 6-chloro-8-methyl quinoline (80.00 grams, 0.451 mole, obtained in above step) at the same temperature. The reaction mixture was brought to RT and stirred further for 3 hours. The progress of the reaction was monitored by TLC. After completion of the reaction (TLC), the mass was poured onto chilled water (1500 mL) and the pH was adjusted to ~9.5 using 40% aqueous sodium hydroxide solution. The yellow solids, thus obtained, were filtered and washed with n-hexane (500 mL) and dried under vacuum to afford the title compound.

Yield: 90 grams (90%).
¹H-NMR (δ ppm): 2.85 (3H, s), 7.58-7.61 (1H, m), 7.64 (1H, s), 8.06-9.03 (2H, m);
Mass (m/z): 223.1 (M+H)⁺, 225.2 (M+H)⁺.

Step (iii): Preparation of 6-Chloro-5-nitro quinoline-8-carboxylic acid

Chromium trioxide (121.50 grams, 1.215 mole) was added to a stirred solution of 6-chloro-8-methyl-5-nitro quinoline (90.00 grams, 0.404 mole, obtained in above step) in sulfuric acid (600 mL) at 45° C. During addition exotherm was observed. Reaction mass temperature was slowly raised to 60° C. and stirred further for 4 hours at 60° C. The progress of the reaction was monitored by TLC. After completion of the reaction (TLC), the mass was cooled to RT and quenched into chilled water (2000 mL). The compound was extracted with ethyl acetate (5 ×1000 mL) and the resulting organic layer was washed with brine solution (1000 mL) and dried over sodium sulphate. The organic phase was concentrated under vacuum to obtain the crude residue, which was further purified by flash chromatography using methanol:ethyl acetate (5:95) to afford the title compound.
Yield: 50 grams (49%).
¹H-NMR (δ ppm): 7.92-7.94 (1H, m), 8.40-8.47 (2H, m), 9.20 (1H, s), 14.89 (1H, bs);
Mass (m/z): 253.1 (M+H)⁺, 255.2 (M+H)⁺.

Preparation 2: Preparation of 5-Amino-6-chloro-N-[(4-piperidinyl)methyl] quinoline-8-carboxamide

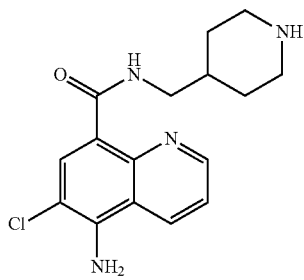

Step (i): Preparation of 6-Chloro-5-nitro-N-{[1-(tert-butoxycarbonyl)-4-piperidinyl] methyl}quinoline-8-carboxamide

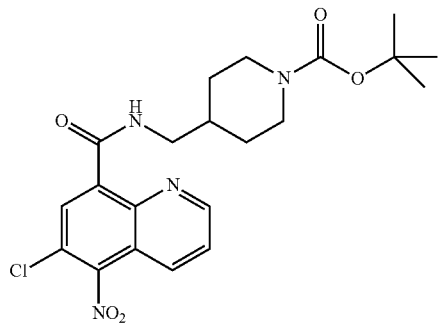 [SMILES: CC(C)(C)OC(=O)N1CCC(CNC(=O)c2cc(Cl)c([N+](=O)[O-])c3cccnc23)CC1]

A solution of 6-chloro-5-nitro quinoline-8-carboxylic acid (10 grams, 0.039 mole, obtained from preparation 1) and carbonyldiimidazole (7.71 grams, 0.047 mole) in dichloromethane (150 mL) was stirred for 3 hours at RT. Then added a solution of tert-butyl 4-aminomethyl piperidine-1-carboxylate solution (10.15 grams, 0.044 mole) in dichloromethane (150 mL). The reaction mass was stirred over night (12 hours) at RT under nitrogen atmosphere, while monitoring the progress of the reaction by TLC. After completion of the reaction (TLC), the reaction mass was washed with chilled water (200 mL), brine solution (200 mL) and dried over sodium sulphate. The organic phase was concentrated on rotavacuum to obtain the crude residue, which was further purified by flash chromatography using (ethyl acetate:n-hexane (30:70)) to afford the title compound.
Yield: 15 grams (85%).
¹H-NMR (δ ppm): 1.21-1.32 (2H, m), 1.45 (9H, s), 1.78-1.90 (3H, m), 2.72-2.80 (2H, m), 3.52-3.61 (2H, m), 4.09-4.13 (2H, m), 7.68-7.71 (1H, m), 8.15-8.17 (1H, dd, J=8.72, 1.32 Hz), 8.94 (1H, s), 9.04-9.06 (1H, m), 11.02-11.08 (1H, t);
Mass (m/z): 449.3 (M+H)⁺, 451.3 (M+H)⁺.

Step (ii): Preparation of 5-Amino-6-Chloro-N-{[1-(t-butoxycarbonyl)-4-piperidinyl]methyl}quinoline-8-carboxamide

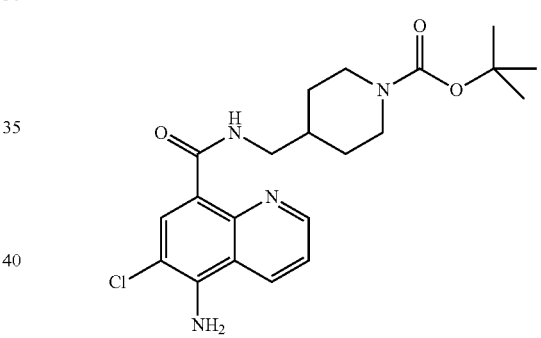

Added iron powder (6.23 grams, 0.111 mole) and ammonium chloride (6 grams, 0.111 mole) to a solution of 6-chloro-5-nitro-N-{[1-(tert-butoxycarbonyl)-4-piperidinyl]methyl}quinoline-8-carboxamide (10 grams, 0.022 mole, obtained in above step) in ethanol (200 mL), tetrahydrofuran (THF) (100 mL) and water (50 mL) mixture. The reaction mass was stirred for 6 hours at 75° C., while monitoring the progress of the reaction by TLC. After completion of the reaction (TLC), the reaction mass was cooled to RT and filtered through celite bed. The filtrate was concentrated, the slurry, thus obtained, was partitioned between ethyl acetate (200 mL) and water (100 mL) by stirring for 30 minutes. Both the layers were separated and the aqueous phase was extracted with ethyl acetate (3×75 mL). The combined organic phase was washed with water (100 mL), brine solution (100 mL) and dried over sodium sulphate. The organic phase was concentrated under vacuum, and the crude residue, thus obtained, was further purified by flash chromatography using ethyl acetate:n-hexane (50:50) to afford the title compound.
Yield: 8 grams (85%).
¹H-NMR (δ ppm): 1.02-1.18 (2H, m), 1.49 (9H, s), 1.81-1.90 (3H, m), 2.74-2.81 (2H, m), 3.51-3.60 (2H, m), 4.10-4.16 (2H, m), 4.99 (2H, s), 7.47-7.51 (1H, m), 8.25-8.27 (1H, dd, J=8.56, 1.20 Hz), 8.80 (1H, s), 8.91-8.93 (1H, m), 11.12-11.15 (1H, t);

Mass (m/z): 419.3 (M+H)$^+$, 421.4 (M+H)$^+$.

Step (iii): Preparation of 5-Amino-6-chloro-N-[(4-piperidinyl)methyl] quinoline-8-carboxamide Ethanolic hydrogen chloride (23% w/w, 30.3 grams, 0.191 mole) was added to a solution of 5-amino-6-chloro-N-{[1-(t-butoxycarbonyl)-4-piperidinyl]methyl}quinoline-8-carboxamide (8.00 grams, 0.019 mole, obtained in above step) in ethanol (200 mL) at 10° C. The reaction mass was stirred over night at RT, while monitoring the progress of the reaction by TLC. After completion of the reaction (TLC), the reaction mass was concentrated and the slurry, thus obtained, was dissolved in chilled water (150 mL). The pH was adjusted to ~9.5 using aqueous ammonia solution and the product was extracted with dichloromethane (3×100 mL). The combined organic phase was washed with water (100 mL), brine solution (100 mL) and dried over sodium sulphate. The organic phase was concentrated under vacuum to afford the title compound.

Yield: 5.70 grams (95%).

$^1$H-NMR (δ ppm): 1.02-1.18 (2H, m), 1.54-1.60 (3H, m), 2.35-2.40 (2H, m), 2.86-2.89 (2H, m), 3.23-3.29 (3H, m), 6.88 (2H, bs), 7.52-7.55 (1H, dd, m), 8.35 (1H, s), 8.80-8.83 (1H, m), 8.91-8.92 (1H, m), 10.85-10.88 (1H, t);

Mass (m/z): 319.4 (M+H)$^+$, 321.4 (M+H)$^+$.

Preparation 3: Preparation of
5-Amino-6-chloro-N-(4-piperidinyl)
quinoline-8-carboxamide

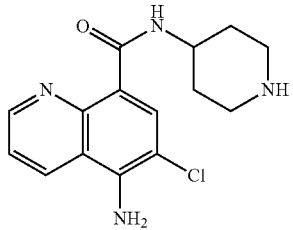 [SMILES: Nc1c(Cl)cc(C(=O)NC2CCNCC2)c2ncccc12]

Step (i): Preparation of 6-Chloro-5-nitro-A-[1-(t-butyloxycarbonyl)-4-piperidinyl]quinoline-8-carboxamide

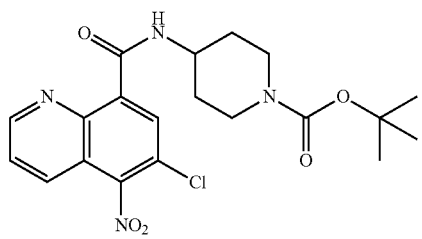 [SMILES: CC(C)(C)OC(=O)N1CCC(NC(=O)c2cc(Cl)c([N+](=O)[O-])c3cccnc23)CC1]

Ethyl chloroformate (0.55 gram, 0.005 mole) was added to a solution of 6-chloro-5-nitro quinoline-8-carboxylic acid (1 gram, 0.004 mole, obtained from preparation 1) and triethylamine (1.20 grams, 0.012 mole) in dichloromethane (15 mL) at 0° C. The reaction mass was stirred for 2 hours at 0° C., then a solution of t-butyl 4-amino piperidine-1-carboxylate (1.02 grams, 5.00 mole) in dichloromethane (10 mL) was added at 0° C. The reaction mass was stirred over night at RT, while monitoring the progress of the reaction by TLC. After completion of the reaction (TLC), the reaction mass was washed with chilled water (15 mL), brine solution (15 mL) and dried over sodium sulphate. The organic phase was concentrated under vacuum to obtain the crude residue, which was further purified by flash chromatography using ethyl acetate:n-hexane (30:70) to afford the title compound.

Yield: 1.20 grams (69%).

$^1$H-NMR (δ ppm): 1.48 (9H, s), 1.58-1.63 (2H, m), 2.06-2.10 (2H, m), 3.08-3.14 (2H, m), 3.98-4.07 (2H, m), 4.22-4.33 (1H, m), 7.68-7.77 (1H, m), 8.14-8.16 (1H, dd, J=8.64, 1.36 Hz), 8.93 (1H, s), 9.02-9.04 (1H, m), 11.02-11.04 (1H, d);

Mass (m/z): 435.2 (M+H)$^+$, 437.1 (M+H)$^+$.

Step (ii): Preparation of 5-Amino-6-chloro-N-[1-(t-butyloxy carbonyl)-4-piperidinyl]quinoline-8-carboxamide

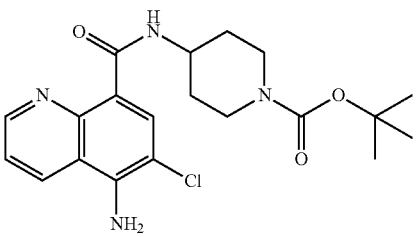

Iron powder (0.623 gram, 0.001 mole) and ammonium chloride (0.60 gram, 0.001 mole) were added to a solution of 6-chloro-5-nitro-N-[1-(t-butyloxycarbonyl)-4-piperidinyl]quinoline-8-carboxamide (1.00 gram, 0.002 mole, obtained in above step) in ethanol (20 mL), THF (10 mL) and water (5 mL) mixture. The reaction mass was stirred for 6 hours at 75° C. while monitoring the progress of the reaction by TLC. After completion of the reaction (TLC), the reaction mass was cooled to RT and filtered through celite bed. The filtrate was concentrated and the slum, thus obtained, was partitioned between ethyl acetate (20 mL) and water (15 mL) by stirring for 20 minutes. Both the layers were separated and the aqueous phase was extracted with ethyl acetate (3×10 mL). The combined organic phase was washed with water (15 mL), brine solution (15 mL) and dried over sodium sulphate. The organic phase was concentrated under vacuum to obtain a crude residue, which was further purified by flash chromatography using ethyl acetate:n-hexane (50:50) to afford the title compound.

Yield: 0.80 gram (85%).

$^1$H-NMR (δ ppm): 1.41 (9H, s), 1.43-1.50 (2H, m), 1.89-1.93 (2H, m), 3.00-3.09 (2H, m), 3.80-3.83 (2H, m), 4.04-4.10 (1H, m), 6.94 (2H, bs), 7.56-7.59 (1H, m), 8.38 (1H, s), 8.84-8.86 (1H, m), 8.96-8.97 (1H, m), 11.00-11.02 (1H, d);

Mass (m/z): 405.3 (M+H)$^+$, 407.3 (M+H)$^+$.

Step (iii): Preparation of 5-Amino-6-chloro-N-(4-piperidinyl) quinoline-8-carboxamide Ethanolic hydrogen chloride (23% w/w, 3.03 gram, 0.019 mole) was added to a stirred solution of 5-amino-6-chloro- N-[1-(t-butyloxy carbonyl)-4-piperidinyl] quinoline-8-carboxamide (0.80 gram, 0.002 mole, obtained in above step) in ethanol (20 mL) at 10° C. The reaction mass was stirred over night at RT, while monitoring the progress of the reaction by TLC. After completion of the reaction (TLC), the reaction mass was concentrated and the slurry, thus obtained, was dissolved in chilled water (15 mL). The pH of the solution was adjusted to ~9.5 using aqueous ammonia solution and the product was extracted with dichloromethane (3×10 mL). The combined organic phase was washed with water (10 mL), brine solution (10 mL) and dried over sodium sulphate. The organic phase was concentrated under vacuum to afford the title compound.

Yield: 0.55 gram (90%).

$^1$H-NMR (δ ppm): 1.67-1.72 (2H, m), 2.03-2.13 (2H, m), 2.62-2.70 (2H, m), 2.89-2.94 (2H, m), 2.96-2.99 (1H, m), 4.03-4.14 (1H, m), 6.90 (2H, bs), 7.50-7.53 (1H, m), 8.49 (1H, s), 8.65-8.68 (1H, m), 8.89-8.90 (1H, m), 10.90-10.91 (1H, d);

Mass (m/z): 305.3 (M+H)$^+$, 307.3 (M+H)$^+$.

Preparation 4: Preparation of 5-Amino-6-chloro-N-{[3-azabicyclo[3.1.0]hex-6-yl]methyl}quinoline-8-carboxamide

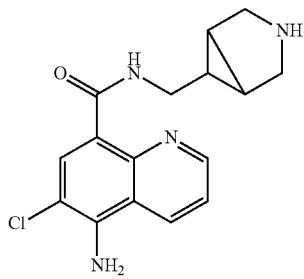 [SMILES: Nc1c(Cl)cc(C(=O)NCC2C3CNCC32)c2ncccc12]

Step (i): Preparation of (3-Aza bicyclo[3.1.0]hex-6-yl) methanol

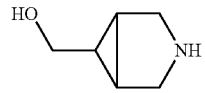

Hydrogen gas was passed into a stirred solution of (3-benzyl-3-azabicyclo[3.1.0]hex-6-yl)methanol (15.50 grams, 0.076 mole) and palladium hydroxide (7.75 grams, 50% w/w) in methanol (150 mL) over a period of 6 hours, while monitoring the progress of the reaction by TLC. After completion of the reaction (TLC), the reaction mass was filtered through celite bed and the filtrate was concentrated under vacuum to afford the title compound.

Yield: 8.20 grams (69%).

$^1$H-NMR (δ ppm): 0.89-0.96 (1H, m), 1.35-1.42 (2H, m), 2.05-2.07 (2H, m), 2.85-2.88 (2H, m), 2.98-3.01 (2H, m), 3.50-3.52 (1H, m), 3.94-3.96 (1H, m);

Mass (m/z): 114.3 (M+H)$^+$.

Step (ii): Preparation of tert-butyl 6-hydroxymethyl-3-azabicyclo[3.1.0]hexane-3-carboxylate

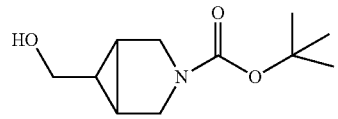

Di-tert-butyl dicarbonate (16.96 grams, 0.077 mole) was added to a solution of (3-aza bicyclo[3.1.0]hex-6-yl) methanol (8.00 grams, 0.070 mole, obtained in above step) and triethylamine (11.40 grams, 0.112 mole) in dichloromethane (150 mL) at 10° C. The reaction mass was stirred for 2 hours at 10° C., while monitoring the progress of the reaction by TLC. After completion of the reaction (TLC), the reaction mass was washed with chilled water (50 mL), brine solution (50 mL) and dried over sodium sulphate. The organic phase was concentrated under vacuum to obtain a crude residue, which was further purified by flash chromatography using ethyl acetate:n-hexane (50:50) to afford the title compound.

Yield: 7.84 crams (52%).

$^1$H-NMR (δ ppm): 0.92-0.97 (1H, m), 1.33-1.36 (I H, m), 1.43 (9H, s), 1.55-1.60 (2H, m), 3.32-3.37 (2H, m), 3.43-3.48 (1H, m), 3.53-3.58 (2H, m), 3.61-3.64 (1H, m);

Mass (m/z): 158.1 (M+H)$^+$.

Step (iii): Preparation of tert-butyl 6-methanesulfonyloxymethyl-3-aza bicyclo[3.1.0]hexane-3-carboxylate

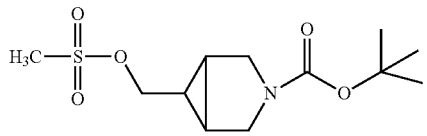 [SMILES: CC(C)(C)OC(=O)N1CC2C(COS(C)(=O)=O)C2C1]

A solution of methanesulfonylchloride (4.42 grams, 0.038 mole) in dichloromethane (25 mL) was added to a solution of tert-butyl 6-hydroxymethyl-3-azabicyclo[3.1.0]hexane-3-carboxylate (7.80 grams, 0.036 mole, obtained in above step) and triethylamine (5.58 grams, 0.055 mole) in dichloromethane (100 mL) at 0° C. The reaction mass was stirred over night at RT, while monitoring the progress of the reaction by TLC. After completion of the reaction (TLC), the reaction mass was washed with chilled water (50 mL), brine solution (50 mL) and dried over sodium sulphate. The organic phase was concentrated under vacuum to afford the title compound.

Yield: 9.30 grams (87%).

$^1$H-NMR (δ ppm): 1.11-1.15 (1H, m), 1.40-1.42 (1H, m), 1.45 (9H, s), 3.05 (3H, s), 3.17-3.19 (1H, m), 3.37-3.41 (2H, m), 3.58-3.68 (2H, m), 4.09-4.18 (2H, m);

Mass (m/z): 236.2 (M−56)$^+$.

Step (iv): Preparation of tert-butyl 6-Azidomethyl-3-azabicyclo[3.1.0]hexane-3-carboxylate

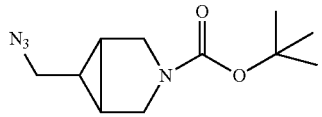 [SMILES: CC(C)(C)OC(=O)N1CC2C(CN=[N+]=[N-])C2C1]

Sodium azide (7.30 grams, 0.112 mole) was added to a solution of tert-butyl 6-methanesulfonyloxymethyl-3-azabicyclo[3.1.0]hexane-3-carboxylate (9.30 grams, 0.039 mole, obtained in above step) and potassium carbonate (11.00 grams, 0.079 mole) in dimethylformamide (100 mL) at 10° C. Then the reaction mass was stirred over night at RT, while monitoring the progress of the reaction by TLC. After completion of the reaction (TLC), the reaction mass was poured onto chilled water (200 mL). The product was extracted with ethylacetate (3×150 mL) and the combined organic phase was washed with chilled water (150 mL), brine solution (150 mL) and dried over sodium sulphate. The organic phase was concentrated under vacuum to afford the title compound.

Yield: 7 grams (90%).

$^1$H-NMR (δ ppm): 0.97-1.00 (1H, m), 1.45 (9H, s), 1.50-1.53 (2H, m), 3.10-3.15 (1H, m), 3.22-3.27 (1H, m), 3.35-3.39 (2H, m), 3.57-3.67 (2H, m);

Mass (m/z): 183.3 (M−56)$^+$.

Step (v): Preparation of tert-butyl 6-aminomethyl-3-azabicyclo[3.1.0]hexane-3-carboxylate

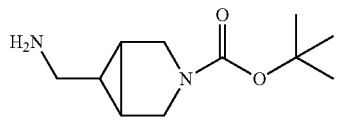

A solution of tert-butyl 6-azidomethyl-3-azabicyclo[3.1.0]hexane-3-carboxylate (1.50 grains, 0.006 mole, obtained in above step) in THF (30 mL) and water (3 mL) mixture was treated with triphenylphosphine (2.1 grams, 0.008 mole). The reaction mass was stirred for 36 hours at RT, while monitoring the progress of the reaction by TLC. After completion of the reaction (TLC), the reaction mass was concentrated under vacuum to obtain a crude residue, which was further purified by flash chromatography using triethylamine:methanol: dichloromethane (2:8:90) to afford the title compound.

Yield: 1.20 grams (90%).

$^1$H-NMR (δ ppm): 0.66-0.70 (1H, m), 0.95-0.99 (1H, t), 1.17-1.19 (1H, m), 1.33 (9H, s), 1.53-1.55 (2H, m), 2.67-2.69 (2H, m), 3.36-3.41 (2H, m), 7.73 (2H, bs);

Mass (m/z): 213.3 (M+H)$^+$.

Step (vi): Preparation of 6-Chloro-5-nitro-N-{[1-(tert-butoxycarbonyl)-3-azabicyclo[3.1.0]hex-6-yl]methyl}quinoline-8-carboxamide

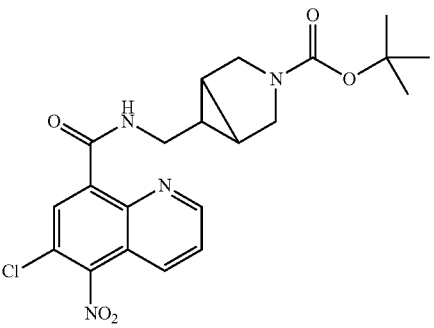 [SMILES: CC(C)(C)OC(=O)N1CC2C(CNC(=O)c3cc(Cl)c([N+](=O)[O-])c4cccnc34)C2C1]

A solution of 6-chloro-5-nitro quinoline-8-carboxylic acid (1.90 grams, 0.019 mole, obtained from preparation 1) and CDI (1.34 grams, 0.008 mole) in dichloromethane (15 mL) was stirred for 3 hours at RT. Then a solution of tert-butyl 6-aminomethyl-3-aza bicyclo[3.1.0]hexane-3-carboxylate (1.34 grams, 0.006 mole, obtained in the above step) in dichloromethane (10 mL) was added at RT. The reaction mass was stirred over night (12 hours) at RT under nitrogen atmosphere, while monitoring the progress of the reaction by TLC. After completion of the reaction (TLC), the reaction mass was washed with chilled water (15 mL), brine solution (15 mL) and dried over sodium sulphate. The organic phase was concentrated on rotavacuum to obtain the crude residue, which was further purified by flash chromatography using (ethyl acetate:n-hexane (30:70) to afford the title compound Yield: 2.7 grams (80%).

$^1$H-NMR (δ ppm): 1.07-1.09 (1H, m), 1.25-1.31 (1H, m), 1.46 (9H, s), 1.60-1.63 (2H, m), 3.36-3.49 (2H, m), 3.56-3.70 (2H, m), 4.12-4.16 (1H, m), 7.73-7.76 (1H, m), 8.19-8.21 (1H, dd, J=8.72, 1.16 Hz), 8.97 (1H, s), 9.10-9.11 (1H, m), 11.05-11.08 (1H, t);

Mass (m/z): 447.4 (M+H)$^+$, 449.3 (M+H)$^+$.

Step (vii): Preparation of 5-Amino-6-chloro-N-{[1-(tert-butoxycarbonyl)-3-azabicyclo[3.1.0]hex-6-yl]methyl}quinoline-8-carboxamide

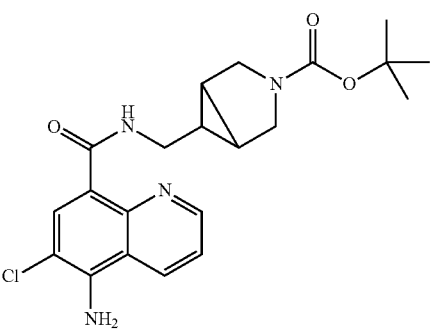 [SMILES: CC(C)(C)OC(=O)N1CC2C(CNC(=O)c3cc(Cl)c(N)c4cccnc34)C2C1]

Iron powder (0.80 gram, 0.014 mole) and ammonium chloride (0.75 gram, 0.014 mole) were added to a solution of 5-nitro-6-chloro-N-{[1-(tert-butoxycarbonyl)-3-azabicyclo[3.1.0]hex-6-yl]methyl}quinoline-8-carboxamide (1.30 grams, 0.003 mole, obtained in above step) in ethanol (26 mL), THF (13 mL) and water (6.5 mL) mixture. The reaction mass was stirred for 6 hours at 75° C., while monitoring the progress of the reaction by TLC. After completion of the reaction (TLC), the reaction mass was cooled to RT and filtered through celite bed. The filtrate was concentrated and the slurry, thus obtained, was partitioned between ethyl acetate (20 mL) and water (15 mL) by stirring for 30 minutes. Then separated the both the layers and the aqueous phase was extracted with ethylacetate (3×10 mL). The combined organic phase was washed with water (15 mL), brine solution (15 mL) and dried over sodium sulphate. The organic phase was concentrated under vacuum to obtain a crude residue, which was further purified by flash chromatography using ethyl acetate:n-hexane (80:20) to afford the title compound.

Yield: 1 gram (83%).

$^1$H-NMR (δ ppm): 0.78-0.82 (1H, m), 1.09-1.12 (1H, m), 1.32 (9H, s), 1.47-1.51 (2H, m), 3.20-3.26 (2H, m), 3.36-3.40 (3H, m), 6.89 (2H, bs), 7.53-7.56 (1H, m), 8.35 (1H, s), 8.80-8.83 (1H, dd, J=8.44, 1.00 Hz), 8.92-8.93 (1H, m), 10.85-10.88 (1H, t);

Mass (m/z): 417.3 (M+H)$^+$, 419.1 (M+H)$^+$.

Step (viii): Preparation of 5-Amino-6-chloro-N-{[3-azabicyclo[3.1.0]hex-6-yl]methyl}quinoline-8-carboxamide Ethanolic hydrogen chloride (23% w/w, 3.03 gram, 0.019 mole) was added to a stirred solution of 5-amino-6-chloro-N-{[1-(tert-butoxycarbonyl)-3-azabicyclo[3.1.0]hex-6-yl]methyl}quinoline-8-carboxamide (0.85 gram, 0.002 mole, obtained in above step) in ethanol (15 mL) at 10° C. The reaction mass was stirred over night at RT, while monitoring the progress of the reaction by TLC. After completion of the reaction (TLC), the reaction mass was concentrated and the slurry, thus obtained, was dissolved in water (15 mL). The pH was adjusted to ~9.5 using aqueous ammonia solution and the product was extracted with dichloromethane (3×10 mL). The combined organic phase was washed with water (10 mL), brine solution (10 mL) and dried over sodium sulphate. The organic phase was concentrated under vacuum to afford the title compound.

Yield: 0.58 gram (90%).

$^1$H-NMR (δ ppm): 0.98-1.01 (1H, m), 1.12-1.17 (1H, m), 1.35-1.36 (2H, m), 1.75-1.77 (1H, m), 1.96-1.99 (1H, m), 2.61-2.64 (2H, m), 2.81-2.84 (2H, m), 6.93 (2H, bs), 7.56-7.60 (1H, dd, J=8.60 Hz, 4.20 Hz), 8.39 (1H, s), 8.84-8.86 (1H, m), 8.95-8.96 (1H, m), 10.87-10.90 (1H, t);

Mass (m/z): 317.2 (M+H)$^+$, 319.4 (M+H)$^+$.

Preparation 5: Preparation of 5-Amino-6-chloro-N-[4-fluoro-(4-piperidinyl)methyl]quinoline-8-carboxamide

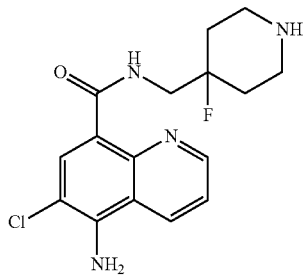 [SMILES: Nc1c(Cl)cc(C(=O)NCC2(F)CCNCC2)c2ncccc12]

Step (i): Preparation of tert-butyl 1-Oxa-6-aza spiro[2.5]octane-6-carboxylate

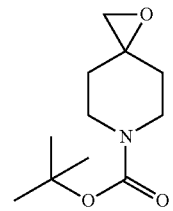

Trimethylsulfoxonium iodide (13.3 grams, 0.06 mole) was added to a stirred solution of sodium hydride (60% dispersion in oil, 3.0 grams, 0.126 mole) in THF (150 mL) at 10° C. Reaction mass temperature was slowly raised to RT and stirred further for 2 hours at the same temperature. Reaction mass was then cooled to 10° C. and added N-boc-piperidine-4-one (10 grams, 0.05 mole) solution in THF (50 mL) at the same temperature. Then reaction mass temperature was slowly raised to RT and stirred for 3 hours at same temperature. The progress of the reaction was monitored by TLC. After completion of the reaction (TLC), the mass was quenched in chilled water (300 mL), the compound was extracted with dichloromethane (3×150 mL). The combined organic phase was washed with water (100 mL), brine solution (100 mL) and dried over sodium sulphate. The organic phase was concentrated on rotavacuum to obtain the crude residue, which was further purified by flash chromatography using ethyl acetate:n-hexane (15:85) to afford the title compound.

Yield: 7.1 grams (66%).

$^1$H-NMR (δ ppm): 1.47 (9H, s), 1.59-1.62 (2H, m), 1.76-1.83 (2H, m), 2.69 (2H, s), 3.39-3.45 (2H, m), 3.70-3.73 (2H, m);

Mass (m/z): 158.2 (M−56)$^+$.

Step (ii): Preparation of 4-[(Dibenzylamino)methyl]-4-hydroxy piperidine-1-carboxylic acid tert-butyl ester

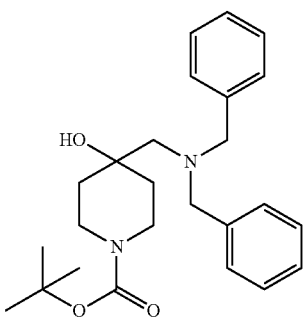 [SMILES: CC(C)(C)OC(=O)N1CCC(O)(CN(Cc2ccccc2)Cc2ccccc2)CC1]

Dibenzylamine (7.98 grams, 0.04 mole) vas added to a stirred solution of tert-butyl 1-oxa-6-aza-spiro[2.5]octane-6-carboxylate (7.86 grams, 0.036 mole, obtained in above step) and triethylamine (11.19 grams, 0.118 mole) in methanol (100 mL) at RT. Then reaction mass temperature was slowly raised to 75° C. and stirred for 38 hours at same temperature. The progress of the reaction was monitored by TLC. After completion of the reaction (TLC), the reaction mass was concentrated on rotavacuum to obtain the crude residue, which was further purified by flash chromatography using ethyl acetate:n-hexane (15:85) to afford the title compound.

Yield: 7.1 grams (46%).

¹H-NMR (δ ppm): 1.43 (9H, s), 1.89-1.94 (2H, m), 2.14-2.19 (1H, m), 2.55-2.60 (2H, m), 2.92 (1H, s), 3.03-3.09 (2H, m), 3.43-3.45 (1H, m), 3.64 (4H, bs), 3.69-3.84 (2H, m), 7.16-7.35 (10H, m);

Mass (m/z): 411.3 (M+H)⁺

Step (iii): Preparation of tert-Butyl 4-[(Dibenzylamino)methyl]-4-fluoro piperidine-1-carboxylate

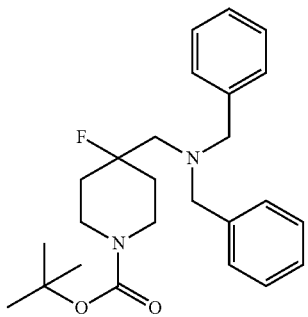 [SMILES: CC(C)(C)OC(=O)N1CCC(F)(CN(Cc2ccccc2)Cc2ccccc2)CC1]

Diethylaminosulfur trifluoride (DAST) (3.3 grams, 0.02 mole) was added to a stirred solution of tert-butyl 4-[(dibenzylamino) methyl]-4-hydroxy piperidine-1-carboxylate (7 grams, 0.017 mole, obtained in the above step) in DCM (70 mL) at −40° C. Then reaction mass temperature was slowly raised to RT and stirred over night at the same temperature. The progress of the reaction was monitored by thin layer chromatography. After completion of the reaction (thin layer chromatography), the mass was quenched in chilled water (100 mL). The pH of the mass was adjusted to ~9.5 using aqueous ammonia, the compound was extracted with DCM (3×50 mL). The combined organic phase was washed with water (75 mL), brine solution (75 mL) and dried over sodium sulphate. The organic phase was concentrated on rotavacuum to obtain the crude residue, which was further purified by flash chromatography using ethyl acetate:n-hexane (5:95) to afford the title compound.

Yield: 4.35 grams (61%).

¹H-NMR (δ ppm): 1.45 (9H, s), 1.89-1.94 (2H, m), 2.14-2.19 (1H, m), 2.55-2.60 (2H, m), 3.03-3.09 (2H, m), 3.43-3.45 (1H, m), 3.64 (4H, bs), 3.69-3.84 (2H, m), 7.16-7.35 (10H, m);

Mass (m/z): 413.3 (M+H)⁺.

Step (iv): Preparation of tert-Butyl 4-aminomethyl-4-fluoro piperidine-1-carboxylate

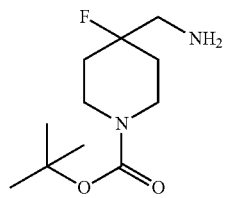 [SMILES: CC(C)(C)OC(=O)N1CCC(F)(CN)CC1]

Hydrogen gas was passed into a stirred solution of tert-butyl 4-[(dibenzylamino)-methyl]-4-fluoro-piperidine-1-carboxylate (4.12 grams, 10 mmole, obtained in the above step) and palladium hydroxide (2 grams, 50% w/w) in methanol (50 mL) over a period of 8 hours. The progress of the reaction was monitored by thin layer chromatography. After completion of the reaction (thin layer chromatography), the reaction mass was filtered through celite bed and the filtrate was concentrated on rotavacuum to afford the title compound.

Yield: 1.97 grams (85%).

¹H-NMR (δ ppm): 1.38 (9H, s), 1.44-1.71 (6H, m), 2.60-2.64 (2H, m), 2.95 (2H, bs), 3.73-3.76 (2H, m);

Mass (m/z): 233.2 (M+H)⁺.

Step (v): Preparation of 6-Chloro-5-nitro-N-{[4-fluoro-1-(tert-butoxycarbonyl)-4-piperidinyl] methyl}quinoline-8-carboxamide

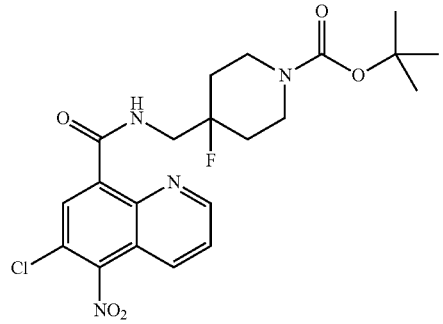 [SMILES: CC(C)(C)OC(=O)N1CCC(F)(CNC(=O)c2cc(Cl)c([N+](=O)[O-])c3cccnc23)CC1]

A solution of 6-chloro-5-nitro quinoline-8-carboxylic acid (1.3 grams, 5.14 mmole) and carbonyldiimidazole (1 gram, 6.17 mmole) in DCM (25 mL) was stirred for 3 hours at RT. Then added a solution of with 4-aminomethyl-4-fluoro piperidine-1-carboxylic acid tert-butyl ester (1.2 grams, 5.17 mmole, obtained in above step) in DCM (10 mL). The reaction mass was stirred over night (12 hours) at RT under nitrogen atmosphere, while monitoring the the progress of the reaction by TLC. After completion of the reaction (TLC), the reaction mass was washed with chilled water (10 mL), brine solution (10 mL) and dried over sodium sulphate. The organic phase was concentrated on rotavacuum to obtain the crude residue, which was further purified by flash chromatography using (ethyl acetate:n-hexane (30:70) to afford the title compound.

Yield: 1.46 grams (61%).

¹H-NMR (δ ppm): 1.45 (9H, s), 1.61-1.72 (2H, m), 1.85-1.93 (2H, m), 3.11-3.16 (2H, m), 3.81-4.13 (4H, m), 7.69-7.72 (1H, m), 8.15-8.18 (1H, m), 8.92 (1H, s), 9.07-9.08 (1H, m), 11.23-11.25 (1H, t);

Mass (m/z): 467.2 (M+H)⁺, 469.2 (M+H)⁺.

Step (vi): Preparation of 5-Amino-6-chloro-N-{[4-fluoro-1-(t-butoxycarbonyl)-4-piperidinyl]methyl}quinoline-8-carboxamide

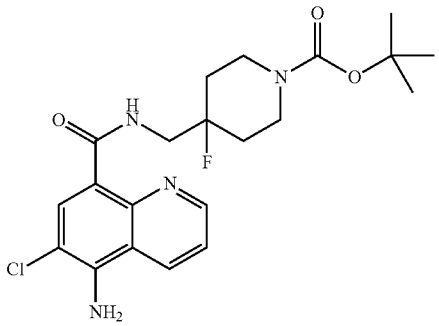

Added iron powder (0.41 grams, 7.50 mmole) and ammonium chloride (0.4 grams, 7.50 mmole) to a solution of 6-chloro-5-nitro-N-{[4-fluoro-1-(tert-butoxycarbonyl)-4-piperidinyl]methyl}quinoline-8-carboxamide (0.7 grams, 1.50 mmole, obtained in above step) in ethanol (14 mL), THF (7 mL) and water (3.5 mL) mixture. The reaction mass was stirred for 6 hours at 75° C., while monitoring the progress of the reaction by TLC. After completion of the reaction (TLC), the reaction mass was cooled to RT and filtered through celite bed. The filtrate was concentrated, the slurry, thus obtained, was partitioned between ethyl acetate (25 mL) and water (10 mL) by stirring for 30 minutes. Both the layers were separated and the aqueous phase was extracted with ethyl acetate (3×5 mL). The combined organic phase was washed with water (15 mL), brine solution (15 mL) and dried over sodium sulphate. The organic phase was concentrated under vacuum, and the crude residue, thus obtained, was further purified by flash chromatography using ethyl acetate:n-hexane (50:50) to afford the title compound.

Yield: 0.52 grams (80%).

$^1$H-NMR (δ ppm): 1.46 (9H, s), 1.60-1.68 (2H, m), 1.83-1.90 (2H, m), 3.10-3.16 (2H, m), 3.80-4.08 (4H, m), 5.00 (2H, s), 7.46-7.49 (1H, m), 8.23-8.25 (1H, m), 8.75 (1H, s), 8.91-8.93 (1H, m), 11.31-11.33 (1H, t);

Mass (m/z): 437.3 (M+H)$^+$, 439.2 (M+H).

Step (vii): Preparation of 5-Amino-6-chloro-N-[4-fluoro-(4-piperidinyl)methyl] quinoline-8-carboxamide Ethanolic hydrogen chloride (23% w/w, 1.81 grams, 11.45 mmole) was added to a solution of 5-amino-6-chloro-N-{[4-fluoro-1-(t-butoxycarbonyl)-4-piperidinyl]methyl}quinoline-8-carboxamide (0.5 grams. 1.14 mmole, obtained in above step) in ethanol (10 mL) at 10° C. The reaction mass was stirred over night at RT, while monitoring the progress of the reaction by TLC. After completion of the reaction (TLC), the reaction mass was concentrated and the slurry, thus obtained, was dissolved in chilled water (15 mL). The pH was adjusted to ~9.5 using aqueous ammonia solution and the product was extracted with DCM (3 ×10 mL). The combined organic phase was washed with water (10 mL), brine solution (10 mL) and dried over sodium sulphate. The organic phase was concentrated under vacuum to afford the title compound.

Yield: 0.34 grams (90%).

$^1$H-NMR (δ ppm): 1.55-1.72 (5H, m). 2.66-2.76 (4H, m), 3.61-3.68 (2H, m), 6.95 (2H, s), 7.55-7.58 (1H, m), 8.40 (1H, s), 8.84-8.93 (2H, m), 11.07-11.09 (1H, t);

Mass (m/z): 337.2 (M+H)$^+$, 339.2 (M+H)$^+$.

Preparation 6: Preparation of 5-Amino-6-chloro-N-[4-hydroxy-(4-piperidinyl)methyl]quinoline-8-carboxamide

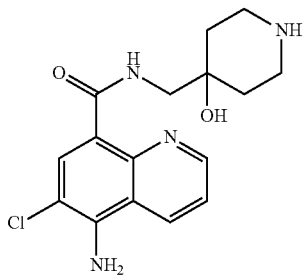 [SMILES: Nc1c(Cl)cc(C(=O)NCC2(O)CCNCC2)c2ncccc12]

Step (i): Preparation of t-Butyl 4-aminomethyl-4-hydroxy piperidine-1-carboxylate

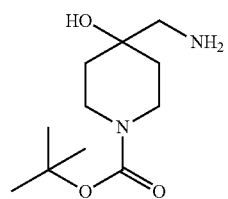 [SMILES: CC(C)(C)OC(=O)N1CCC(O)(CN)CC1]

tert-Butyl 1-Oxa-6-aza-spiro[2.5]octane-6-carboxylate (0.5 grams, 2.34 mmole) was added to methanolic ammonia solution (20 mL, 14.83% w/v) at room temperature. Then reaction mass was stirred for 40 hours at room temperature in a closed vessel. The progress of the reaction was monitored by TLC. After completion of the reaction (TLC), the reaction mass was concentrated on rotavacuum to obtain the title compound.

Yield: 0.41 gram (76%).

$^1$H-NMR. (δ ppm): 1.35-1.69 (16H, m), 2.61 (2H, s), 3.10-3.20 (2H, m), 3.81-3.90 (2H, m);

Mass (m/z): 231.3 (M+H)$^+$.

Step (ii): Preparation of 6-Chloro-5-nitro-N-{[4-hydroxy-1-(tert-butoxycarbonyl)-4-piperidinyl]methyl}quinoline-8-carboxamide

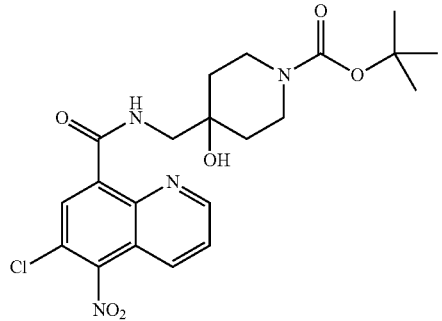 [SMILES: CC(C)(C)OC(=O)N1CCC(O)(CNC(=O)c2cc(Cl)c([N+](=O)[O-])c3cccnc23)CC1]

A solution of 6-chloro-5-nitro quinoline-8-carboxylic acid (0.37 grams, 1.46 mmole) and carbonyldiimidazole (0.28 grams, 1.72 mmole) in dichloromethane (15 mL) was stirred for 3 hours at room temperature. Then added a solution of tert-butyl 4-aminomethyl-4-hydroxy piperidine-1-carboxylate (0.4 grams, 1.73 mmole) in dichloromethane (10 ml). The reaction mass was stirred over night (12 hours) at RT under nitrogen atmosphere, while monitoring the progress of the reaction by TLC. After completion of the reaction (TLC), the reaction mass was washed with chilled water (10 mL), brine solution (10 mL) and dried over anhydrous sodium sulfate. The organic phase was concentrated on rotavacuum to afford the title compound.

Yield: 0.68 grams (100%).

$^1$H-NMR (δ ppm): 1.46-1.72 (11H, m), 2.60-2.65 (2H, m), 3.17-3.23 (2H, m), 3.66-3.85 (4H, m), 7.70-7.73 (1H, m), 8.16-8.19 (1H, m), 8.93 (1H, s), 9.05-9.07 (1H, m), 11.23-11.27 (1H, t);

Mass (m/z): 465.1 (M+H)$^+$, 467.1 (M+H)$^+$.

Step (iii): Preparation of 5-Amino-6-chloro-N-{[4-hydroxy-1-(t-butoxycarbonyl)-4-piperidinyl]methyl}quinoline-8-carboxamide

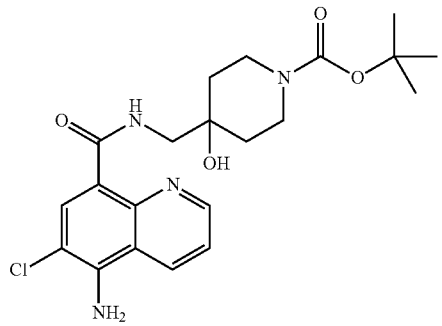 [SMILES: CC(C)(C)OC(=O)N1CCC(O)(CNC(=O)c2cc(Cl)c(N)c3cccnc23)CC1]

Added iron powder (0.34 grams, 6.08 mmole) and ammonium chloride (0.34 grams, 6.35 mmole) to a solution of 6-chloro-5-nitro-N-{[4-hydroxy-1-(tert-butoxycarbonyl)-4-piperidinyl] methyl}quinoline-8-carboxamide (0.7 grams, 1.46 mmole) in ethanol (14 mL), tetrahydrofuran (7 mL) and water (3.5 mL) mixture. The reaction mass was stirred for 6 hours at 75° C., while monitoring the progress of the reaction by TLC. After completion of the reaction (TLC), the reaction mass was cooled to room temperature and filtered through celite bed. The filtrate was concentrated, the slurry, thus obtained, was partitioned between ethyl acetate (25 mL) and water (10 mL) by stirring for 30 minutes. Both the layers were separated and the aqueous phase was extracted with ethyl acetate (3×5 mL). The combined organic phase was washed with water (15 mL), brine solution (15 mL) and dried over sodium sulphate. The organic phase was concentrated under vacuum, and the crude residue, thus obtained, was further purified by flash chromatography using ethyl acetate:n-hexane (50:50) to afford the title compound.

Yield: 0.50 grams (78.61%).

$^1$H-NMR (δ ppm): 1.29-1.49 (13H, m), 3.06-3.10 (2H, m), 3.42-3.46 (2H, m), 3.60-3.63 (2H, m). 4.76 (1H, s), 6.92 (2H, bs). 7.55-7.58 (1H, m) 8.39 (1H, s). 8.83-8.92 (2H, m) 10.97-11.00 (1H, t);

Mass (m/z): 435.2 (M+H)$^+$, 437.2 (M+H)$^+$.

Step (iv): Preparation of 5-Amino-6-chloro-N-[4-hydroxy-(4-piperidinyl)methyl]quinoline-8-carboxamide Ethanolic hydrogen chloride (30% w/w, 0.05 gram, 1.72 mmole) was added to a solution of 5-amino-6-chloro-N-{[4-hydroxy-1-(t-butoxycarbonyl)-4-piperidinyl]methyl}quinoline-8-carboxamide (0.25 gram, 0.57 mmole) in dichloromethane (10 mL) at 10° C. The reaction mass was stirred for 2 hours at room temperature, while monitoring the progress of the reaction by TLC. After completion of the reaction (TLC), the reaction mass was concentrated and the slurry, thus obtained, was dissolved in chilled water (15 mL). The pH was adjusted to ~9.5 using aqueous ammonia solution and the product was extracted with dichloromethane (3×10 mL). The combined organic phase was washed with water (10 mL), brine solution (10 mL) and dried over sodium sulfate. The organic phase was concentrated under vacuum to afford the title compound.

Yield: 0.17 grams (87%).

$^1$H-NMR (δ ppm): 1.19-1.22 (2H, m), 1.34 (2H, s), 2.71-2.74 (2H, m), 2.78-2.84 (2H, m), 3.15 (1H, s), 3.40-3.42 (2H, m), 4.08-4.11 (1H, m), 6.91 (2H, bs), 7.55-7.58 (1H, dd; J=8.56, 4.16 Hz), 8.39 (1H, s), 8.84-8.86 (1H, m), 8.91-8.92 (1H, m), 10.96-10.99 (1H, t);

Mass (m/z): 335.1 (M+H)$^+$, 337.4 (M+H)$^+$.

Preparation 7: Preparation of 2,2-dimethyl-3-methoxy propyl toluene-4-sulfonate

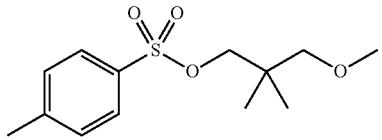

Step (i): Preparation of 2,2-dimethyl-3-methoxy propan-1-ol

A solution of 2,2-dimethyl propane-1,3-diol (10 grams, 0.096 mole) in tetrahydrofuran (40 mL) was added to a stirred solution of NaH (60%, 3.84 grams, 0.160 mole) in tetrahydrofuran (60 mL) drop wise at 0° C. Then reaction mass was slowly heated to 80° C. and stirred for 1 hour. The reaction mixture was cooled to room temperature and added methyliodide (15 grams, 0.105 mole). The reaction mass was stirred over night (20 hours) at room temperature under nitrogen atmosphere, while monitoring the progress of the reaction by TLC. After completion of the reaction (TLC), the reaction mass was poured onto chilled water (100 mL) and the product was extracted with diethyl ether (3×100 mL). The combined organic phase was washed with water (100 mL), brine solution (100 mL) and dried over sodium sulfate. The organic phase was concentrated under vacuum to obtain a crude residue, which was further purified by flash chromatography using methanol:chloroform (1.5:98.5) to afford the title compound.

Yield: 6.5 grams (57.52%).

$^1$H-NMR (δ ppm): 0.90 (6H, s), 2.66-2.68 (1H, t), 3.23 (2H, s), 3.33 (3H, s), 3.42-3.43 (2H, d);

Mass (m/z): 119.4 (M+H)$^+$.

Step (ii): Preparation of 2,2-dimethyl-3-methoxy propyl toluene-4-sulfonate p-Toluene sulfonyl chloride (3.74 grains, 0.019 mole) was added to a stirred solution of 2,2-dimethyl-3-methoxy propan-1-ol (2.0 grams, 0.160 mole) in pyridine (60 mL) portion wise at 0° C. The reaction mass was stirred over night (20 hours) at room temperature under nitrogen atmosphere, while monitoring the progress of the reaction by TLC. After completion of the reaction (TLC), the reaction mass was poured onto chilled IN solution of aqueous HCl (60 mL) and the product was extracted with diethyl ether (3×50 mL). The combined organic phase was washed with water (40 mL), brine solution (40 mL) and dried over sodium sulphate. The organic phase was concentrated under vacuum to afford the title compound.

Yield: 4.25 grams (92.19%).

$^1$H-NMR (δ ppm): 0.87 (6H, s), 2.44 (3H, s), 3.06 (2H, s), 3.22 (3H, s), 3.78 (2H, s), 7.33-7.35 (2H, d, J=8.00 Hz), 7.77-7.79 (2H, d, J=8.00 Hz);

Mass (m/z): 273.2 (M+H)$^+$.

Preparation 8: Preparation of 2-methoxy-2-methyl propyl toluene-4-sulfonate

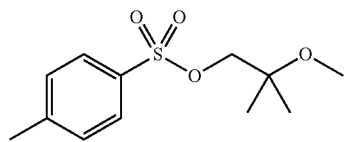

Step (i): Preparation of 2-methoxy-2-methyl propan-1-ol

A solution of isobutyleneoxide (1.0 grams, 13.888 mmole) and indium chloride (0.61 grams, 2.757 mmole) in methanol (20 mL) was stirred at 50° C. for 5 hours while monitoring the progress of the reaction by TLC. After completion of the reaction (TLC), the reaction mass was concentrated under vacuum and the residue was dissolved in dichloromethane (50 mL). The organic phase was washed with saturated sodium bicarbonate solution (10 mL) and dried over sodium sulfate. The organic phase was concentrated under vacuum to afford the title compound.

Yield: 0.18 grams (12.5%).

$^1$H-NMR (δ ppm): 1.16 (6H, s), 1.94-1.97 (1H, t), 3.23 (3H, s), 3.42-3.44 (2H, d);

Mass (m/z): 105.1 (M+H)$^+$.

Step (ii): Preparation of 2-methoxy-2-methyl propyl toluene-4-sulfonate p-Toluene sulfonyl chloride (0.36 grams. 1.889 mmole) was added to a stirred solution of 2-methoxy-2-methyl propan-1-ol (0.18 grams, 1.73 mmole) in pyridine (2 mL) portion wise at 0° C. The reaction mass was stirred for 48 hours at room temperature under nitrogen atmosphere, while monitoring the progress of the reaction by TLC. After completion of the reaction (TLC), the reaction mass was poured onto chilled 1 N solution of aqueous HCl (10 mL) and the product was extracted with ethyl acetate (3×5 mL). The combined organic phase was washed with water (5 mL), brine solution (5 mL) and dried over sodium sulfate. The organic phase was concentrated under vacuum to afford the title compound.

Yield: 0.26 grams (12.5%).

$^1$H-NMR (δ ppm): 1.13 (6H, s), 2.45 (3H, s), 3.14 (3H, s), 3.85 (2H, s), 7.33-7.35 (2H, d, J=8.00 Hz), 7.79-7.81 (2H, d, J=8.00 Hz);

Mass (m/z): 259.2 (M+H)$^+$.

EXAMPLES

The novel compounds of the present invention were prepared according to the following experimental procedures, using appropriate materials and conditions.

Example 1

Preparation of 5-Amino-6-chloro-N-{[1-(tetrahydro-2H-pyran-4-ylmethyl)-4-piperidinyl]methyl}quinoline-8-carboxamide hemifumarate

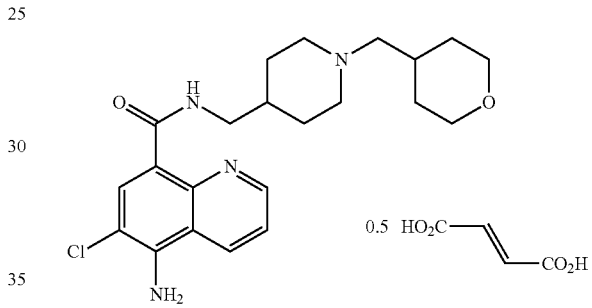

Step (i): Preparation of 5-Amino-6-chloro-N-{[1-(tetrahydro-2H-pyran-4-ylmethyl)-4-piperidinyl]methyl}quinoline-8-carboxamide

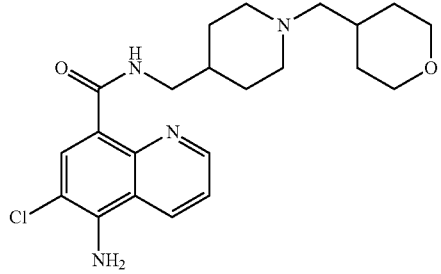

A solution of 5-amino-6-chloro-N-[(4-piperidinyl)methyl] quinoline-8-carboxamide (5.60 grams, 0.017 mole, obtained from preparation 2) and tetrahydro pyran-4-carboxaldehyde (2.40 grams, 0.021 mole) in dichloroethane (70 mL) was cooled to 10° C. Sodium triacetoxyborohydride (7.45 grams, 0.035 mole) was added to the above reaction mass. It was further stirred overnight at RT, while monitoring the progress of the reaction by TLC. After completion of the reaction (TLC), the reaction mass was concentrated and the slurry, thus obtained, was quenched onto water (150 mL). The pH of the resulting mass was adjusted to ~9.5 using aqueous ammonia solution and the product was extracted with DCM (3×100 mL). The combined organic phase was washed with water (100 mL), brine solution (100 mL) and dried over sodium sulphate. The organic phase was concentrated under vacuum to obtain a crude residue, which was further purified by flash chromatography using triethylamine: methanol:chloroform (0.5:2:97.5) to afford the title compound.

Yield: 5.80 grams (80%).

$^1$H-NMR (δ ppm): 1.21-1.30 (2H, m), 1.39-1.41 (2H, m), 1.64-1.74 (3H, m), 1.78-1.81 (3H, m), 1.89-1.94 (2H, m), 2.15-2.17 (2H, m), 2.86-2.89 (2H, m), 3.34-3.40 (2H, m), 3.45-3.48 (2H, m), 3.93-3.96 (2H, m), 4.98 (2H, s), 7.43-7.46 (1H, m), 8.76 (1H, s), 8.76-8.81 (1H, dd, J=8.64, 1.32 Hz), 8.87-8.90 (1H, m), 11.06-11.10 (1H, t);

Mass (m/z): 417.4 (M+H)$^+$, 419.2 (M+H)$^+$.

Step (ii): Preparation of 5-Amino-6-chloro-A-{[1-(tetrahydro-2H-pyran-4-ylmethyl)-4-piperidinyl] methyl}quinoline-8-carboxamide hemifumarate A solution of 5-amino-6-chloro-N-{[1-(tetrahydro-2H-pyran-4-ylmethyl)-4-piperidinyl]methyl}quinoline-8-carboxamide (35.0 grams, 0.083 moles, obtained in above step) in ethanol (105 mL) was heated at 80° C. under stirring for 10 minutes to obtain a clear solution. Fumaric acid (6.82 grams, 0.058 moles) solution in ethanol (140 mL) was added slowly at 80° C. During addition solids formation was observed. After completion of addition (~10 minutes), the mass was stirred further for 30 minutes at 80° C. The mass was allowed to cool to RT on its own and then cooled further to 10° C. using ice bath. After 30 minutes the solid mass was filtered under vacuum. The solid mass, thus obtained, was washed with chilled diethylether (140 mL) and dried under vacuum to afford the title compound.

Yield: 34.49 grams (86.5%).

$^1$H-NMR (δ ppm): 1.04-1.07 (2H, m), 1.23-1.31 (2H, m), 1.51-1.54 (3H, m), 1.64-1.69 (3H, m), 1.90-2.00 (2H, m), 2.19-2.22 (2H, m), 2.89-2.93 (2H, m), 3.18-3.30 (4H, m), 3.74-3.79 (2H, m), 6.50 (1H, s), 6.89 (2H, s). 7.51-7.54 (1H, m), 8.35 (1H, s), 8.76-8.81 (1H, dd, j=8.60, 0.76 Hz). 8.87-8.90 (1H, m), 10.85-10.88 (1H, t):

Mass (m/z): 417.4 (M+H)$^+$, 419.2 (M+H)$^+$.

Example 2

Preparation of 5-Amino-6-chloro-N-{[3-(tetrahydro-2H-pyran-4-ylmethyl)-3-azabicyclo[3.1.0]hex-6-yl]methyl}quinoline-8-carboxamide L(+)-tartarate

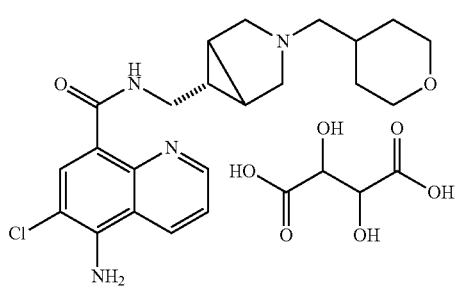

Step (i): Preparation of 5-Amino-6-chloro-N-{[3-(tetrahydro-2H-pyran-4-ylmethyl)-3-azabicyclo [3.1.0]hex-6-yl]methyl}quinoline-8-carboxamide

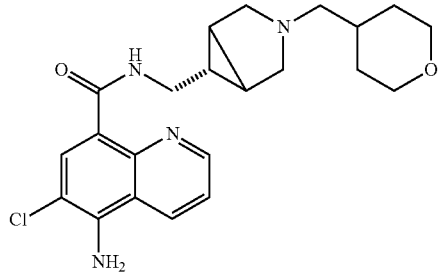

A solution of 5-amino-6-chloro-N-{[3-azabicyclo[3.1.0]hex-6-yl]methyl}quinoline-8-carboxamide (0.30 gram, 0.947 mmole, obtained from preparation 4) and tetrahydro pyran-4-carboxaldehyde (0.14 gram, 1.228 mmole) in dichloroethane (30 mL) was cooled to 10° C. and treated with sodium triacetoxyborohydride (0.40 gram, 1.886 mmole). The reaction mass was stirred over night at RT, while monitoring the progress of the reaction by TLC. After completion of the reaction (TLC), the reaction mass was poured onto water (40 mL). The pH of the resulting mass was adjusted to ~9.5 with aqueous ammonia solution and the product was extracted with DCM (3×25 mL). The combined organic phase was washed with water (25 mL), brine solution (25 mL) and dried over sodium sulphate. The organic phase was concentrated under vacuum to obtain a crude residue, which was further purified by flash chromatography using triethylamine:methanol:chloroform (0.5:2:97.5) to afford the title compound.

Yield: 0.23 gram (59%).

$^1$H-NMR (δ ppm): 1.29-1.36 (2H, m), 1.58-1.65 (1H, m), 1.69-1.73 (2H, m), 1.94-1.99 (3H, m), 3.04-3.08 (2H, m), 3.34-3.59 (8H, m), 3.93-3.98 (2H, m), 7.53-7.56 (1H, m), 8.54 (1H, s), 8.70-8.72 (1H, m), 8.95-8.97 (1H, m);

Mass (m/z): 415.4 (M+H)$^+$, 417.3 (M+H)$^+$.

Step (ii): Preparation of 5-Amino-6-chloro-N-{[3-(tetrahydro-2H-pyran-4-ylmethyl)-3-azabicyclo [3.1.0]hex-6-yl]methyl}quinoline-8-carboxamide L(+)-tartarate A solution of L(+)-tartaric acid (0.08 gram, 0.554 mole) in 5 mL methanol was added to a stirred solution of 5-amino-6-chloro-N-{[3-(tetrahydro-2H-pyran-4-ylmethyl)-3-azabicyclo[3.1.0]hex-6-yl]methyl}quinoline-8-carboxamide (0.23 gram, 0.554 mole, obtained in above step) in methanol (20 mL). The clear mass, thus obtained, was stirred further for 2 hours at RT. The solvent was evaporated to afford solid mass. The solid mass was triturated with diethyl ether (20 mL) and dried under reduced pressure to obtain the title compound.

Yield: 0.26 gram (85%).

$^1$H-NMR (δ ppm): 1.27-1.37 (2H, m), 1.59-1.64 (1H, m), 1.67-1.70 (2H, m), 1.95-1.99 (3H, m), 3.03-3.05 (2H, m), 3.35-3.56 (8H, m), 3.92-3.96 (2H, m), 4.46 (2H, s), 7.54-7.57 (1H, m), 8.52 (1H, s), 8.69-8.71 (1H, m), 8.94-8.95 (1H, m);

Mass (m z): 415.4 (M+H), 417.3 (M+H)$^+$.

Examples 3 to 19

The compounds of Examples 3 to 19 were prepared by following the experimental procedures as described in the Examples 1 to 2 given above, with some noncritical variations.

| Example Number | Chemical name and Structure | Characterization data |
| --- | --- | --- |
| 3. | 5-Amino-6-chloro-N-[1-(tetrahydro-2H-pyran-4-ylmethyl)-4-piperidinyl]quinoline-8-carboxamide | ¹H-NMR (δ ppm): 1.24-1.28 (2H, m), 1.33-1.37 (2H, m), 1.51-1.58 (4H, m), 1.84-1.91 (3H, m), 3.28 (1H, m), 2.44-2.50 (2H, m), 3.53-3.88 (6H, m), 6.81 (2H, bs), 7.54-7.58 (1H, m), 8.28 (1H, s), 8.83-8.86 (1H, m), 8.94-8.96 (1H, m), 10.91-10.93 (1H, d); Mass (m/z): 403.1 (M + H)⁺, 405.2 (M + H)⁺. |
| 4. | (R,S) 5-Amino-6-chloro-N-{[1-(tetrahydro-3-furanylmethyl)-4-piperidinyl]methyl}quinoline-8-carboxamide L(+)-tartarate | ¹H-NMR (δ ppm): 1.66-1.73 (3H, m), 2.05-2.09 (3H, m), 2.20-2.22 (1H, m), 2.68-2.71 (1H, m), 2.98-3.01 (2H, m), 3.15-3.17 (2H, m), 3.46-3.60 (5H, m), 3.75-3.77 (1H, m), 3.87-3.96 (2H, m), 4.43 (2H, s), 7.53-7.56 (1H, m), 8.51 (1H, s), 8.68-8.70 (1H dd, J = 7.30, 1.31 Hz), 8.92-8.93 (1H, m); Mass (m/z): 403.2 (M + H)⁺, 405.1 (M + H)⁺. |
| 5. | (R,S) 5-Amino-6-chloro-N-{[1-(tetrahydro-2-furanylmethyl)-4-piperidinyl]methyl}quinoline-8-carboxamide | ¹H-NMR (δ ppm): 1.41-1.50 (3H, m), 1.64-1.75 (6H, m), 1.87-2.00 (4H, m), 2.28-2.31 (2H, m), 2.80-3.01 (2H, m), 3.55-3.57 (1H, m), 3.69-3.78 (1H, m), 3.88-3.91 (1H, m), 6.87 (2H. bs), 7.55-7.58 (1H, m), 8.37 (1H, s), 8.83-8.86 (1H, dd, J = 8.68. 1.40 Hz), 8.93-8.94 (1H, m), 10.88-10.91 (1H, t); Mass (m/z): 403.2 (M + H)⁺, 405.1 (M + H)⁺. |
| 6. | 5-Amino-6-chloro-N-{[1-(tetrahydro-2H-pyran-4-yl)-4-piperidinyl]methyl}quinoline-8-carboxamide L(+)-tartarate | ¹H-NMR (δ ppm): 1.56-1.65 (2H, m), 1.72-1.78 (2H, m), 2.01-2.03 (2H, m), 2.13-2.16 (2H, m), 3.00-3.06 (2H, m), 3.40-3.52 (6H, m), 3.62-3.65 (2H, m), 4.05-4.08 (2H, m), 4.53 (2H, s), 7.55-7.58 (1H, m), 8.53 (1H, s), 8.83-8.86 (1H, dd, J = 8.68, 1.40 Hz), 8.93-8.94 (1H; m); Mass (m/z): 403.1 (M + H)⁺, 405.2 (M + H)⁺. |

-continued

| Example Number | Chemical name and Structure | Characterization data |
|---|---|---|
| 7. | 5-Amino-6-chloro-N-{[3-(tetrahydro-3-furanylmethyl)-3-azabicyclo[3.1.0]hex-6-yl]methyl}quinoline-8-carboxamide | $^1$H-NMR (δ ppm): 0.84-0.87 (1H, m), 0.97-0.98 (1H, m), 1.34-1.37 (2H, m), 1.83-1.89 (2H, m), 2.20-2.30 (5H, m), 2.92-2.98 (2H, m), 3.54-3.56 (2H, m), 3.62-3.67 (3H, m), 6.91 (2H, bs), 7.55-7.58 (1H, m), 8.38 (1H, s), 8.83-8.86 (1H, dd, J = 8.60, 1.20 Hz), 8.95-8.96 (1H, m), 10.86-10.88 (1H, t); Mass (m/z): 401.3 (M + H)$^+$, 403.2 (M + H)$^+$. |
| 8. | 5-Amino-6-chloro-N-{[3-isobutyl-3-azabicyclo[3.1.0]hex-6-yl]methyl}quinoline-8-carboxamide L(+)-tartarate | $^1$H-NMR (δ ppm): 0.97-0.99 (6H, d), 1.26-1.27 (1H, m), 1.54-1.55 (1H, m), 1.89-2.00 (3H, m), 2.95-2.97 (2H, m), 3.11-3.12 (1H, m), 3.28-3.39 (1H, m), 3.45-3.47 (3H, m), 4.42 (2H, s), 7.50-7.53 (1H, m), 8.49 (1H, s), 8.66-8.68 (1H, dd, J = 8.67, 1.49 Hz), 8.90-8.91 (1H, m); Mass (m/z): 373.3 (M + H)$^+$, 375.4 (M + H)$^+$. |
| 9. | 5-Amino-6-chloro-N-{[3-cyclopropylmethyl-3-azabicyclo[3.1.0]hex-6-yl]methyl}quinoline-8-carboxamide L(+)-tartarate | $^1$H-NMR (δ ppm): 0.36-0.38 (2H, m), 0.66-0.70 (2H, m), 1.03-1.08 (2H, m), 1.28-1.30 (1H, m), 1.50-1.55 (1H, m), 3.00-3.02 (2H, m), 3.10-3.11 (1H, m), 3.28-3.48 (3H, m), 3.74-3.75 (2H, m) 4.43 (2H, s), 7.50-7.54 (1H, m), 8.49 (1H, s), 8.66-8.68 (1H, dd, J = 8.67, 1.40 Hz), 8.90-8.92 (1H, m); Mass (m/z): 371.3 (M + H)$^+$, 373.3 (M + H)$^+$. |
| 10. | 5-Amino-6-chloro-N-{[3-isopropyl-3-azabicyclo[3.1.0]hex-6-yl]methyl}quinoline-8-carboxamide L(+)-tartarate | $^1$H-NMR (δ ppm): 1.29-1.31 (6H, d), 1.35-1.40 (1H, m), 1.94-1.96 (2H, m), 3.28-3.32 (3H, m), 3.45-3.46 (2H, m), 3.66-3.69 (2H, m), 4.45 (2H, s), 7.50-7.53 (1H, in), 8.48 (1H, s), 8.65-8.68 (1H, m), 8.91-8.92 (1H, m); Mass (m/z): 359.4 (M + H)$^+$, 361.2 (M + H)$^+$. |

| Example Number | Chemical name and Structure | Characterization data |
|---|---|---|
| 11. | 5-Amino-6-fluoro-N-{[1-(tetrahydro-2H-pyran-4-ylmethyl)-4-piperidinyl]methyl}quinoline-8-carboxamide L(+)-tartarate | $^1$H-NMR (δ ppm): 1.07-1.10 (1H, m), 1.18-1.22 (2H, m), 1.56-1.66 (4H, m), 1.82-1.85 (3H, m), 1.99-2.01 (1H, m), 2.71-2.79 (3H, m), 3.04-3.09 (2H, m), 3.16-3.38 (4H, m), 3.81-3.84 (2H, m), 4.25 (2H, s), 6.76 (2H, bs), 7.54-7.57 (1H, m), 8.28-8.29 (1H, m), 8.82-8.84 (1H, m), 8.93-8.94 (1H, m), 10.99 (1H, bs); Mass (m/z): 401.2 (M + H)$^+$. |
| 12. | 5-Amino-6-chloro-N-{[1-(tetrahydro-2H-pyran-4-ylmethyl)-3-pyrrolidinyl]methyl}quinoline-8-carboxamide L(+)-tartarate | $^1$H-NMR (δ ppm): 1.08-1.14 (2H, m), 1.49-1.64 (4H, m), 1.71-1.78 (1H, m), 1.95-1.98 (1H, m), 2.53-2.60 (2H, m), 2.88-2.98 (2H, m), 3.18-3.25 (2H, m), 3.33-3.43 (4H, m), 3.75-3.80 (2H, m), 4.08 (2H, s), 6.91 (2H, bs), 7.54-7.57 (1H, m), 8.34 (1H, s), 8.81-8.83 (1H, dd, J = 8.68, 0.96 Hz), 8.91-8.92 (1H, m), 10.90-10.93 (1H, t); Mass (m/z): 403.1 (M + H)$^+$, 405.2 (M + H)$^+$. |
| 13. | 5-Amino-6-chloro-N-{[1-(tetrahydro-2H-pyran-4-ylmethyl)-4-piperidinyl]methyl}quinoline-8-carboxamide L(+)-tartarate | $^1$H-NMR (δ ppm): 1.04-1.07 (2H, m), 1.23-1.31 (2H, m), 1.51-1.54 (3H, m), 1.64-1.69 (3H, m), 1.90-2.00 (2H, m), 2.19-2.22 (2H, m), 2.89-2.93 (2H, m), 3.18-3.30 (4H, m), 3.74-3.79 (2H, m), 4.50 (1H, s), 6.89 (2H, s), 7.51-7.54 (1H, m), 8.35 (1H, s), 8.76-8.81 (1H, dd, J = 8.60, 0.76 Hz), 8.87-8.90 (1H, m), 10.85-10.88 (1H, t); Mass (m/z): 417.4 (M + H)$^+$, 419.2 (M + H)$^+$. |
| 14. | (Exo) 5-Amino-6-chloro-N-{[3-(tetrahydro-2H-pyran-4-ylmethyl)-3 azabicyclo[3.1.0]hex-6-yl]methyl}quinoline-8-carboxamide | $^1$H-NMR (δ ppm): 1.21-1.27 (3H, m), 1.31-1.39 (3H, m), 1.49-1.54 (3H, m), 2.11-2.15 (3H, m), 2.88-2.95 (2H, m), 3.16-3.25 (4H, m), 3.71-3.79 (2H, m), 6.88 (2H, 5), 7.53-7.56 (1H, m), 8.35 (1H, s), 8.80-8.83 (1H, m), 8.92-8.93 (1H, m), 10.83 (1H, bs); Mass (m/z): 415.4 (M + H)$^+$, 417.3 (M + H)$^+$. |

| Example Number | Chemical name and Structure | Characterization data |
|---|---|---|
| 15. | 5-Amino-6-chloro-N-{[3-(tetrahydro-2H-pyran-4-ylmethyl)-3-azabicyclo[3.1.0]hex-6-yl]methyl}quinoline-8-carboxamide (exo/endo mixture) | ¹H-NMR (δ ppm): 1.21-1.28 (2H, m), 1.58-1.67 (4H, m), 1.40-1.48 (2H, m), 2.29-2.32 (4H, m), 3.03-3.05 (2H, m), 3.34-3.48 (4H, m), 3.94-3.97 (2H, m), 4.97 (2H, bs), 7.47-7.50 (1H, m), 8.24-8.26 (1H, m), 8.79 (1H, s), 8.93-8.94 (1H, m), 11.00 (1H, bs); Mass (m/z): 415.2 (M + H)⁺, 417.1 (M + H)⁺. |
| 16. | 5-Amino-6-bromo-N-{[1-(tetrahydro-2H-pyran-4-ylmethyl)-4-piperidinyl] methyl}quinoline-8-carboxamide L(+)-tartarate | ¹H-NMR (δ ppm): 1.06-1.17 (2H, m), 1.34-1.41 (2H, m), 1.56-1.83 (6H, m), 2.28-2.44 (4H, m), 3.02-3.07 (2H, m), 3.23-3.34 (4H, m), 3.78-3.82 (2H, m), 4.09 (2H, s), 6.88 (2H, bs), 7.55-7.58 (1H, m), 8.51 (1H, s), 8.85-8.87 (1H, m), 8.94-8.95 (1H, m), 10.88-10.91 (1H, t); Mass (m/z): 461.1 (M + H)⁺; 463.2 (M + H)⁺. |
| 17. | 5-Amino-6-bromo-N-{[3-(tetrahydro-2H-pyran-4-yl methyl)-3-azabicyclo[3.1.0]hex-6-yl]methyl}quinoline-8-carboxamide L(+)-tartarate | ¹H-NMR (δ ppm): 1.00-1.10 (2H, m), 1.40-1.62 (6H, m), 2.35-2.41 (2H, m), 3.04-3.10 (2H, m), 3.19-3.27 (6H, m), 3.75-3.79 (2H, m), 4.19 (2H, s), 6.87 (2H, bs), 7.55-7.58 (1H, dd, J = 8.56, 4.16 Hz), 8.51 (1H, s), 8.85-8.87 (1H, dd, J = 0.88, 7.76 Hz), 8.96 (1H, m), 10.85-10.88 (1H, t); Mass (m/z): 459.4 (M + H)⁺; 461.2 (M + H)⁺. |
| 18. | 5-Amino-6-chloro-N-{[1-(tetrahydro-2-furanylmethyl)-4-piperidinyl]methyl}quinoline-8-carboxamide L(+)-tartarate | ¹H-NMR (δ ppm): 1.29-1.35 (1H,m), 1.55-1.67 (3H, m), 1.93-2.15 (6H, m), 3.05-3.13 (3H, m), 3.51-3.52 (2H, m), 3.66-3.68 (2H, m), 3.81-3.82 (1H, m), 3.92-3.93 (1H, m), 4.27-4.29 (1H, m), 4.43 (2H, s), 7.53-7.56 (1H, dd, J = 8.56, 4.24 Hz), 8.51 (1H, s), 8.68-8.70 (1H, m), 8.92-8.93 (1H, m); Mass (m/z): 403.4 (M + H)⁺; 405.4 (M + H)⁺. |

| Example Number | Chemical name and Structure | Characterization data |
|---|---|---|
| 19. | 5-Amino-6-fluoro-N-{[3-(tetrahydro-2H-pyran-4-yl methyl)-3-azabicyclo[3.1.0]hex-6-yl]methyl}quinoline-8-carboxamide L(+)-tartarate | $^1$H-NMR (δ ppm): 1.02-1.08 (2H, m), 1.17-1.21 (1H, m), 1.32-1.34 (1H, m), 1.46-1.75 (6H, m), 2.50-2.65 (1H, m), 3.15-3.22 (6H, m), 3.77-3.79 (2H, m), 3.98-4.11 (1H, m), 4.24 (2H, s), 6.73 (2H, bs), 7.53-7.56 (1H, dd, J = 8.52; 4.08 Hz), 8.25-8.28 (1H, m), 8.79-8.82 (1H, m), 8.92-8.93 (1H, m), 10.94-10.95 (1H, t); Mass (m/z): 399.5 (M + H)$^+$. |

Example 20

Preparation of 5-Amino-6-chloro-N-{[4-fluoro-1-(tetrahydro-2H-pyran-4-ylmethyl)-4-piperidinyl]methyl}quinoline-8-carboxamide L(+)-tartarate

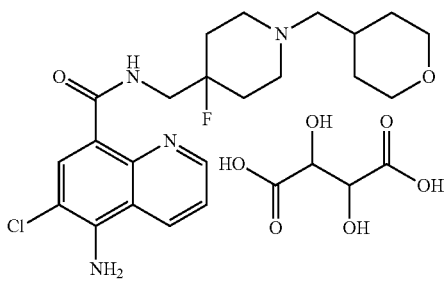

Step (i): Preparation of 5-Amino-6-chloro-N-{[4-fluoro-1-(tetrahydro-2H-pyran-4-ylmethyl)-4-piperidinyl]methyl}quinoline-8-carboxamide

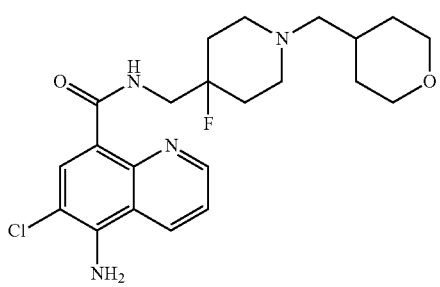

A solution of 5-amino-6-chloro-N-[4-fluoro-(4-piperidinyl)methyl] quinoline-8-carboxamide (0.1 grams, 0.297 mmole, obtained from preparation 5) and tetrahydro pyran-4-carboxaldehyde (0.040 grams, 0.356 mole) in dichloroethane (5 mL) was cooled to 10° C. Sodium triacetoxyborohydride (0.126 grams. 0.594 mmole) was added to the above reaction mass. It was further stirred overnight at RT, while monitoring the progress of the reaction by TLC. After completion of the reaction (TLC), the reaction mass was quenched onto water (10 mL). The pH of the resulting mass was adjusted to ~9.5 using aqueous ammonia solution and the product was extracted with DCM (3×10 mL). The combined organic phase was washed with water (10 mL), brine solution (10 mL) and dried over sodium sulphate. The organic phase was concentrated under vacuum to obtain a crude residue, which was further purified by flash chromatography using triethylamine:methanol:chloroform (0.5:2:97.5) to afford the title compound.

Yield: 0.103 grams (80%).

$^1$H-NMR (δ ppm): 1.25-1.32 (2H, m), 1.63-1.67 (2H, m), 1.75-1.92 (2H, m), 2.21-2.28 (2H, m), 2.33-2.36 (2H, m), 2.62-2.65 (2H, m), 2.99-3.02 (1H, m), 3.36-3.39 (2H, m), 3.65-3.72 (2H, m), 3.76-3.83 (2H, m), 3.93-3.97 (2H, m), 4.99 (2H, s), 7.44-7.47 (1H, dd, J=8.56 Hz; 4.24 Hz), 8.22-8.24 (1H, m), 8.77 (1H, s), 8.90-8.91 (1H, m), 11.27-11.29 (1H, t);

Mass (m/z): 435.3 (M+H)$^+$; 437.4 (M+H)$^+$.

Step (ii): Preparation of 5-Amino-6-chloro-N-{[4-fluoro-1-(tetrahydro-2H-pyran-4-ylmethyl)-4-piperidinyl]methyl}quinoline-8-carboxamide L(+)-tartarate L(+)-tartaric acid (0.034 grams, 0.230 mmole) was added to a solution of 5-amino-6-chloro-N-{[4-fluoro-1-(tetrahydro-2H-pyran-4-ylmethyl)-4-piperidinyl]methyl}quinoline-8-carboxamide (0.1 grams, 0.230 mmole, obtained from above step) in methanol (5 mL) and stirred for 30 minutes at RT. The reaction mass was evaporated under vacuum, the obtained mass was triturated with diethylether (10 mL) and dried under vacuum to afford the title compound.

Yield: 0.12 grams (89%).

$^1$H-NMR (δ ppm): 1.07-1.10 (2H, m), 1.57-1.60 (2H, m), 1.75-1.89 (4H, m), 2.31-2.40 (2H, m), 2.83-2.87 (2H, m), 3.23-3.29 (4H, m), 3.65-3.72 (2H, m), 3.78-3.81 (2H, m), 4.04-4.07 (1H, m), 4.23 (2H, s), 6.98 (2H, bs), 7.56-7.59 (1H, dd, J=8.56 Hz, 4.24 Hz), 8.40 (1H, s), 8.85-8.87 (1H, m), 8.92-8.93 (I H, m). 11.09-11.12 (1H, t);

Mass (m/z): 435.3 (M+H)$^+$; 437.4 (M+H)$^+$.

Example 21

The compound of Example 21 was prepared by following the experimental procedures as described in the Example 20 given above, with some noncritical variations.

| Example Number | Chemical name and Structure | Characterization data |
|---|---|---|
| 21. | (R,S) 5-Amino-6-chloro-N-{[4-fluoro-1-(tetrahydro-3-furanylmethyl)-4-piperidinyl]methyl}quinoline-8-carboxamide L(+)-tartarate | $^1$H-NMR (δ ppm): 1.47-1.50 (1H, m), 1.70-1.73 (1H, m), 1.79-1.81 (3H, s), 1.90-1.93 (1H, m), 2.31-2.40 (4H, m), 2.65-2.78 (2H, m), 3.15-3.21 (1H, m), 3.49-3.70 (6H, m), 4.22 (2H, s), 6.98 (1H, bs), 7.56-7.5.9 (1H, dd, J = 8.40, 4.04 Hz), 8.40 (1H, s), 8.85-8.93 (2H, m), 11.08-11.10 (1H, t); Mass (m/z): 421.3 (M + H)$^+$; 423.3 (M + H)$^+$ |

Example 22

Preparation of 5-Amino-6-chloro-N-{[4-hydroxy-1-(tetrahydro-2H-pyran-4-yl methyl)-4-piperidinyl]methyl}quinoline-8-carboxamide L(+)-tartarate

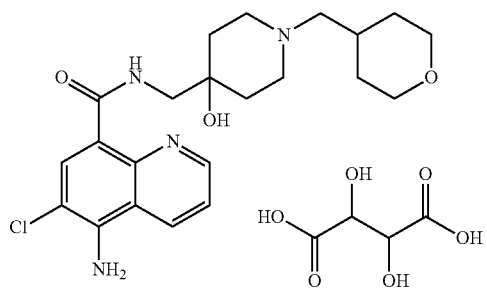 [SMILES: Nc1c(Cl)cc(C(=O)NCC2(O)CCN(CC3CCOCC3)CC2)c2ncccc12 ; O=C(O)C(O)C(O)C(=O)O]

Step (i): Preparation of 5-Amino-6-chloro-N-{[4-hydroxy-1-(tetrahydro-2H-pyran-4-yl methyl)-4-piperidinyl]methyl}quinoline-8-carboxamide

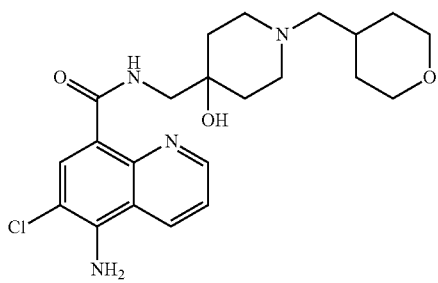 [SMILES: Nc1c(Cl)cc(C(=O)NCC2(O)CCN(CC3CCOCC3)CC2)c2ncccc12]

Sodium cyanoborohydride (0.028 grams, 0.435 mmole) was added to a stirred solution of 5-amino-6-chloro-N-[4-hydroxy-(4-piperidinyl)methyl] quinoline-8-carboxamide (0.1 grams, 0.297 mmole) and tetrahydro pyran-4-carboxaldehyde (0.051 grams, 0.435 mmole) in methanol (5 mL). It was further stirred overnight at room temperature, while monitoring the progress of the reaction by TLC. After completion of the reaction (TLC), the reaction mass was concentrated and the slurry, thus obtained, was quenched onto water (10 mL). The product was extracted with dichloromethane (3×10 mL). The combined organic phase was washed with water (10 mL), brine solution (10 mL) and dried over sodium sulphate. The organic phase was concentrated under vacuum to obtain a crude residue, which was further purified by flash chromatography using triethylamine:methanol:chloroform (0.5:2:97.5) to afford the title compound.

Yield: 0.057 grams (44.18%).
$^1$H-NMR (δ ppm): 1.00-1.11 (2H, m), 1.46-1.56 (4H, m), 1.68-1.69 (1H, m), 2.06-2.10 (2H, m), 2.27-2.29 (2H, m), 2.40-2.12 (2H, m), 3.21-3.33 (1H, m), 3.39-3.10 (2H, m), 3.76-3.80 (2H, m), 4.48 (1H, s), 6.91 (2H, bs), 7.54-7.58 (1H, dd; J=8.52, 4.24 Hz), 8.39 (1H, s), 8.83-8.85 (1H, m), 8.90-8.91 (1H, m), 10.95-10.97 (1H, t);
Mass (m/z): 433.3 (M+H)$^+$, 435.3 (M+H)$^+$.

Step (ii): Preparation of 5-Amino-6-chloro-N-{[4-hydroxy-1-(tetrahydro-2H-pyran-4-yl methyl)-4-piperidinyl]methyl}quinoline-8-carboxamide L(+)-tartarate L(+)-tartaric acid (0.019 grams, 0.126 mmole) was added to a solution of 5-amino-6-chloro-N-{[4-hydroxy-1-(tetrahydro-2H-pyran-4-yl methyl)-4-piperidinyl] methyl}quinoline-8-carboxamide (0.055 grams, 0.127 mmole) in methanol (5 mL) and stirred for 30 minutes at room temperature. The reaction mass was evaporated under vacuum, the residual mass was triturated with diethylether (10 mL) and dried under vacuum to afford the title compound.

Yield: 0.71 grams (95.94%).
$^1$H-NMR (δ ppm): 1.06-1.12 (2H, m), 1.55-1.60 (4H, m), 1.65-1.68 (2H, m), 1.84-1.89 (1H, m), 2.65-2.77 (2H, m), 2.82-2.90 (2H, m), 3.15 (1H, s), 3.22-3.28 (4H, m), 3.44-3.48 (2H, m), 3.78-3.81 (2H, m), 4.05 (2H, s), 6.94 (2H, bs), 7.55-7.59 (1H, dd; J=8.56, 4.16 Hz), 8.39 (1H, s), 8.84-8.86 (1H, m), 8.91-8.92 (1H, m), 10.99-11.02 (1H, t);
Mass (m/z): 433.3 (M+H)$^+$, 435.3 (M+H)$^+$.

Example 23

Preparation of 5-Amino-6-chloro-N-{[1-(4-hydroxytetrahydro-2H-pyran-4-ylmethyl)-4-piperidinyl]methyl}quinoline-8-carboxamide L(+)-tartarate

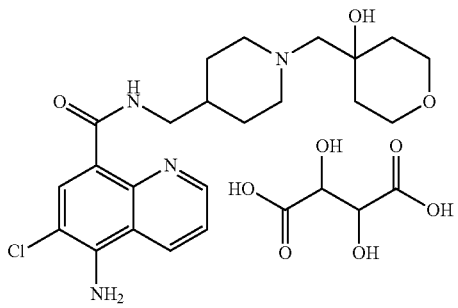

Step (i): Preparation of 5-Amino-6-chloro-N-{[1-(4-hydroxytetrahydro-2H-pyran-4-ylmethyl)-4-piperidinyl]methyl}quinoline-8-carboxamide

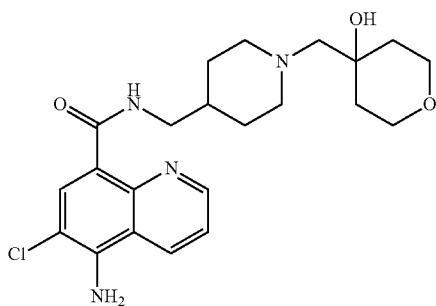 [SMILES: Nc1c(Cl)cc(C(=O)NCC2CCN(CC3(O)CCOCC3)CC2)c2ncccc12]

A solution of 5-amino-6-chloro-N-[(4-piperidinyl)methyl] quinoline-8-carboxamide (3.50 grams, 0.011 mole, obtained from preparation 2), 1,6-dioxa spiro[2.5]octane (2.45 grams, 0.021 mole) and triethylamine (3.25 grams, 0.032 mole) in methanol (35 mL) was stirred overnight at 78° C., while monitoring the progress of the reaction by TLC. After completion of the reaction (TLC), the reaction mass was concentrated and the crude residual mass, thus obtained, was further purified by flash chromatography using methanol:triethylamine:chloroform (5:2:93) to afford the title compound.

Yield: 3.30 grams (80%).

$^1$H-NMR (δ ppm): 1.65-1.68 (2H, m), 1.71-1.81 (4H, m), 2.03-2.06 (3H, m), 3.14-3.19 (4H, m), 3.53-3.58 (3H, m), 3.61-3.65 (2H, m), 3.73-3.78 (3H, m), 7.52-7.57 (1H, m), 8.53 (1H, s), 8.65-8.70 (1H, dd, J=8.60, 1.48 Hz), 8.93-8.94 (1H, m);

Mass (m/z): 433.3 (M+H)$^+$, 435.2 (M+H)$^+$.

Step (ii): Preparation of 5-Amino-6-chloro-N-{[1-(4-hydroxytetrahydro-2H-pyran-4-ylmethyl)-4-piperidinyl]methyl}quinoline-8-carboxamide L(+)-tartarate A clear solution of L(+)-tartaric acid (0.09 gram, 0.600 mole) in 5 mL methanol was 3 added to a stirred solution of 5-amino-6-chloro-N-{[1-(4-hydroxytetrahydro-2H-pyran-4-ylmethyl)-4-piperidinyl]methyl}quinoline-8-carboxamide (0.26 gram, 0.6 mmole, obtained in above step) in methanol (20 mL) and DCM (5 mL) at RT. The clear mass was stirred further for 2 hours at RT. The solvent was evaporated to afford solid mass. The solid mass was further triturated with diethyl ether (2×5 mL) and dried under reduced pressure to obtain the title compound.

Yield: 0.32 gram (91%).

$^1$H-NMR (δ ppm): 1.64-1.67 (2H, m), 1.70-1.81 (4H, m), 2.01-2.04 (3H, m), 3.13-2.17 (4H; m), 3.51-3.53 (3H, m), 3.62-3.65 (2H, m), 3.72-3.79 (3H, m), 4.47 (2H, s), 7.53-7.56 (1H, m), 8.51 (1H, s), 8.68-8.71 (1H, dd, J=8.62, 1.44 Hz), 8.92-8.93 (1H, m);

Mass (m/z): 433.3 (M+H)$^+$, 435.2 (M+H)$^+$.

Examples 24 to 28

The compounds of Examples 24 to 28 were prepared by following the experimental procedure as described in the Example 23 given above, with some noncritical variations.

| Example Number | Chemical name and Structure | Characterization data |
|---|---|---|
| 24. | 5-Amino-6-chloro-N-[1-(4-hydroxytetrahydro-2H-pyran-4-ylmethyl)-4-piperidinyl] quinoline-8-carboxamide | $^1$H-NMR (δ ppm): 1.22-1.26 (2H, m), 1.31-1.34 (2H, m), 1.51-1.56 (4H, m),1.83-1.89 (2H, m), 2.24-3.26 (1H, m), 2.46-2.48 (2H, m), 3.54-3.85 (6H, m), 4.09-4.11 (1H, m), 6.88 (2H, bs), 7.53-7.56 (1H, m), 8.34 (1H, s), 8.80-8.83 (1H, m), 8.92-8.93 (1H, m), 10.92-10.93 (1H, d); Mass (m/z): 419.2 (M + H)$^+$. 421.3 (M + H)$^+$. |

-continued

| Example Number | Chemical name and Structure | Characterization data |
|---|---|---|
| 25. | 5-Amino-6-chloro-N-{[3-(4-hydroxytetrahydro-2H-pyran-4-ylmethyl)-3-azabicyclo[3.1.0]hex-6-yl]methyl}quinoline-8-carboxamide L(+)-tartarate | $^1$H-NMR (δ ppm): 1.27-1.38 (4H, m), 1.54-1.57 (2H, m), 1.63-1.71 (4H, m), 1.90-1.91 (2H, m), 3.13-3.15 (1H, m), 3.46-3.52 (3H, m), 3.72-3.77 (3H, m), 4.45 (2H, s), 7.53-7.56 (1H, m), 8.52 (1H, s), 8.68-8.70 (1H, m), 8.93 (1H, m); Mass (m/z): 431.4 (M + H)$^+$, 433.3 (M + H)$^+$. |
| 26. | 5-Amino-6-chloro-N-{[1-(4-hydroxytetrahydro-2H-pyran-4-ylmethyl)-4-piperidinyl]methyl}quinoline-8-carboxamide | $^1$H-NMR (δ ppm): 1.23-1.29 (4H, m), 1.46-1.64 (5H, m), 2.07-2.12 (2H, m), 2.20 (2H, m), 2.87-2.90 (2H, m), 3.27-3.34 (2H, m), 3.52-3.61 (4H, m), 4.06 (1H, bs), 6.90 (2H, s), 7.54-7.57 (1H, m), 8.37 (1H, s), 8.83-8.85 (1H, m), 8.93-8.93 (1H, m), 10.87-10.90 (1H, t); Mass (m/z): 433.2 (M + H)$^+$, 435.2 (M + H)$^+$. |
| 27. | 5-Amino-6-chloro-N-{[4-fluoro-1-(4-hydroxytetrahydro-2H-pyran-4-ylmethyl)-4-piperidinyl]methyl}quinoline-8-carboxamide L(+)-tartarate | $^1$H-NMR (δ ppm): 1.35-1.38 (2H, m), 1.52-1.57 (2H, m), 1.74-1.82 (4H, s), 2.35-2.39 (2H, m), 2.51-2.57 (3H, m), 2.80-2.85 (3H, m), 3.59-3.70 (6H, m), 4.22 (2H, 2), 6.97 (1H, s), 7.56-7.57 (1H, dd, J = 8.60; 4.24 Hz), 8.40 (1H, s), 8.85-8.93 (2H, m), 11.08-11.11 (1H, t); Mass (m/z): 451.3 (M + H)$^+$; 453.4 (M + H)$^+$. |
| 28. | 5-Amino-6-fluoro-N-{1-(4-hydroxytetrahydro-2H-pyran-4-ylmethyl)-4-piperidinyl]methyl}quinoline-8-carboxamide L(+)-tartarate | $^1$H-NMR (δ ppm): 1.29-1.32 (4H, m), 1.52-1.64 (4H, m), 2.07-2.20 (4H, m), 2.88-2.91 (2H, m); 3.56-3.61 (5H, m), 4.01-4.10 (1H, m), 4.24 (2H, s), 6.70 (2H, s), 7.51-7.55 (1H, dd, J = 8.44, 4.04 Hz), 8.24-8.30 (1H, m), 8.79-8.91 (2H, m), 10.94-10.96 (1H, t); Mass (m/z): 417.4 (M + H)$^+$. |

Example 29

Preparation of 5-Amino-6-chloro-N-{[4-hydroxy-1-(4-hydroxy tetrahydro-2H-pyran-4-yl methyl)-4-piperidinyl]methyl}quinoline-8-carboxamide L(+)-tartarate

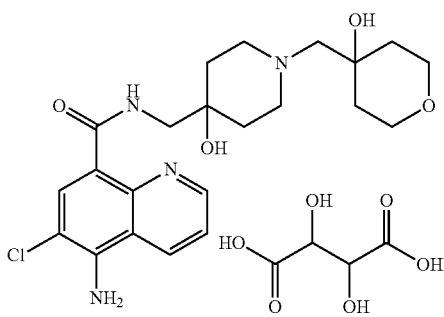

Step (i): Preparation of 5-Amino-6-chloro-N-{[4-hydroxy-1-(4-hydroxy tetrahydro-2H-pyran-4-yl methyl)-4-piperidinyl]methyl}quinoline-8-carboxamide

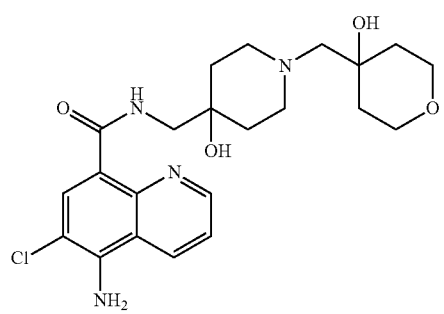 [SMILES: Nc1c(Cl)cc(C(=O)NCC2(O)CCN(CC3(O)CCOCC3)CC2)c2ncccc12]

A solution of 5-amino-6-chloro-N-[4-hydroxy-(4-piperidinyl)methyl] quinoline-8-carboxamide (0.03 grams, 0.089 mmole, obtained from preparation 6), 1,6-Dioxa spiro[2.5] octane (0.02 grams, 0.179 mmole) and triethylamine (0.027 grams, 0.269 mmole) in methanol (5 mL) was stirred for 9 hours at 78° C., while monitoring the progress of the reaction by TLC. After completion of the reaction (TLC), the reaction mass was concentrated and the residual mass, thus obtained, was further purified by flash chromatography using methanol:triethylamine: chloroform (5:0.5:94.5) to afford the title compound.

Yield: 0.029 grams (72.5%).

$^1$H-NMR (δ ppm): 1.36-1.41 (2H, m), 1.52-1.59 (4H, m), 1.72-1.79 (2H, m), 2.84-2.88 (4H, m), 3.16 (2H, s), 3.42-3.44 (2H, m), 3.51-3.65 (4H, m), 4.11 (2H, s), 6.91 (2H, bs), 7.54-7.57 (1H, dd; J=8.60, 4.20 Hz), 8.41 (1H, s), 8.83-8.86 (1H, m), 8.90-8.92 (1H, m), 10.99-11.02 (1H, t);

Mass (m/z): 449.4 (M+H)$^+$, 451.3 (M+H)$^+$.

Step (ii): Preparation of 5-Amino-6-chloro-N-{[4-hydroxy-1-(4-hydroxy tetrahydro-2H-pyran-4-ylmethyl)-4-piperidinyl]methyl}quinoline-8-carboxamide L(+)-tartarate L(+)-tartaric acid (0.010 grams, 0.066 mmole) was added to a solution of 5-amino-6-chloro-N-{[4-hydroxy-1-(4-hydroxy tetrahydro-2H-pyran-4-yl methyl)-4-piperidinyl]methyl}quinoline-8-carboxamide (0.029 grams, 0.064 mmole, obtained in the above step) in methanol (5 mL) and stirred for 30 minutes at room temperature. The reaction mass was evaporated under vacuum and the residual mass was triturated with diethylether (10 mL) and dried under vacuum to afford the title compound.

Yield: 0.037 grams (95.86%).

$^1$H-NMR (δ ppm): 1.37-1.41 (2H, m), 1.53-1.60 (4H, m), 1.71-1.79 (2H, m), 2.83-2.87 (4H, m), 3.15 (2H, s), 3.43-3.44 (2H, m), 3.52-3.65 (6H, m), 4.10 (2H, s), 6.92 (2H, bs), 7.55-7.58 (1H, dd; J=8.62, 4.20 Hz), 8.40 (1H, s), 8.84-8.86 (1H, m), 8.91-8.92 (1H, m), 10.98-11.00 (1H, t);

Mass (m/z): 449.4 (M+H)$^+$, 451.3 (M+H)$^+$.

Example 30

Preparation of 5-Amino-6-chloro-N-{[1-(4-fluoro-tetrahydro-2-pyran-4-ylmethyl)-4-piperidinyl]methyl}quinoline-8-carboxamide L(+)tartarate

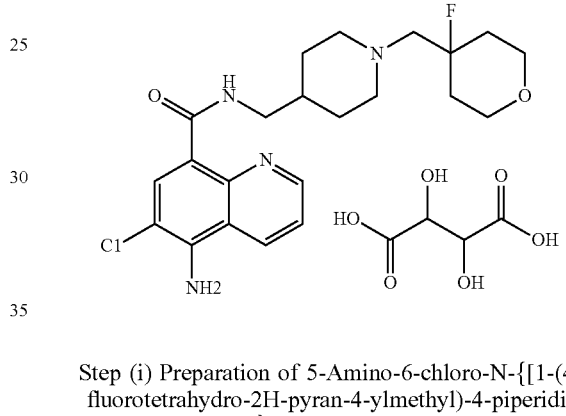

Step (i) Preparation of 5-Amino-6-chloro-N-{[1-(4-fluorotetrahydro-2H-pyran-4-ylmethyl)-4-piperidinyl]methyl}quinoline-8-carboxamide

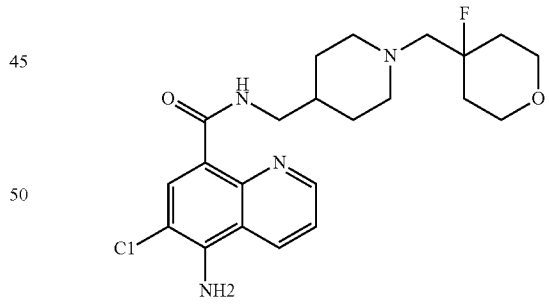

DAST (0.15 grams, 0.924 mmole) was added to a stirred solution of 5-amino-6-chloro-N-{[1-(4-hydroxytetrahydro-2H-pyran-4-ylmethyl)-4-piperidinyl]methyl}quinoline-8-carboxamide (0.2 grams, 0.462 mmole, obtained from the step (i) of Example 23) in DCM (10 mL) at −30° C. Then reaction mass temperature was slowly raised to room temperature and stirred for over night at same temperature. The progress of the reaction was monitored by thin layer chromatography. After completion of the reaction (thin layer chromatography), the mass was quenched in chilled water (10 mL). The mass pH was adjusted to pH 9.5 using aqueous ammonia, the compound was extracted with DGM (3×5 mL). The combined organic phase was washed with water (5 mL), brine solution (5 mL) and dried over sodium sulphate. The organic phase was concentrated on rotavacuum to obtain the crude residue, which was further purified by flash chromatography using TEA:methanol:chloroform (0.5:2:97.5) to afford the title compound.

Yield: 0.052 grams (52%).

$^1$H-NMR (δ ppm): 1.39-1.48 (2H, m), 1.64-1.71 (2H, m), 1.78-1.85 (6H, m), 2.16-2.21 (2H, m), 2.94-2.97 (2H, m), 3.47-3.51 (2H, m), 3.71-3.81 (3H, m), 4.97 (2H, bs), 7.47-7.50 (1H, m), 8.24-8.27 (1H, dd, J=8.56, 1.48 Hz), 8.80 (1H, s), 8.91-8.92 (1H, m), 11.08-11.11 (1H, t);

Mass (m/z): 435.2 (M+H)$^+$, 437.4 (M+H)$^+$.

Step (ii): Preparation of 5-Amino-6-chloro-N-{[1-(4-fluorotetrahydro-2H-pyran-4-ylmethyl)-4-piperidinyl]methyl}quinoline-8-carboxamide L(+)-tartarate A clear solution of L(+)-tartaric acid (0.010 gram, 0.069 mole) in 1 mL methanol was added to a stirred solution of 5-amino-6-chloro-N-{[1-(4-fluorotetrahydro-2H-pyran-4-ylmethyl)-4-piperidinyl]methyl}quinoline-8-carboxamide (0.03 gram, 0.069 mmole, obtained in above step) in methanol (1 mL). The clear mass was stirred further for 2 hours at RT. The solvent was evaporated to afford solid mass. The solid mass was further triturated with diethyl ether (2×2 mL) and dried under reduced pressure to obtain the title compound.

Yield: 0.036 gram (88%).

$^1$H-NMR (δ ppm): 1.27-1.34 (2H, m), 1.48-1.58 (1H, m), 1.60-1.73 (6H, m), 2.10-2.16 (2H, m), 2.90-2.93 (2H, m), 3.15-3.20 (4H, m). 3.49-3.55 (2H, m), 3.63-3.66 (2H, m), 4.25 (2H, s), 6.90 (2H, bs), 7.55-7.58 (1H, m), 8.37 (1H, s), 8.83-8.85 (1H, m), 8.93-8.94 (1H, m), 10.88-10.91 (1H, t);

Mass (m/z): 435.2 (M+H)$^+$; 437.2 (M+H)$^+$.

Example 31

Preparation of 5-Amino-6-chloro-N-{[1-(2-methoxy carbonyl-2-methyl propan-1-yl)-4-piperidinyl]methyl}quinoline-8-carboxamide

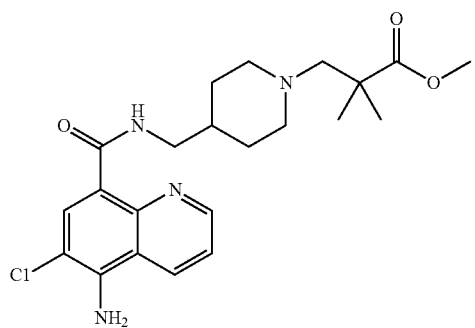

A solution of 5-amino-6-chloro-N-[(4-piperidinyl)methyl] quinoline-8-carboxamide (0.35 grams, 1.09 mmole, obtained from preparation 2) and methyl 2,2-dimethyl-3-oxo propionate (0.3 grams, 2.3 mmole) in dichloroethane (20 mL) was cooled to 10° C. and treated with sodium triacetoxyborohydride (0.58 grams, 2.73 mmole). The reaction mass was stirred overnight at RT, the progress of the reaction was monitored by thin layer chromatography. After completion of the reaction (TLC), the reaction mass was concentrated and the obtained slurry was quenched in water (30 mL). The mass pH was adjusted to ~9.5 using aqueous ammonia, the compound was extracted with DCM (3×10 mL). The combined organic phase was washed with water (15 mL), brine solution (15 mL) and dried over sodium sulphate. The > organic phase was concentrated on rotavacuum to obtain the crude residue, which was further purified by flash chromatography using TEA:methanol:chloroform (0.25:0.75:99) to afford the title compound.

Yield: 0.3 grams (43%).

$^1$H-NMR (δ ppm): 1.05 (6H, s), 1.21-1.28 (3H, m), 1.58-1.61 (2H, m), 2.04-2.10 (2H, m), 2.39-2.47 (2H, m), 2.67-2.70 (2H, m), 3.25-3.28 (2H, m), 3.55 (3H, s), 6.91 (2H, bs), 7.54-7.57 (1H, dd, J=8.56, 4.20 Hz), 8.37 (1H, s), 8.83-8.85 (1H, m), 8.92-8.93 (1H, m), 10.87-10.90 (1H, t);

Mass (m/z): 433.4 (M+H)$^+$; 435.3 (M+H)$^+$.

Example 32

Preparation of 5-Amino-6-chloro-N-{[1-(2,2-dimethyl proponic acid-3-yl)-4-piperidinyl]methyl}quinoline-8-carboxamide L(+)-tartarate

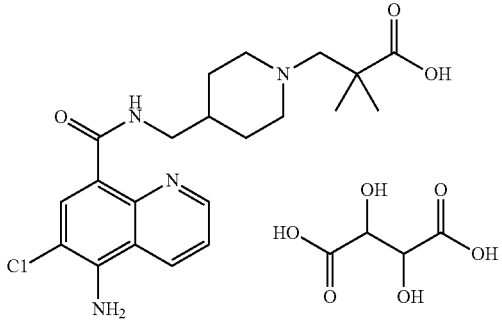

Step (i): Preparation of 5-Amino-6-chloro-N-{[1-(2,2-dimethyl proponic acid-3-yl)-4-piperidinyl]methyl}quinoline-8-carboxamide

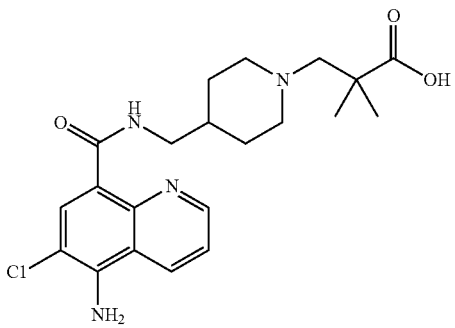

A solution of 5-amino-6-chloro-N-{[1-(2-methoxy carbonyl-2-methyl propan-1-yl)-4-piperidinyl]methyl}quinoline-8-carboxamide (0.092 grams, 0.212 mmole obtained from Example 31) and lithium hydroxide monohydrate (0.044 grams, 1.04 mmole) in methanol (6 mL) and water (2 mL) was stirred overnight at RT, the progress of the reaction was monitored by thin layer chromatography. After completion of the reaction (thin layer chromatography), the reaction mass was concentrated and the obtained slurry was dissolved in DCM (25 mL). The undissolved inorganic solids were separated by filtration. The filtrate was concentrated on rotavacuum to obtain the crude residue, which was further triturated with n-hexane (10 mL) and dried on rotavacuum to afford the title compound.

Yield: 0.059 grams (67%).

$^1$H-NMR (δ ppm): 0.96 (6H, s), 1.21-1.26 (3H, m), 1.61-1.66 (2H, m), 2.02-2.09 (2H, m), 2.35 (2H, s), 2.81-3.85 (2H, m), 3.26-3.30 (3H, m). 6.93 (2H, s) 7.54-7.57 (1H, dd, J=8.62, 4.21 Hz), 8.37 (1H, s), 8.84-8.94 (2H, m), 10.88-10.91 (1H, t);

Mass (m/z): 419.3 (M+H)$^+$; 421.3 (M+H)$^+$.

Step (ii): Preparation of 5-Amino-6-chloro-N-{[1-(2,2-dimethyl proponic acid-3-yl)-4-piperidinyl]methyl}quinoline-8-carboxamide L(+)-tartarate A clear solution of L(+)-tartaric acid (0.019 gram, 0.126 mole) in 2 mL methanol was added to a stirred solution of 5-amino-6-chloro-N-{[1-(2,2-dimethyl proponic acid-3-yl)-4-piperidinyl]methyl}quinoline-8-carboxamide (0.058 gram, 0.138 mmole, obtained in above step) in methanol (2 mL) at RT. The clear mass was stirred further for 2 hours at RT. The solvent was evaporated to afford solid mass. The solid mass was further triturated with diethyl ether (2×3 mL) and dried under reduced pressure to obtain the title compound.

Yield: 0.05 gram (65%).

$^1$H-NMR (δ ppm): 0.99 (6H, s), 1.20-1.25 (3H, m). 1.61-1.64 (2H, m). 2.09-2.14 (2H, m), 2.35 (2H, s), 2.83-3.86 (2H, m), 3.26-3.30 (3H, m), 4.18 (2H, s), 6.91 (2H, s) 7.54-7.57 (1H, dd, J=8.62, 4.21 Hz), 8.37 (1H, s), 8.84-8.94 (2H, m), 10.88-10.91 (1H, t);

Mass (m/z): 419.3 (M+H)$^+$; 421.3 (M+H)$^+$.

Example 33

Preparation of 5-Amino-6-chloro-N-{[1-(3-hydroxy-2,2-dimethyl propyl)-4-piperidinyl]methyl}quinoline-8-carboxamide L(+)-tartarate

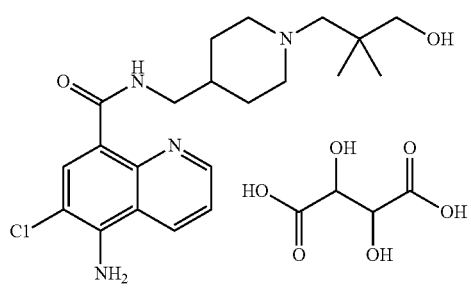

Step (i): Preparation of 5-Amino-6-chloro-N-{[1-(3-hydroxy-2,2-dimethyl propyl)-4-piperidinyl]methyl}quinoline-8-carboxamide

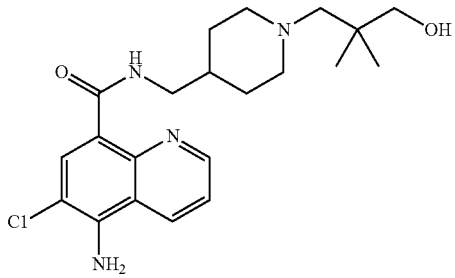

1M solution of Lithium aluminum hydride (0.38 mL) was added to a stirred solution of 5-amino-6-chloro-N-{[1-(2-methoxy carbonyl-2-methyl propan-1-yl)-4-piperidinyl]methyl}quinoline-8-carboxamide (0.11 grams, 0.254 mmole, obtained from Example 31) in THF (5 mL) at 0° C. Then reaction mass temperature was slowly raised to RT and stirred for 4 hours at same temperature. The progress of the reaction was monitored by thin layer chromatography. After completion of the reaction (thin layer chromatography), the mass was cooled to 0° C. and added water (0.2 mL), followed by ethyl acetate (10 mL). The resulting solution was filtered through celite pad and was washed with ethyl acetate (10 ml). The filtrate was dried over sodium sulphate. The organic phase was filtered and concentrated under vacuum to obtain the crude residue, which was further purified by flash chromatography using TEA:methanol:chloroform (0.5:5:94.5) to afford the title compound.

Yield: 0.051 grams (49%).

$^1$H-NMR (δ ppm): 0.75 (6H, s), 1.21-1.29 (2H, m), 1.33-1.36 (1H, m), 1.61-1.46 (2H, m), 2.08-2.15 (4H, m), 2.77-2.80 (2H, m), 3.12-3.17 (2H, m), 3.30-3.36 (2H, m), 4.59-4.63 (1H, m), 6.89 (2H, bs), 7.54-7.58 (1H, dd, J=8.60, 4.24 Hz), 8.37 (1H, s), 8.83-8.93 (2H, m), 10.87-10.90 (1H, t);

Mass (m/z): 405.1 (M+H)$^+$; 407.3 (M+H)$^+$.

Step (ii): Preparation of 5-Amino-6-chloro-N-{[1-(3-hydroxy-2,2-dimethyl propyl)-4-piperidinyl]methyl}quinoline-8-carboxamide L(+)-tartarate A clear solution of L(+)-tartaric acid (0.015 gram, 0.1 mmole) in 2 mL methanol was added to a stirred solution of 5-amino-6-chloro-N-{[1-(3-hydroxy-2,2-dimethyl propyl)-4-piperidinyl]methyl}quinoline-8-carboxamide (0.04 gram, 0.098 mmole, obtained in above step) in methanol (2 mL) at RT. The clear mass was stirred further for 2 hours at RT. The solvent was evaporated to afford solid mass. The solid mass was further triturated with diethyl ether (2×3 mL) and dried under vacuum to obtain the title compound.

Yield: 0.045 gram (82%).

$^1$H-NMR (δ ppm): 0.80 (6H, s), 1.35-1.40 (2H, m), 1.58-1.60 (1H, m), 1.67-1.70 (2H, m), 2.35-2.41 (4H, m), 2.95-2.97 (3H, m), 3.12-3.17 (2H, m), 3.30-3.36 (2H, m), 4.14 (2H, s), 6.91 (2H, bs), 7.55-7.58 (1H, dd, J=8.60, 4.24 Hz), 8.37 (1H, s), 8.83-8.94 (2H, m), 10.88-10.91 (1H, t);

Mass (m/z): 405.1 (M+H)$^+$; 407.3 (M+H)$^+$.

Example 34

The compound of Example 34 was prepared by following the experimental procedure as described in the Example 33 given above, with some noncritical variations.

| Example Number | Chemical name and Structure | Characterization data |
|---|---|---|
| 34. | 5-Amino-6-chloro-N-{[3-(3-hydroxy-2,2-dimethyl propyl)-3-azabicyclo[3.1.0]hex-6-yl]methyl}quinoline-8-carboxamide L(+)-tartarate 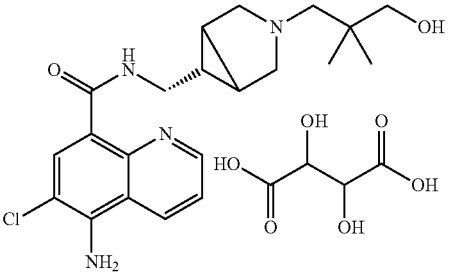 | $^1$H-NMR (δ ppm): 0.75 (6H, s), 1.30-1.36 (1H, m), 1.42-1.46 (2H, m), 2.35-2.39 (2H, m), 2.53-2.57 (2H, m), 3.05-3.15 (4H, m), 3.25-3.36 (3H, m), 4.21 (2H, s), 6.91 (2H, s), 7.55-7.58 (1H, dd. J = 8.60, 4.20 Hz), 8.38 (1h, s), 8.83-8.96 (2H, m), 10.86-10.89 (1H, t); Mass (m/z): 403.2 (M + H)$^+$; 405.2 (M + H)$^+$. |

Example 35

Preparation of 5-Amino-6-chloro-N-{[1-(2-hydroxy-2-methyl propyl)-4-piperidinyl]methyl}quinoline-8-carboxamide L(+)-tartarate

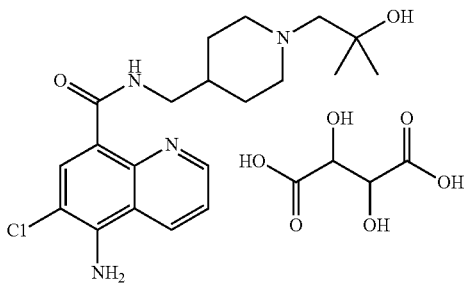

Step (i): Preparation of 5-Amino-6-chloro-N-{[1-(2-hydroxy-2-methyl propyl)-4-piperidinyl]methyl}quinoline-8-carboxamide

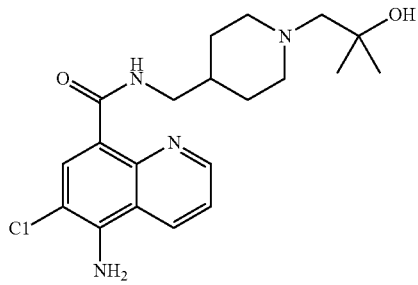

A solution of 5-amino-6-chloro-N-[(4-piperidinyl) methyl] quinoline-8-carboxamide (0.85 grams, 2.66 mmole, obtained from preparation 2), isobutyleneoxide (0.38 grams, 5.33 mmole) and triethylamine (0.54 grams, 5.33 mmole) in methanol (15 mL) was stirred overnight at 75° C. The progress of the reaction was monitored by thin layer chromatography. After completion of the reaction (thin layer chromatography), the reaction mass was concentrated on rotavacuum to obtain the crude residue, which was further purified by flash chromatography using TEA:methanol:chloroform (0.25:0.75:99) to afford the title compound.

Yield: 0.69 grams (67%).

$^1$H-NMR (δ ppm): 1.25 (6H, s), 1.27-1.30 (2H, m), 1.81-1.92 (2H, m), 1.97-2.08 (2H, m), 2.38-2.54 (4H, m), 3.05-3.07 (2H, m), 3.47-3.50 (2H, m), 4.93-4.96 (2H, m), 7.45-7.48 (1H, dd, J=8.60, 4.24 Hz), 8.22-8.24 (1H, m), 8.77 (1H, s), 8.89-8.90 (1H, m), 11.08-11.12 (1H, t);

Mass (m/z): 391.3 (M+H)$^+$; 393.2 (M+H)$^+$.

Step (ii): Preparation of 5-Amino-6-chloro-N-{[1-(2-hydroxy-2-methyl propyl)-4-piperidinyl]methyl}quinoline-8-carboxamide L(+)-tartarate A clear solution of L(+)-tartaric acid (0.155 gram, 1.03 mole) in 2 mL methanol was added to a stirred solution of 5-amino-6-chloro-N-{[1-(2-hydroxy-2-methyl propyl)-4-piperidinyl]methyl}quinoline-8-carboxamide (0.42 gram, 1.07 mmole, obtained in above step) in methanol (2 mL) at RT. The clear mass was stirred further for 2 hours at RT. The solvent was evaporated to afford solid mass. The solid mass was further triturated with diethyl ether (2×3 mL) and dried under vacuum to obtain the title compound.

Yield: 0.524 gram (89%).

$^1$H-NMR (δ ppm): 1.12 (6H, s), 1.43-1.46 (2H, m), 1.69-1.73 (2H, m), 2.48-2.65 (4H, m), 3.15-3.34 (6H, m), 4.09 (2H, s), 6.91 (2H, s), 7.55-7.59 (1H, dd, J=8.60, 4.24 Hz), 8.38 (1H, s), 8.83-8.86 (1H, m), 8.93-8.94 (1H, m), 10.88-10.91 (1H, t);

Mass (m/z): 391.3 (M+H)$^+$; 393.2 (M+H)$^+$.

Examples 36 to 45

The compounds of Examples 36 to 45 were prepared by following the experimental procedure as described in the Example 35 given above, with some noncritical variations.

| Example Number | Chemical name and Structure | Characterization data |
|---|---|---|
| 36. | 5-Amino-6-chloro-N-{[4-fluoro-1-(2-hydroxy-2-methyl propyl)-4-piperidinyl]methyl} quinoline-8-carboxamide | $^1$H-NMR (δ ppm): 1.05 (6H, s), 1.68-1.75 (4H, m), 2.18 (2H, s), 2.38-2.40 (2H, m), 2.69-2.72 (2H, m), 3.61-3.68 (2H, m), 4.03 (1H, s), 6.96 (2H, bs), 7.55-7.58 (1H, dd, J = 8.32; 4.04 Hz), 8.40 (1H, s), 8.84-8.87 (1H, m), 8.92-8.93 (1H, m), 11.07-11.09 (1H, t); Mass (m/z): 409.1 (M + H)$^+$; 411.2 (M + H)$^+$. |
| 37. | 5-Amino-6-chloro-N-{[4-fluoro-1-(2-hydroxy-2-methyl propyl)-4-piperidinyl]methyl} quinoline-8-carboxamide L(+)-tartarate | $^1$H-NMR (δ ppm): 1.08 (6H, s), 1.77-1.88 (4H, m), 2.38 (2H, s), 2.49-2.54 (2H, m), 2.84-2.87 (2H, m), 3.12-3.17 (1H, s), 3.63-3.70 (2H, m), 4.18 (2H, s), 6.97 (2H, bs), 7.56-7.59 (1H, dd, J = 8.52, 4.16 Hz), 8.40 (1H, s), 8.85-8.87 (1H, m), 8.93-8.94 (1H, m), 11.08-11.11 (1H, t); Mass (m/z): 409.1 (M + H)$^+$; 411.2 (M + H)$^+$. |
| 38. | 5-Amino-6-chloro-N-{[4-fluoro-1-(2-hydroxy-2-methyl propyl)-4-piperidinyl]methyl} quinoline-8-carboxamide hydrochloride | $^1$H-NMR (δ ppm): 1.24 (6H, s), 1.97-2.29 (4H, m), 3.10-3.21 (4H, m), 3.55-3.85 (4H, m), 5.24-5.26 (1H, m), 7.02 (2H, bs), 7.57-7.60 (1H, dd, J = 8.52, 4.2 Hz), 8.41 (1H, s), 8.87-9.06 (3H, m), 11.14-11.17 (1H, t); Mass (m/z): 409.1 (M + H)$^+$; 411.2 (M + H)$^+$. |
| 39. | 5-Amino-6-chloro-N-{[4-fluoro-1-(2-hydroxy-2-methyl propyl)-4-piperidinyl]methyl} quinoline-8-carboxamide fumarate | $^1$H-NMR (δ ppm): 1.06 (6H, s), 1.73-1.78 (4H, m), 2.24 (2H, s), 2.43-2.48 (2H, m), 2.74-2.77 (2H, s), 3.62-3.69 (2H, m), 6.59 (2H, s), 6.97 (2H, bs), 7.55-7.58 (1H, dd, J = 8.56, 4.4 Hz), 8.40 (1H, s), 8.85-8.93 (2H, m), 11.07-11.10 (1H, t); Mass (m/z): 409.1 (M + H)$^+$; 411.2 (M + H)$^+$. |

| Example Number | Chemical name and Structure | Characterization data |
|---|---|---|
| 40. | 5-Amino-6-chloro-N-{(3-(2-hydroxy-2-methyl propyl)-3-azabicyclo[3.1.0]hex-6-yl]methyl} quinoline-8-carboxamide L(+)-tartarate | $^1$H-NMR (δ ppm): 1.08 (6H, s), 1.42-1.46 (2H, m), 2.35-2.39 (2H, m), 2.53-2.57 (2H, m), 3.05-3.15 (4H, m), 3.25-3.36 (2H, m), (4.21 (2H, s), 6.91 (2H, s 7.55-7.58 (1H, dd, J = 8.60; 4.20 Hz), 8.38 (1H, s), 8.83-8.96 (2H, m), 10.86-10.89 (1H, t);<br>Mass (m/z): 389.2 (M + H)$^+$; 391.2 (M + H)$^+$. |
| 41. | 5-Amino-6-fluoro-N-{[1-(2-hydroxy-2-methyl propyl)-4-piperidinyl]methyl}quinoline-8-carboxamide L(+)-tartarate | $^1$H-NMR (δ ppm): 1.09 (6H, s), 1.78-1.86 (4H, m), 2.38 (2H, s), 2.55-2.59 (2H, m), 2.85-2.88 (2H, m), 3.06 (1H, s), 3.64-3.71 (2H, m), 4.19 (2H, s), 6.78 (2H, s), 7.53-7.56 (1H, dd, J = 8.56, 4.40 Hz), 8.27-8.31 (1H, m), 8.81-8.91 (2H, m), 11.14-11.17 (1H,t);<br>Mass (m/z): 375.3 (M + H)$^+$. |
| 42. | 5-Amino-6-fluoro-N-{[4-fluoro-1-(2-hydroxy-2-methyl propyl)-4-piperidinyl]methyl} quinoline-8-carboxamide | $^1$H-NMR (δ ppm): 1.05 (6H, s), 1.68-1.76 (4H, m), 2.19 (2H, s), 2.35-2.40 (2H, m), 2.69-2.72 (2H, m), 3.62-3.69 (2H, m), 4.03 (1H, s), 6.75 (2H, s), 7.52-7.55 (1H, dd, J = 8.44, 4.04 Hz), 8.27-8.30 (1H, m), 8.80-8.91 (2H, m), 11.12-11.15 (1H, t);<br>Mass (m/z): 393.2 (M + H)$^+$. |
| 43. | 5-Amino-6-fluoro-N-{[4-fluoro-1-(2-hydroxy-2-methyl propyl)-4-piperidinyl]methyl} quinoline-8-carboxamide L(+)-tartarate | $^1$H-NMR (δ ppm): 1.09 (6H, s), 1.74-1.89 (4H, m), 2.42 (2H, s), 2.55-2.62 (2H, m), 2.86-2.92 (2H, m), 3.20 (1H, s), 3.58-3.70 (2H, m), 4.20 (2H, s), 6.77 (2H, s), 7.53-7.56 (1H, dd, J = 8.56, 4.16 Hz), 8.27-8.31 (1H, m), 8.81-8.91 (2H, m), 11.14-11.17 (1H, t);<br>Mass (m/z): 393.2 (M + H)$^+$. |

| Example Number | Chemical name and Structure | Characterization data |
|---|---|---|
| 44. | 5-Amino-6-bromo-N-{[1-(2-hydroxy-2-methyl propyl)-4-piperidinyl]methyl} quinoline-8-carboxamide L(+)-tartarate 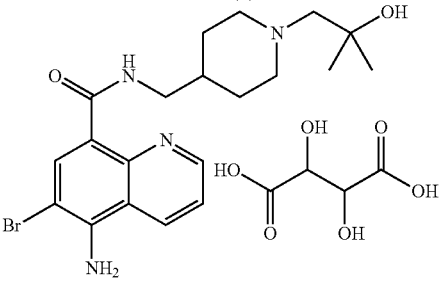 | $^1$H-NMR (δ ppm): 1.11 (6H, s), 1.74-1.91 (4H, m), 2.49 (2H, s), 2.55-2.64 (2H, m), 2.85-2.92 (2H, m), 3.17 (1H, s), 3.61-3.70 (2H, m), 4.16 (2H, s), 6.86 (2H, s), 7.55-7.58 (1H, dd, J = 8.64, 4.24 Hz), 8.51 (1H, s), 8.85-8.95 (2H, m), 10.88-10.91 (1H, t); Mass (m/z): 435.1 (M + H)$^+$; 437.2 (M + H)$^+$. |
| 45. | 5-Amino-6-bromo-N-{[4-fluoro-1-(2-hydroxy-2-methyl propyl)-4-piperidinyl]methyl} quinoline-8-carboxamide L(+)-tartarate 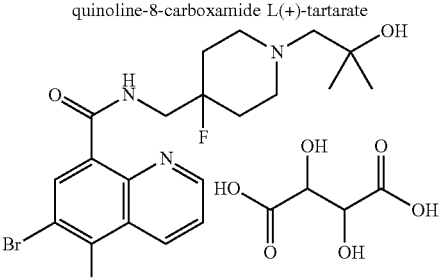 | $^1$H-NMR (δ ppm): 1.08 (6H, s), 1.77-1.88 (4H, m), 2.36 (2H, s), 2.54-2.59 (2H, m), 2.84-2.87 (2H, m), 3.15 (1H, s), 3.63-3.70 (2H, m), 4.18 (2H, s), 6.91 (2H, s), 7.55-7.59 (1H, dd, J = 8.56, 4.24 Hz), 8.54 (1H, s), 8.86-8.88 (1H, m), 8.94-8.95 (1H, m), 11.07-11.10 (1H, t); Mass (m/z): 453.2 (M + H)$^+$; 455.2 (M + H)$^+$. |

Example 46

Preparation of 5-Amino-6-chloro-N-{[1-(2-fluoro-2-methyl propyl)-4-piperidinyl]methyl}quinoline-8-carboxamide

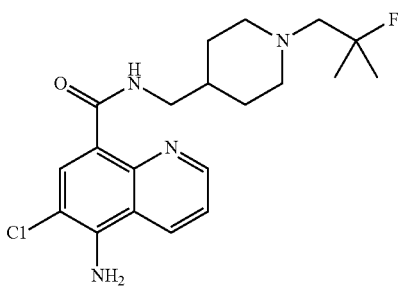

DAST (0.03 grams, 0.186 mmole) was added to a stirred solution of 5-amino-6-chloro-N-{[1-(2-hydroxy-2-methyl propyl)-4-piperidinyl]methyl}quinoline-8-carboxamide (0.03 grams, 0.076 mmole, obtained from the step (i) of example 35) in DCM (5 mL) at −30° C. Then reaction mass temperature was slowly raised to RT and stirred for overnight at same temperature. The progress of the reaction was monitored by TLC. After completion of the reaction (TLC), the mass was quenched in chilled water (10 mL). The pH of the mass was adjusted to ~9.5 using aqueous ammonia, the compound was extracted with DCM (3×5 mL). The combined organic phase was washed with water (5 mL), brine solution (5 mL) and dried over sodium sulphate. The organic phase was concentrated on rotavacuum to obtain the crude residue, which was further purified by flash chromatography using TEA:methanol:chloroform (1:5:94) to afford the title compound.

Yield: 0.013 grams (43%).

$^1$H-NMR (δ ppm): 1.24 (6H, s), 1.30-1.38 (3H, m), 1.48-1.52 (2H, m), 1.63-1.66 (2H, m), 2.01-2.06 (2H, m), 2.35-2.41 (2H, m), 2.86-2.89 (2H, m), 6.90 (2H, bs), 7.55-7.58 (1H, dd, J=8.56, 4.16 Hz), 8.37 (1H, s), 8.83-8.85 (1H, m), 8.93-8.94 (1H, m), 10.88-10.90 (1H, t);

Mass (m/z): 393.2 (M+H)$^+$; 395.2 (M+H)$^+$.

Examples 47 to 48

The compounds of Examples 47 to 48 were prepared by following the experimental procedure as described in the Example 46 given above, with some noncritical variations.

| Example Number | Chemical name and Structure | Characterization data |
|---|---|---|
| 47. | 5-Amino-6-chloro-N-{[3-(2-fluoro-2-methyl propyl)-3-azabicyclo[3.1.0]hex-6-yl]methyl} quinoline-8-carboxamide 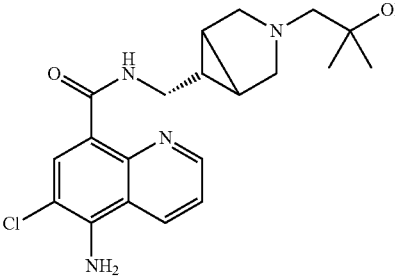 | $^1$H-NMR (δ ppm): 1.27 (3H, s), 1.32 (3H, s), 1.41-1.48 (1H, m), 1.53-1.55 (2H, in), 2.44-2.55 (4H, m), 3.10-3.12 (2H, m), 3.43-3.46 (2H, m), 6.90 (2H, s), 7.45-7.48 (1H, dd, J = 8.52, 4.16 Hz), 8.22-8.24 (1H, m), 8.78 (1H, s), 8.91-8.92 (1H, m), 11.00-11.08 (1H, t); (m/z): 391.3 (M + H)$^+$; 393.1 (M + H)$^+$. |
| 48. | 5-Amino-6-chloro-N-{[4-fluoro-1-(2-fluoro-2-methyl propyl)-4-piperidinyl]methyl} quinoline-8-carboxamide 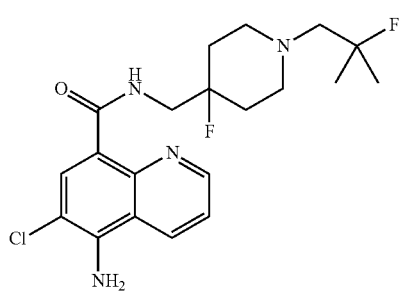 [SMILES: CC(C)(F)CN1CCC(F)(CNC(=O)c2cc(Cl)c(N)c3cccnc23)CC1] | $^1$H-NMR (δ ppm): 1.25 (3H, s), 1.31 (3H, s), 1.68-1.77 (4H, m), 2.33-2.49 (4H, m), 2.66-2.69 (2H, m), 3.62-3.69 (2H, m), 6.96 (2H, bs), 7.55-7.58 (1H, dd, J = 8.32, 4.04 Hz), 8.40 (1H, s), 8.84-8.87 (1H, in), 8.92-8.93 (1H, m), 11.08-11.10 (1H, t); Mass (m/z): 411.1 (M + H)$^+$; 413.1 (M + H)$^+$. |

Example 49

Preparation of 5-Amino-6-chloro-N-{[1-(2-hydroxy ethyl)-4-piperidinyl]methyl}quinoline-8-carboxamide

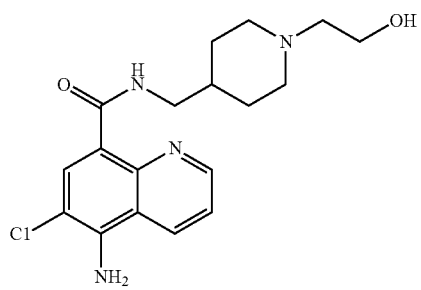

A solution of 5-amino-6-chloro-N-[(4-piperidinyl) methyl] quinoline-8-carboxamide (0.1 grams, 0.313 mmole, obtained from preparation 2), bromoethanol (0.047 grams, 0.376 mmole) and potassium carbonate (0.086 grams, 0.623 mmole) in acetonitrile (15 mL) was stirred overnight at 85° C., the progress of the reaction was monitored by TLC. After completion of the reaction (TLC), the reaction mass was concentrated and the obtained slurry was quenched in water (30 mL). The mass pH was adjusted to ~9.5 using aqueous ammonia, the compound was extracted with DCM (3×15 mL). The combined organic phase was washed with water (15 mL), brine solution (15 mL) and dried over sodium sulphate. The organic phase was concentrated on rotavacuum to obtain the crude residue, which was further purified by flash chromatography using TEA:methanol:chloroform (1:3:96) to afford the title compound.

Yield: 0.07 grams (62%).

$^1$H-NMR (δ ppm): 1.36-1.45 (3H, m), 1.72-1.85 (3H, m), 2.05-2.17 (2H, m), 2.50-2.53 (2H, m), 2.92-2.94 (2H, m), 3.47-3.50 (2H, m), 3.58-3.60 (2H, m), 4.97 (2H, s), 7.45-7.48 (1H, dd, J=8.56; 4.20 Hz), 8.23-8.25 (1H, m), 8.78 (1H, s), 8.89-8.90 (1H, m), 11.07-11.12 (1H, t);

Mass (m/z): 363.2 (M+H)$^+$; 365.2 (M+H)$^+$.

Examples 50 to 51

The compounds of Examples 50 to 51 were prepared by following the experimental procedure as described in the Example 49 given above, with some noncritical variations.

| Example Number | Chemical name and Structure | Characterization data |
|---|---|---|
| 50. | 5-Amino-6-chloro-N-{[3-(2-hydroxy ethyl)-3-azabicyclo[3.1.0]hex-6-yl]methyl} quinoline-8-carboxamide 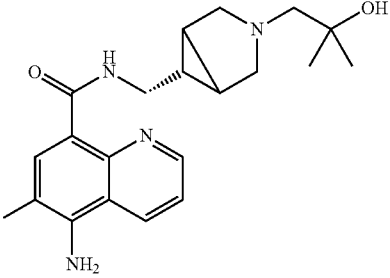 | $^1$H-NMR (δ ppm): 1.35-1.38 (3H, m), 2.23-2.25 (2H, m), 2.40-2.43 (2H, m), 2.95-2.97 (2H, m), 3.23-3.26 (2H, m), 3.34-3.40 (2H, m), 4.31-4.34 (1H, m), 6.91 (2H, bs), 7.55-7.58 (1H, dd, J = 8.56, 4.20 Hz), 8.37 (1H, s), 8.83-8.85 (1H, m), 8.95-8.96 (1H, m), 10.84-10.87 (1H, t); Mass (m/z): 361.2 (M + H)$^+$; 363.1 (M + H)$^+$. |
| 51. | 5-Amino-6-chloro-N-{[3-(3-hydroxy propyl)-3-azabicyclo[3.1.0]hex-6-yl]methyl} quinoline-8-carboxamide 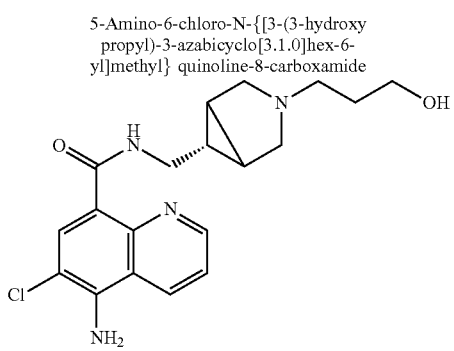 | $^1$H-NMR (δ ppm): 1.32-1.36 (3H, m), 1.46-1.49 (2H, m), 2.17-2.19 (2H, m), 2.35-2.39 (2H, m), 2.93-2.95 (2H, m), 3.23-3.29 (2H, m), 3.42-3.49 (2H, m), 4.32-4.36 (1H, m), 6.90 (2H, s), 7.55-7.58 (1H, dd, J = 8.60, 4.20 Hz), 8.30-8.35 (1H, m), 8.83-8.96 (2H, m), 10.85-10.87 (1H, t); Mass (m/z): 375.2 (M + H)$^+$; 377.2 (M + H)$^+$. |

Example 52

Preparation of 5-Amino-6-chloro-N-{[1-(2-fluoro ethyl)-4-piperidinyl]methyl}quinoline-8-carboxamide

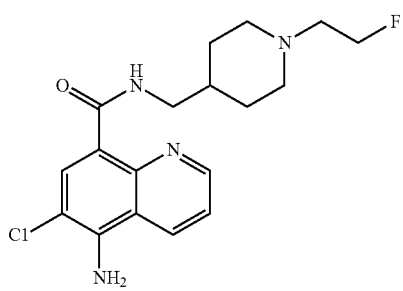

DAST (0.072 grams, 0.448 mmole) was added to a stirred solution of 5-amino-6-chloro-N-{[1-(2-hydroxy ethyl)-4-piperidinyl]methyl}quinoline-8-carboxamide (0.07 grams, 0.179 mmole, obtained from Example 49) in DCM (5 mL) at −30° C. Then reaction mass temperature was slowly raised to RT and stirred overnight at same temperature. The progress of the reaction was monitored by thin layer chromatography. After completion of the reaction (thin layer chromatography), the mass was quenched in chilled water (10 mL). The mass pH was adjusted to ~9.5 using aqueous ammonia, the compound was extracted with DCM (3×5 mL). The combined organic phase was washed with water (5 mL), brine solution (5 mL) and dried over sodium sulphate. The organic phase was concentrated on rotavacuum to obtain the crude residue, which was further purified by flash chromatography using TEA:methanol: chloroform (0.5:2: 97.5) to afford the title compound.

Yield: 0.014 grams (20%).

$^1$H-NMR (δ ppm): 1.22-1.34 (4H, m), 1.49-1.53 (1H, m), 1.66-1.69 (2H, m), 1.93-1.99 (2H, m), 2.51-2.53 (1H, m), 2.58-2.60 (1H, m), 2.86-2.88 (2H, m), 4.42-4.44 (1H, m), 4.54-4.56 (1H, m), 6.90 (2H, bs), 7.55-7.58 (1H, dd, J=8.64, 4.28 Hz), 8.37 (1H, s), 8.83-8.85 (1H, m), 8.93-8.94 (1H, m), 10.88-10.91 (1H, t); Mass (m/z): 365.2 (M+H)$^+$; 367.2 (M+H)$^+$.

Example 53

The compound of Example 53 was prepared by following the experimental procedure as described in the Example 52 given above, with some noncritical variations.

| Example Number | Chemical name and Structure | Characterization data |
|---|---|---|
| 53. | 5-Amino-6-chloro-N-{[3-(2-hydroxy ethyl)-3-azabicyclo[3.1.0]hex-6-yl]methyl} quinoline-8-carboxamide | ¹H-NMR (δ ppm): 1.33-1.36 (3H, m), 2.25-2.27 (2H, m), 2.40-2.43 (2H, m), 2.94-2.97 (2H, m), 3.23-3.26 (2H, m), 3.34-3.39 (2H, m), 6.89 (2H, bs), 7.55-7.58 (1H, dd, J = 8.56, 4.20 Hz), 8.38 (1H, s), 8.83-8.85 (1H, m), 8.95-8.96 (1H, m), 10.84-10.87 (1H, t); Mass (m/z): 363.2 (M + H)⁺; 365.1 (M + H)⁺. |

Example 54

Preparation of 5-Amino-6-chloro-N-{[3-(3-methoxy propyl)-3-azabicyclo[3.1.0]hex-6-yl] methyl}quinoline-8-carboxamide L(+)-tartarate

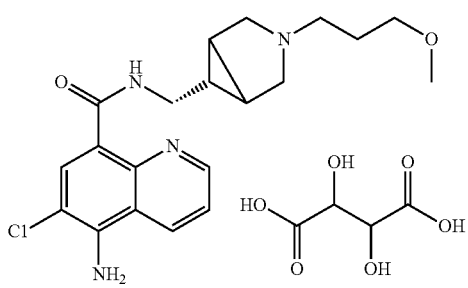

Step (i): Preparation of 5-Amino-6-chloro-N-{[3-(3-methoxy propyl)-3-azabicyclo[3.1.0]hex-6-yl] methyl}quinoline-8-carboxamide

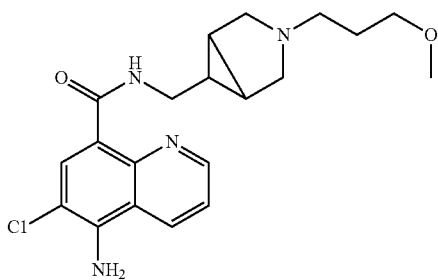

A solution of 5-Amino-6-chloro-N-{[3-azabicyclo[3.1.0] hex-6-yl]methyl}quinoline-8-carboxamide (0.05 grams, 0.141 mmole, obtained from preparation 4), 3-methoxy bromo propane (0.03 grams, 196 mmole) and potassium carbonate (0.065 grams, 0.471 mmole) in acetonitrile (5 mL) was stirred for 6 hours at 85° C., the progress of the reaction was monitored by thin layer chromatography. After completion of the reaction (thin layer chromatography), the reaction mass was quenched into chilled water (5 mL). The compound was extracted with ethyl acetate (3×5 mL), the extract was washed with water (5 mL), brine solution (5 mL) and dried over sodium sulphate. The organic phase was concentrated on rotavacuum to obtain the crude residue, which was further purified by flash chromatography using TEA:methanol: chloroform (0.5:2:97.5) to afford the title compound.

Yield: 0.03 grams (55%).

Step (ii): Preparation of 5-Amino-6-chloro-N-{[3-(3-methoxy propyl)-3-azabicyclo[3.1.0]hex-6-yl] methyl}quinoline-8-carboxamide L(+)-tartarate A solution of L(+)-tartaric acid (0.011 grams. 0.073 mole) in 2 mL methanol was added to a stirred solution of 5-Amino-6-chloro-N-{[3-(3-methoxy propyl)-3-azabicyclo [3.1.0]hex-6-yl]methyl}quinoline-8-carboxamide (0.03 grams, 0.077 mole, obtained from above step) in methanol (5 mL). The obtained clear mass was further stirred for 2 hrs at room temperature. The solvent was evaporated to afford solid mass. The solid mass was further triturated with diethyl ether (5 mL) and dried under reduced pressure to obtain title compound.

Yield: 0.039 grams (95%).

¹H-NMR (δ ppm): 1.31-1.35 (1H, m), 1.42-1.50 (1H, m), 1.86-1.94 (4H, m), 3.10-3.11 (1H, m), 3.18-3.21 (3H, m), 3.41-3.49 (6H, m), 3.61-3.69 (2H, m), 4.41 (2H, s), 7.50-7.53 (1H, m), 8.49 (1H, s), 8.66-8.68 (1H, dd, J=8.41, 1.42 Hz), 8.90-8.91 (1H, m);

Mass (m/z): 389.3 (M+H)⁺, 391.4 (M+H)⁺.

Example 55

Preparation of 5-Amino-6-chloro-N-{[1-(3-methoxy-2,2-dimethyl propyl)-4-piperidinyl] methyl}quinoline-8-carboxamide L(+)-tartarate

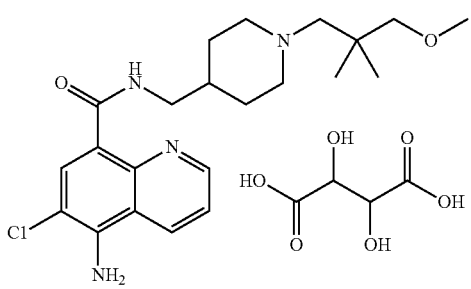

Step (i): Preparation of 5-Amino-6-chloro-N-{[1-(3-methoxy-2,2-dimethyl-propyl)-4-piperidinyl]methyl}quinoline-8-carboxamide

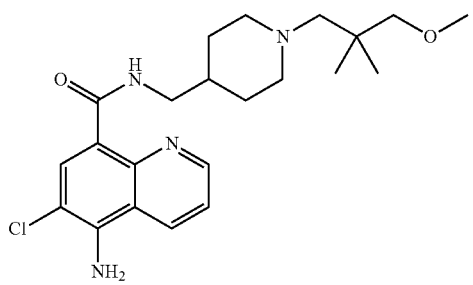 [SMILES: COCC(C)(C)CN1CCC(CNC(=O)c2cc(Cl)c(N)c3cccnc23)CC1]

A solution of 5-amino-6-chloro-N-[(4-piperidinyl)methyl] quinoline-8-carboxamide (0.2 grams, 0.627 mmole, obtained from preparation 2), 3-methoxy-2,2-dimethyl propyl toluene-4-sulfonate (0.34 grams, 1.255 mmole, obtained from preparation 7), cesium carbonate (0.41 grams, 1.255 mmole) and potassium iodide (0.21 grams, 1.255 mmole) in dimethylformamide (5 mL) was stirred for 24 hours at 120° C. while monitoring the progress of the reaction by TLC. After completion of the reaction (TLC), the reaction mass was cooled to room temperature and quenched onto chilled water (10 mL). The product was extracted with ethyl acetate (3×5 mL), the organic extracts were washed with water (5 mL), brine solution (5 mL) and dried over sodium sulfate. The organic phase was concentrated on rotavacuum to obtain the crude residue, which was further purified by flash chromatography using TEA:methanol:chloroform (0.5:2:97.5) to afford the title compound.

Yield: 0.033 grams (12.5%).

$^1$H-NMR (δ ppm): 0.77 (6H, s), 1.22-1.30 (3H, m), 1.47 (1H, m), 1.61-1.63 (2H, m), 2.07-2.16 (5H, m), 2.69-2.72 (2H, m), 3.01-3.02 (2H, d), 3.19 (3H, s), 6.91 (2H, s), 7.55-7.58 (1H, dd, J=8.52, 4.20 Hz), 8.37 (1H, s), 8.83-8.85 (1H, m), 8.93-8.94 (1H, m), 10.88-10.91 (1H, t);

Mass (m/z): 419.2 (M+H)$^+$, 421.3 (M+H)$^+$.

Step (ii): Preparation of 5-Amino-6-chloro-N-{[1-(3-methoxy-2,2-dimethyl propyl)-4-piperidinyl]methyl}quinoline-8-carboxamide L(+)-tartarate A solution of L(+)-tartaric acid (0.011 grams, 0.073 mole) in 2 mL methanol was added to a stirred solution of 5-amino-6-chloro-N-{[1-(3-methoxy-2,2-dimethyl propyl)-4-piperidinyl]methyl}quinoline-8-carboxamide (0.033 grams, 0.078 mole, obtainted from above step) in methanol (5 mL). The clear mass was further stirred for 2 hrs at room temperature. The solvent was evaporated, the residual solid mass was triturated with diethyl ether (5 mL) and dried under reduced pressure to obtain title compound.

Yield: 0.042 grams (95%).

$^1$H-NMR (δ ppm): 1.06 (6H, s), 1.67-1.70 (2H, m), 1.98-2.01 (3H, m), 2.98-3.02 (4H, m), 3.37 (3H, s), 3.41-3.50 (6H, m), 4.38 (2H, s), 7.51-7.55 (1H, d, J=8.60, 4.20 Hz), 8.50 (1H, s), 8.67-8.69 (1H, m), 8.91-8.92 (1H, m);

Mass (m/z): 419.3 (M+H)$^+$, 421.3 (M+H)$^+$.

Example 56

Preparation of 5-Amino-6-chloro-N-{[1-(2-methoxy-2-methyl propyl)-4-piperidinyl]methyl}quinoline-8-carboxamide

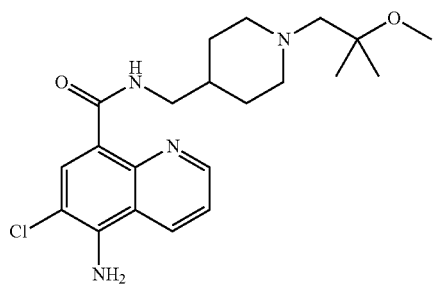 [SMILES: COC(C)(C)CN1CCC(CNC(=O)c2cc(Cl)c(N)c3cccnc23)CC1]

A solution of 5-amino-6-chloro-N-[(4-piperidinyl)methyl] quinoline-8-carboxamide (0.15 grams, 0.471 mmole, obtained from preparation 2), toluene-4-sulfonic acid 2-methoxy-2-methyl-propyl ester (0.25 grams, 0.968 mmole, obtained from preparation 8), cesium carbonate (0.31 grams, 0.968 mmole) and potassium iodide (0.156 grams, 0.968 mmole) in dimethylformamide (5 mL) was stirred for 24 hours at 120° C., the progress of the reaction was monitored by TLC. After completion of the reaction (TLC), the reaction mass was cooled to room temperature and quenched into chilled water (10 mL). The compound was extracted with ethyl acetate (3×5 mL), the extract was washed with water (5 mL), brine solution (5 mL) and dried over sodium sulphate. The organic phase was concentrated on rotavacuum to obtain the crude residue, which was further purified by flash chromatography using TEA:methanol: chloroform (0.5:2:97.5) to afford the title compound.

$^1$H-NMR (δ ppm): 1.06 (6H, s), 1.23-1.27 (4H, m), 1.35-1.42 (1H, m), 1.61-1.64 (2H, m), 2.01-2.07 (2H, m), 2.49 (2H, s), 2.88-2.94 (2H, m), 3.02 (3H, s), 6.89 (2H, s), 7.54-7.58 (1H, dd, J=8.56, 4.20 Hz), 8.37 (1H, s), 8.83-8.85 (1H, d, J=8.6 Hz), 8.93-8.94 (1H, d, J=3.64 Hz), 10.87-10.90 (1H, t);

Mass (m/z): 405.3 (M+H)$^+$; 407.2 (M+H)$^+$.

Example 57 to 58

The compounds of Examples 57 to 58 were prepared by following the experimental procedure as described in the Example 56 given above, with some noncritical variations.

chilled water (10 mL). The product was extracted with ethyl acetate (3×5 mL) and the combined organic extract was washed with water (5 mL), brine solution (5 mL) and dried over sodium sulfate. The organic phase was concentrated on rotavacuum and the residual mass was purified by flash chromatography using TEA:methanol: chloroform (0.5:2: 97.5) to afford the title compound.

| Example Number | Chemical name and Structure | Characterization data |
|---|---|---|
| 57. | 5-Amino-6-fluoro-N-{[1-(2-methoxy-2-methyl propyl)-4-piperidinyl]methyl} quinoline-8-carboxamide | $^1$H-NMR (δ ppm): 1.10 (6H, s), 1.26-1.33 (4H, m), 1.37-1.42 (1H, m), 1.62-1.66 (2H, m), 2.02-2.07 (2H, m), 2.51 (2H, s), 2.89-2.94 (2H, m), 3.05 (3H, s), 6.96 (2H, s), 7.54-7.57 (1H. dd, J = 8.64, 4.20 Hz), 8.28-8.32 (1H, m), 8.81-8.92 (2H, m), 11.10-11.12 (1H, t); Mass (m/z): 389.3 (M + H)$^+$; |
| 58. | 5-Amino-6-bromo-N-{[1-(2-methoxy-2-methyl propyl)-4-piperidinyl]methyl} quinoline-8-carboxamide | $^1$H-NMR (δ ppm): 1.11 (6H, s), 1.25-1.31 (4H. m), 1.35-1.40 (1H, m). 1.61-1.65 (2H, m), 2.03-2.08 (2H, m), 2.50 (2H, s), 2.89-2.95 (2H, m), 3.03 (3H, s), 6.93 (2H, s), 7.57-7.60 (1H, dd, J = 8.60, 4.20 Hz), 8.53 (1H, s), 8.85-8.88 (1H, m), 8.93-8.96 (1H, m), 11.09-11.11 (1H, t); Mass (m/z): 449.2 (M + H)$^+$; 451.2 (M + H)$^+$; |

Example 59

Preparation of 5-Amino-6-chloro-N-{[4-fluoro-1-(3-methoxy-2,2-dimethyl propyl)-4-piperidinyl]methyl}quinoline-8-carboxamide

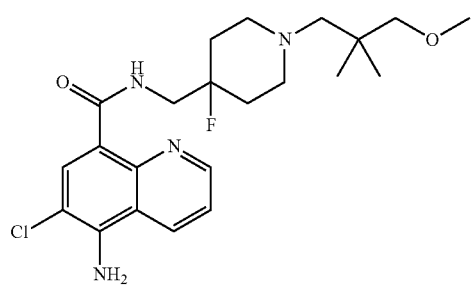 [SMILES: COCC(C)(C)CN1CCC(F)(CNC(=O)c2cc(Cl)c(N)c3cccnc23)CC1]

A solution of 5-amino-6-chloro-N-[4-fluoro-(4-piperidinyl)methyl] quinoline-8-carboxamide (0.2 grams, 0.529 mmole, obtained from preparation 5), 3-methoxy-2,2-dimethyl propyl toluene-4-sulfonate (0.32 grams, 1.19 mmole, obtained from preparation 7), cesium carbonate (0.39 grams, 1.19 mmole) and potassium iodide (0.2 grams, 1.20 mmole) in dimethylformamide (5 mL) was stirred for 24 hours at 120° C. and the progress of the reaction was monitored by TLC. After completion of the reaction (TLC), the reaction mass was cooled to room temperature and quenched onto Yield: 0.032 grams (12.5%).
$^1$H-NMR (δ ppm): 0.79 (6H, s), 1.24-1.30 (3H, m), 1.63-1.65 (2H, m), 2.09-2.15 (5H, m), 2.70-2.74 (2H, m), 3.03-3.04 (2H, m), 3.18 (3H, s), 6.92 (2H, s), 7.54-7.57 (1H, dd, J=8.62, 4.24 Hz), 8.39 (1H, s), 8.84-8.86 (1H, m), 8.94-8.95 (1H, m), 10.98-11.00 (1H, t);
Mass (m/z): 437.2 (M+H)$^+$, 439.3 (M+H)$^+$.

Example 60

Preparation of 5-Amino-6-chloro-N-{[4-fluoro-1-(2-methoxy-2-methyl propyl)-4-piperidinyl]methyl}quinoline-8-carboxamide

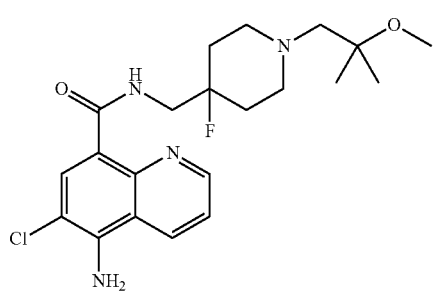 [SMILES: COC(C)(C)CN1CCC(F)(CNC(=O)c2cc(Cl)c(N)c3cccnc23)CC1]

A solution of 5-amino-6-chloro-N-[4-fluoro-(4-piperidinyl)methyl] quinoline-8-carboxamide (0.15 grams, 0.446 mmole, obtained from preparation 5), 2-methoxy-2-methyl-propyl toluene-4-sulfonate (0.23 grams, 0.892 mmole, obtained from preparation 8), cesium carbonate (0.29 grams, 0.892 mmole) and potassium iodide (0.148 grams, 0.892 mmole) in dimethylformamide (5 mL) was stirred for 24 hours at 120° C. while monitoring the progress of the reaction by TLC. After completion of the reaction (TLC), the mass was cooled to room temperature and quenched onto chilled water (10 mL). The product was extracted with ethyl acetate (3×5 mL), the combined organic extract was washed with water (5 mL), brine solution (5 mL) and dried over sodium sulfate. The organic phase was concentrated on rotavacuum and the residual mass was purified by flash chromatography using TEA:methanol:chloroform (0.5:2:97.5) to afford the title compound.

Yield: 0.024 grams (12.76%).

$^1$H-NMR ($\delta$ ppm): 1.10 (6H, s); 1.25-1.31 (2H, m), 1.63-1.66 (2H, m), 1.82-1.92 (2H, m), 2.10-2.16 (2H, m), 2.68-2.72 (2H, m), 3.03-3.04 (2H, m), 3.23 (3H, s), 6.90 (2H, s), 7.55-7.59 (1H, dd, J=8.60, 4.20 Hz), 8.40 (1H, s), 8.86-8.88 (1H, m), 8.94-8.95 (1H, m), 10.91-10.94 (1H, t);

Mass (m/z): 423.3 (M+H)$^+$, 425.3 (M+H)$^+$.

Example 61 to 62

The compounds of Examples 61 to 62 were prepared by following the experimental procedure as described in the Example 60 given above, with some noncritical variations.

Biological Assays

Example 63

Determination of $EC_{50}$ Values for 5-HT$_4$ Receptor

A stable CHO cell line expressing recombinant human 5-HT$_4$ receptor and pCRE-Luc reporter system was used for cell-based assay. The assay offers a non-radioactive based approach to determine binding of a compound to GPCRs. In this specific assay, the level of intracellular cyclic AMP, which is modulated by activation, or inhibition of the receptor is measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compounds were added in OptiMEM medium to the cells. The incubation was continued at 37° C. in $CO_2$ incubator for 4 hours. Medium was removed and cells were washed with phosphate buffered saline. The cells were lysed and luciferase activity was measured in a Luminometer. Luminescence units were plotted against the compound concentrations using Graphpad software. $EC_{50}$ values of the compounds were defined as the concentration required in stimulating the luciferase activity by 50%.

| Example Number | Chemical name and Structure | Characterization data |
|---|---|---|
| 61. | 5-Amino-6-fluoro-N-{[4-fluoro-1-(2-methoxy-2-methyl propyl)-4-piperidinyl]methyl} quinoline-8-carboxamide | $^1$H-NMR ($\delta$ ppm): 1.10 (6H, s), 1.76-1.87 (4H, m), 2.43 (2H, s), 2.56-2.62 (2H, m), 2.88-2.93 (2H, m), 3.24 (3H, s), 3.58-3.65 (2H, m), 6.91 (2H, s), 7.54-7.57 (1H, dd, J = 8.60, 4.16 Hz), 8.28-8.32 (1H, m), 8.83-8.91 (2H, m), 11.12-11.14 (1H, t); Mass (m/z): 407.3 (M + H)$^+$; |
| 62. | 5-Amino-6-bromo-N-{[4-fluoro-1-(2-methoxy-2-methyl propyl)-4-piperidinyl]methyl} quinoline-8-carboxamide | $^1$H-NMR ($\delta$ ppm): 1.09 (6H, s), 1.81-1.87 (4H, m), 2.39 (2H, s), 2.54-2.59 (2H, m), 2.84-2.87 (2H, m), 3.22 (3H, s), 3.63-3.69 (2H, m); 6.93 (2H, s), 7.55-7.58 (1H, dd, J = 8.52, 4.20 Hz), 8.55 (1H, s), 8.86-8.89 (1H, m), 8.92-8.95 (1H, m), 11.08-11.10 (1H, t); Mass (m/z): 467.1 (M + H)$^+$; 469.2 (M + H)$^+$; |

| Example Number | EC$_{50}$ (nM) | E$_{max}$ (%) |
|---|---|---|
| 1. | 0.04 | 76 |
| 2. | 0.5 | 59 |
| 3. | 2.5 | 79 |
| 4. | 0.05 | 56 |
| 6. | 0.1 | 56 |
| 7. | 0.57 | 71 |
| 8. | 0.7 | 87 |
| 9. | 0.8 | 87 |
| 10. | 1.5 | 83 |
| 11. | 0.3 | 77 |
| 12. | 0.2 | 83 |
| 13. | 0.09 | 70 |
| 15. | 0.5 | 54 |
| 16. | 0.08 | 62 |
| 17. | 0.8 | 72 |
| 20. | 1.1 | 58 |
| 22. | 0.2 | 86 |
| 23. | 0.4 | 67 |
| 24. | 4.1 | 81 |
| 25. | 0.6 | 93 |
| 26. | 0.1 | 65 |
| 27. | 0.6 | 63 |
| 28. | 0.1 | 66 |
| 29. | 0.1 | 84 |
| 30. | 0.1 | 65 |
| 31. | 0.3 | 60 |
| 32. | 1.2 | 60 |
| 35. | 0.1 | 48 |
| 36. | 2.3 | 74 |
| 37. | 2.2 | 62 |
| 38 | 1.3 | 54 |
| 40. | 3.9 | 63 |
| 41. | 0.2 | 64 |
| 42. | 4 | 74 |
| 43 | 2.9 | 43 |
| 44. | 0.3 | 52 |
| 45. | 11.8 | 89 |
| 46. | 0.1 | 58 |
| 47. | 1.6 | 79 |
| 48. | 8.9 | 84 |
| 50. | 1.7 | 72 |
| 51. | 1.4 | 85 |
| 52. | 0.41 | 63 |
| 53. | 4.5 | 65 |
| 54. | 0.7 | 70 |
| 55. | 0.09 | 72 |

Example 64

Rodent Pharmacokinetic Study

Male wistar rats (225±25 grams) were used as experimental animals. Three to five animals were housed in each cage. Two days prior to dosing day, male wistar rats (225-250 grams) were anesthetized with isoflurane for surgical placement of jugular vein catheter. Animals were fasted over night before oral dosing (p.o) and food pellets were allowed 2 hours post dosing, whereas during intravenous dosing food and water were provided as ad libitum. Three rats were dosed with compounds of formula (I) (3 mg/kg) orally and intravenously (1 mg/kg).

At each time point blood was collected through jugular vein and immediately replenish with an equivalent volume of normal saline from freely moving rats. Collected blood was transferred into a labeled eppendr off containing 10 μL of heparin as anticoagulant. Typically blood samples were collected as following time points: Pre dose, 0.08 (only i.v.), 0.25, 0.5, 1, 2, 4, 6, 8, and 24 hours post dose (n=3). Blood was centrifuged at 4000 rpm for 10 minutes. Plasma was prepared and stored frozen at −20° C. until analysis. The concentrations of the compounds of formula (I) were quantified in plasma by qualified LC-MS/MS method using suitable extraction technique. The compounds of formula (I) were quantified in the calibration range around 2-2000 ng/mL in plasma. Study samples were analyzed using calibration samples in the batch and quality control samples spread across the batch.

Pharmacokinetic parameters $C_{max}$, $T_{max}$, $AUC_t$, $T_{1/2}$ and Bioavailability were calculated by non-compartmental model using standard non-coinpartmental model by using WinNonLin 5.0.1 or Phoenix WinNonlin 6.2 version Software package.

| Example Number | Strain/Gender | Dose (mg/kg) | Vehicle | Route of administration | $C_{max}$ (ng/mL) | $T_{max}$ (h) | $AUC_t$ (ng·hr/mL) | $T_{1/2}$ (h) | Bioavailability (%) |
|---|---|---|---|---|---|---|---|---|---|
| 1. | Wistar/Male | 3 | Reagent grade water | oral (gavage) | 121 ± 25 | 0.42 ± 0.14 | 240 ± 35 | 4.0 ± 1.1 | 51 ± 5 |
|  | Wistar/Male | 1 | Sterile water for injection | intravenous (bolus) | 149 ± 6 | 0.08 ± 0.00 |  | 1.9 ± 0.7 |  |
| 2. | Wistar/Male | 3 | Reagent grade water | oral (gavage) | 140 ± 24 | 0.42 ± 0.14 | 531 ± 51 | 1.2 ± 0.1 | 62 ± 6 |
|  | Wistar/Male | 1 | Sterile water for injection | intravenous (bolus) | 252 ± 30 | 0.08 ± 0.00 | 284 ± 10 | 1.6 ± 0.1 |  |
| 13. | Wistar/Male | 3 | Reagent grade water | oral (gavage) | 76 ± 3 | 0.5 ± 0.0 | 235 ± 25 | 1.7 ± 0.3 | 37 ± 4 |
|  | Wistar/Male | 1 | Sterile water for injection | intravenous (bolus) | 168 ± 12 | 0.08 ± 0.0 | 211 ± 20 | 1.5 ± 0.3 |  |
| 27. | Wistar/Male | 3 | Reagent grade water | oral (gavage) | 173 ± 48 | 0.25 ± 0.00 | 236 ± 72 | 1.4 ± 0.2 | 20 ± 6 |
|  | Wistar/Male | 1 | Sterile water for injection | intravenous (bolus) | 448 ± 41 | 0.08 ± 0.00 | 401 ± 15 | 1.7 ± 0.4 |  |
| 37. | Wistar/Male | 3 | Reagent grade water | oral (gavage) | 137 ± 37 | 0.25 ± 0.00 | 200 ± 49 | 1.3 ± 0.3 | 24 ± 6 |
|  | Wistar/Male | 1 | Sterile water for injection | intravenous (bolus) | 324 ± 52 | 0.08 ± 0.00 | 274 ± 25 | 1.9 ± 0.1 |  |
| 43. | Wistar/Male | 3 | Reagent grade water | oral (gavage) | 231 ± 40 | 0.33 ± 0.14 | 373 ± 39 | 3.4 ± 2.2 | 34 ± 4 |
|  | Wistar/Male | 1 | Sterile water for injection | intravenous (bolus) | 306 ± 47 | 0.08 ± 0.0 | 362 ± 83 | 1.9 ± 0.9 |  |

Example 65

Rodent Brain Penetration Study

Male Wistar rats (225±25 grams) were used as experimental animals. Three animals were housed in each cage. Animals were given water and food ad libitum throughout the experiment and maintained on a 12 hours light/dark cycle.

Brain penetration was determined in discrete manner in rats. One day prior to dosing day, male wistar rats (225-250 grams) were acclimatized. After acclimatization the rats were grouped according to their weight. In each group, 3 animals were kept in individual cage and allowed free access to food and water. At each time point (0.50, 1, and 2 hours) n=3 animals were used.

The compounds of formula (I) were suitably preformulated and administered orally at (free base equivalent) 3 mg/kg. Blood samples were removed via, cardiac puncture by using isoflurane anesthesia. The animals were sacrificed to collect brain tissue. Plasma was separated and brain samples were homogenized and stored frozen at −20° C. until analysis. The concentrations of the compounds of formula (I) in plasma and brain were determined using LC-MS/MS method.

The compounds of formula (I) were quantified in plasma and brain homogenate by qualified LC-MS/MS method using suitable extraction technique. The compounds of formula (I) were quantified in the calibration range of 1-500 ng/mL in plasma and brain homogenate. Study samples were analyzed using calibration samples in the batch and quality control samples spread across the batch. Extent of brain-plasma ratio was calculated ($C_b/C_p$).

(different doses) in a volume of 5.0 mL/kg) or prucalopride (10.0 mg/kg in a volume of 5.0 mL/kg) dissolved in sterile water for injection. Mice were sacrificed 60 minutes after the drug injection by cervical dislocation, the brains were quickly isolated and the cortex was dissected at −20° C. The cortex was immediately kept on a dry ice and weighed before being stored at −80° C. until Enzyme-linked immunosorbent assay (ELISA) was performed.

Sample Preparation:
1. Brain tissues were thawed and Tris Buffer Saline containing protease inhibitors (TBS, 4 times by volume) added (0.8 mL/200 mg tissues).
2. Brain tissue samples were homogenized using glass-Teflon homogenizer at 10 strokes. The resulting homogenates were centrifuged at 15,000 rpm at 4° C. for 60 minutes.
3. The supernatant was discarded and to the precipitate, 4 times volume (0.8 mL/200 mg tissues) of TBS was added. Again homogenized followed by centrifugation at 15,000 rpm 4° C. for 30 minutes.
4. From the above centrifuged mixture the supernatant was discarded and 10 times volume of 6M Guanidine-HCl in 50 mM Tris buffer pH: 7.6 (500 µL/50 mg tissues) was added. The resulting solution was sonicated for 5 seconds, 4 times.
5. Resulting mixture was incubated at the RT for 30 minutes, followed by centrifugation at 15,000 rpm, 4° C. for 30 minutes. From this 5 µL of supernatant solution was taken and diluted with 155 µL of EIA buffer (dilution factor 32).

Measurement of sAPPα by ELISA Kit:

To investigate the role of an acute treatment of test compound on sAPPα levels, we measured the expression of this protein in homogenates from the cortex of treated and

| Example Number | Strain/Gender | Dose (mg/kg) | Vehicle | Route of administration | Single dose Brain Penetration ($C_b/C_p$) |
|---|---|---|---|---|---|
| 1. | Wistar/Male | 3 | Reagent grade water | oral (gavage) | 0.48 ± 0.03 |
|  | Wistar/Male | 1 | Sterile water for injection | intravenous (bolus) |  |
| 2. | Wistar/Male | 3 | Reagent grade water | oral (gavage) | 1.31 ± 0.10 |
|  | Wistar/Male | 1 | Sterile water for injection | intravenous (bolus) |  |
| 13. | Wistar/Male | 3 | Reagent grade water | oral (gavage) | 0.41 ± 0.04 |
|  | Wistar/Male | 1 | Sterile water for injection | intravenous (bolus) |  |
| 27. | Wistar/Male | 3 | Reagent grade water | oral (gavage) | 0.40 ± 0.02 |
|  | Wistar/Male | 1 | Sterile water for injection | intravenous (bolus) |  |
| 37. | Wistar/Male | 3 | Reagent grade water | oral (gavage) | 0.61 ± 0.07 |
|  | Wistar/Male | 1 | Sterile water for injection | intravenous (bolus) |  |
| 43. | Wistar/Male | 3 | Reagent grade water | oral (gavage) | 0.93 ± 0.26 |
|  | Wistar/Male | 1 | Sterile water for injection | intravenous (bolus) |  |

Example 66

Estimation of Mice Brain Cortical sAPPα Levels

Experimental Procedure:

The control group of mice received sterile water for injection subcutaneously (s.c.). The treated groups (9 mice per group) received a single s.c. injection of test compound untreated mice by ELISA assay. The entire procedure was followed as described in the ELISA kit manual (Mouse/Rat sAPPα ELISA, Catalog Number: JP27415, Innovation Beyond Limits International, Hamburg, Germany).

Statistical Analysis:

Statistical analyses were performed using the Graph Pad Prism (Version 4). Data are Mean±SD of sAPPa levels expressed as percentage of control values (mice which received water for injection). Values were compared between the different groups by using unpaired t test. The significance level was set at *p<0.05; p<0.0; *<0.001.
Result for Example 13 (FIG. 1)

Figure 2:
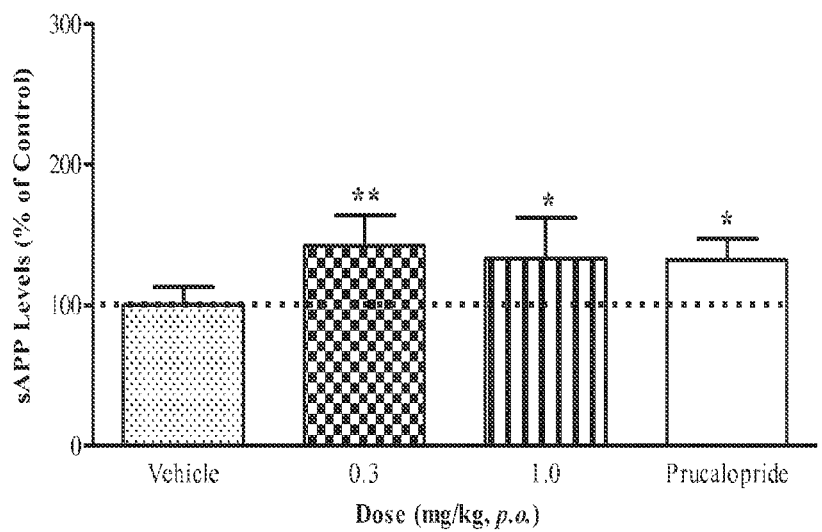

At 60 minutes post treatment, the compound of Example 13 showed significant increase in the mice brain cortical sAPPα levels i.e. 39%, 41%, 46% and 66% when tested at doses 0.3, 1.0, 3.0, and 10.0 mg/kg, s.c. respectively. The positive control, 5-HT$_4$ receptor agonist, prucalopride significantly increased the level of sAPPα in adult mice cortex at 10.0 mg/kg s.c. (These results are in line with results of reported literature, reference: British Journal of Pharmacology, 2007, 150; 883-892).
Other References: Journal of Pharmacology and Experimental Therapeutics, 2003, 305, 864-871; Current Pharmaceutical Design 2006, 12, 671-676 and Journal of Pharmacology and Experimental Therapeutics 2006, 317, 786-790.
Result for Example 23 (FIG. 2)

At 60 minutes post treatment, the compound of Example 23 showed significant increase in the mice brain cortical sAPPα levels i.e. 42% and 33% at 0.3 and 1.0 mg/kg, s.c. dose respectively. The positive control, 5-HT$_4$ receptor agonist, prucalopride significantly increased the level of sAPPα in adult mice cortex at 10.0 mg/kg s.c. (These results are in line with results of reported literature, reference: British Journal of Pharmacology, 2007, 150, 883-892).

Example 67

To Evaluate the Effect of Compounds of Present Invention on Modulation of Acetylcholine from the Ventral Hippocampus of Male Wistar Rats Experimental Procedure:

Male Wistar rats (240-300 gram body weights) were stereotaxically implanted with a microdialysis guide cannula in the ventral hippocampus (AP: −5.2 mm, ML: +5.0 mm, DV: −3.8 mm). Co-ordinates were taken according to Paxinos and Watson (2007) with reference points taken from bregma and vertical from the skull. The rats were allowed to recover individually for five days in a round bottom Plexiglas bowl with free access to feed and water.

One day prior to the microdialysis experiment, rats were connected to a dual quartz lined two-channel liquid swivel (Instech, UK) on a counter balance lever arm, which allowed unrestricted movements of the animal. Sixteen hour before start of the study, a pre-equilibrated microdialysis probe (4 mm dialysis membrane) was inserted into the ventral hippocampus through the guide cannula.

On the day of study, probe was perfused at a constant flow rate of 1.5 min with artificial cerebrospinal fluid (aCSF; NaCl 147 mM, KCl 3.0 mM, MgCl$_2$ 1.0 mM, CaCl$_2$. 2H$_2$O 1.3 mM, NaH$_2$PO4.2H$_2$O 0.2 mM and Na$_2$HPO$_4$. 7H$_2$O 1.0 mM, pH 7.2). A stabilization period of 2 h was maintained and five basal samples were collected at 20 min intervals. Compound or vehicle was administered and dialysate samples were collected at 20 min interval for an additional period of 4 h. Dialysates were stored below −70° C. until quantitation of acetylcholine.
Quantitation of Acetylcholine:

Acetylcholine in dialysate was quantified in the calibration range of 0.103 nmol-103.497 nmol using LC-MS/MS method.
Statistical Analysis:

All microdialysis data were plotted as percent change from mean dialysate basal concentrations with 100% defined as the average of five predose values. The AUC was calculated by trapezoidal rule using WinNonlin (5.0.1 version. Pharsight Corp. CA). The statistical significance between the mean AUC values of treatment groups with vehicle was calculated using one-way ANOVA followed by Dunnett's test. For each treatment group, the percent increase in acetylcholine levels was compared to the vehicle group using two-way analysis of variance (time and treatment), followed by Bonferroni's multiple comparison test. Statistical significance was considered at a p value less than 0.05.

Figure 3:
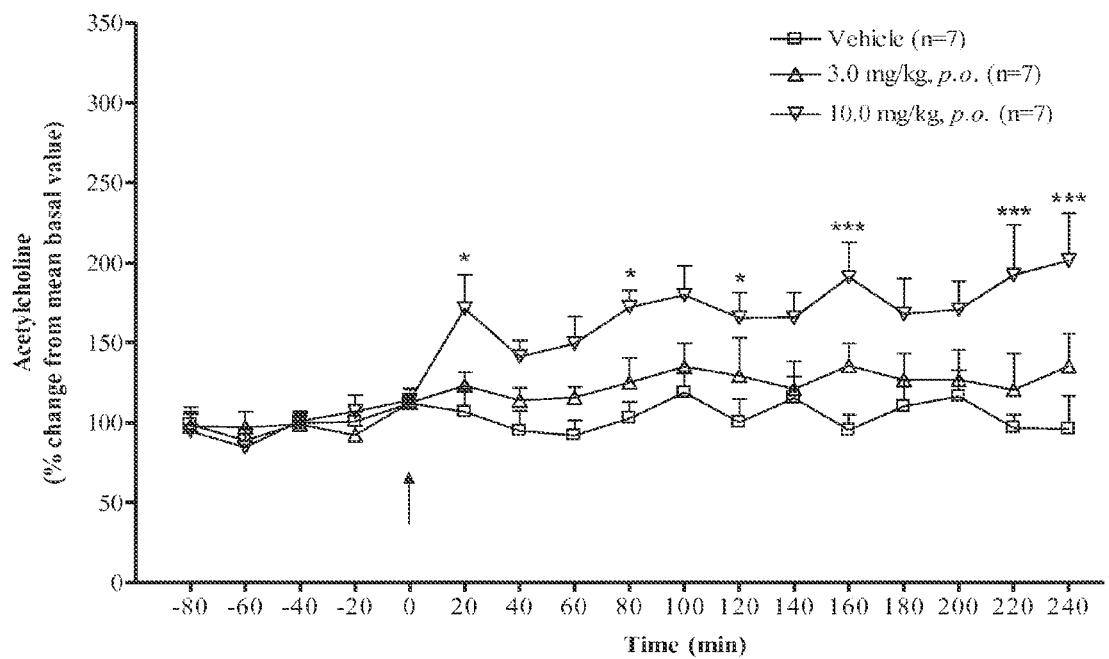
Figure 4:
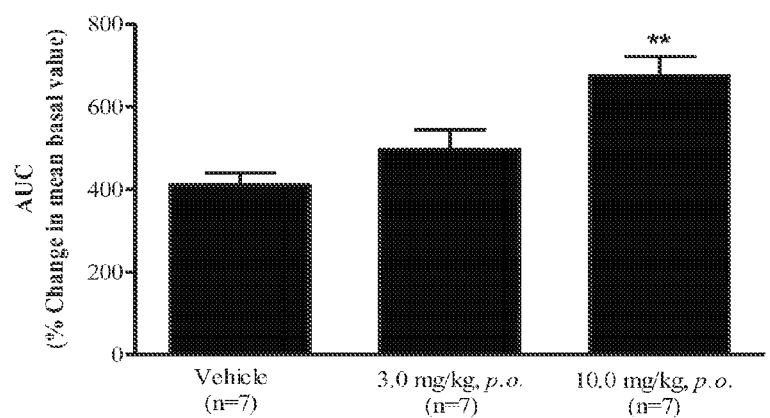

Incorrect probe placement was considered as criteria to reject the data from animal.
References: Neuropharmacology, 2007, 53, 563-573; Paxinos G and Watson C (2007) Rat brain in stereotaxic coordinates. Academic Press, New York.
Result of Example 13 (FIGS. 3 and 4):

The compound of Example 13 produced dose dependent increase in acetylcholine levels from the ventral hippocampus of male Wistar rats (FIG. 3, Effect of compound of Example 13 (3.0 and 10.0 mg/kg, p.o.) on acetylcholine levels in ventral hippocampus of male Wistar rats. Values are expressed as mean±SEM. *p<0.05, ***p<0.001).

Area under the curve values calculated to evaluate the overall effect of treatment was significant after treatment with compound of Example 13 (10.0 mg/kg, p.o.) (FIG. 4, Cumulative changes in acetylcholine levels expressed as mean area under the curve (AUC)±S.E.M. of % change from mean basal value for each treatment group. **p<0.01)

Example 68

To evaluate the effect of compounds of present invention on modulation of acetylcholine from the frontal cortex of male Wistar rats.

Experimental Procedure:

Male Wistar rats (240-300 gram body weights) were stereotaxically implanted with a microdialysis guide cannula in the frontal cortex (AP: +3.2 mm, ML: −3.2 mm, DV: −1.5 mm). Co-ordinates were taken according to Paxinos and Watson (2007) with reference points taken from bregma and vertical from the skull. The rats were allowed to recover individually for five days in a round bottom Plexiglas bowl with free access to feed and water.

One day prior to the microdialysis experiment, rats were connected to a dual quartz lined two-channel liquid swivel (Instech. UK) on a counter balance lever arm, which allowed unrestricted movements of the animal. Sixteen hour before start of the study, a pre-equilibrated microdialysis probe (3 mm dialysis membrane) was inserted into the frontal cortex through the guide cannula.

On the day of study, probe was perfused at a constant flow rate of 1.5 (μL/min with artificial cerebrospinal fluid (aCSF; NaCl 147 mM. KCl 3.0 mM, MgCl$_2$ 1.0 mM, CaCl$_2$. 2H$_2$O 1.3 mM, NaH$_2$PO4.2H$_2$O 0.2 mM and Na$_2$HPO$_4$. 7H$_2$O 1.0 mM, pH 7.2). A stabilization period of 2 h was maintained and five basal samples were collected at 20 minutes intervals. The compound of Example 18 or vehicle was administered and dialysate samples were collected at 20 minutes interval for an additional period of 4 hours. Dialysates were stored below −70° C. until quantitation of acetylcholine.
Quantitation of Acetylcholine:

Acetylcholine in dialysate was quantified in the calibration range of 0.103 nmol-103.497 nmol using LC-MS/MS method.
Statistical Analysis:

All microdialysis data were plotted as percent change from mean dialysate basal concentrations with 100% defined as the average of five predose values. The AUC was calculated by trapezoidal rule using WinNonlin (5.0.1 version, Pharsight Corp. CA). The statistical significance between the mean AUC values of treatment groups with vehicle was calculated using one-way ANOVA followed by Dunnett's test. For each treatment group, the percent increase in acetylcholine levels was compared to the vehicle group using two-way analysis of variance (time and treatment), followed by Bonferroni's multiple comparison test. Statistical significance was considered at ap value less than 0.05.

Incorrect probe placement was considered as criteria to reject the data from animal.

Figure 5:
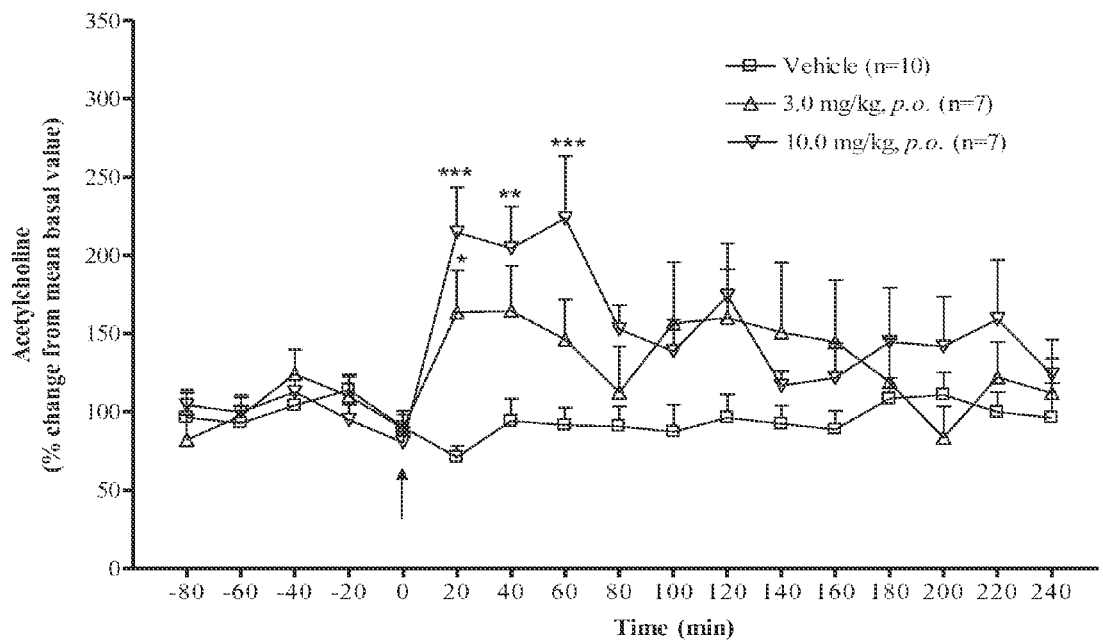
Figure 6:
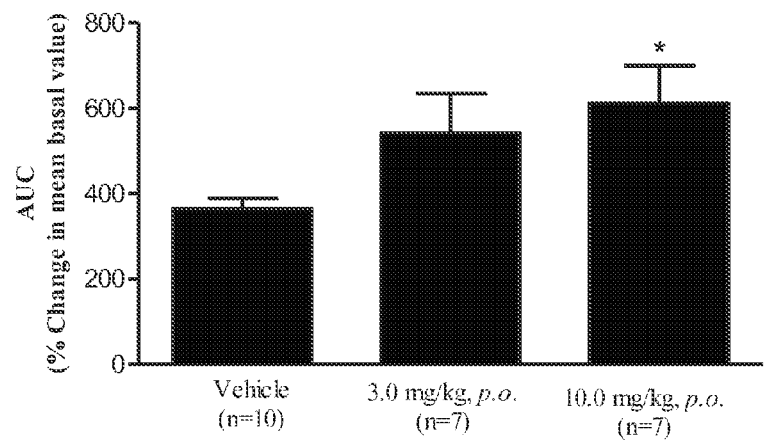

References: Current Drug Targets—CNS & Neurological Disorders, 2004, 3, 39-51; Paxinos G and Watson C (2007) Rat brain in stereotaxic coordinates. Academic Press, New York Result of Example 13 (FIGS. 5 and 6):

The compound of Example 13 produced dose dependent increase in acetylcholine levels from the frontal cortex of male Wistar rats (FIG. 5, effect of compound of Example 13 (3.0 and 10.0 mg/kg, p.o.) on acetylcholine levels in the frontal cortex of male Wistar rats. Values are expressed as mean±SEM. *p<0.05, p<0.01, *p<0.001).

Area under the curve values calculated to evaluate the overall effect of treatment was significant after treatment with compound of Example 13 (10.0 mg/kg, p.o.) (FIG. 6, cumulative changes in acetylcholine levels expressed as mean area under the curve (AUC)±S.E.M. of % change from mean basal value for each treatment group. *p<0.05).

Example 69

To Evaluate the Effect of Compounds of Present Invention on CSF $A\beta_{1-40}$ Level in Male Sprague Dawley Rat Experimental Procedure:

The control group of male rats received a vehicle (reagent grade water) per orally by gavage at a dose volume of 10 mL/kg. The treated groups (6 rat per group) received a single dose of test compound (different doses) or DAPT (50.0 mg/kg). Two hour post dose of vehicle or test compounds, rats were anesthetized with isoflurane and CSF was collected from Cisterna magna using 0.5 mL syringes by utilizing stereotaxic frame. The CSF samples were frozen in liquid nitrogen and stored at −80° C. until ELISA was performed.

Sample Preparation:
1. CSF samples were thawed to RT and diluted with Tris Buffer Saline containing protease inhibitors at 1:10 ratio 115:150 μL (15 μL CSI+135 μL TBS.
2. To this diluted CSF samples 0.15 mL of EIA buffer (1:1 ratio) was added. These diluted samples were subjected for $A\beta_{1-40}$ level measurement by ELISA.

Measurement of $A\beta_{1-40}$ by ELISA Kit:

To investigate the role of an acute treatment of test compound on $A\beta_{1-40}$ levels, expression of this protein in CSF was measured in treated and untreated rat by ELISA assay. The entire procedure was followed as per ELISA kit manual (Mouse/Rat Amyloid-$A\beta_{1-40}$ ELISA, Cat No: 27721, IBL International, Hamburg, Germany).

Statistical Analysis:

Statistical analysis was performed using the Graph Pad Prism (Version 4). Data are Mean±SD of $A\beta_{1-40}$ levels expressed as percentage of control values (rat which received regent grade water). Values were compared between the different groups by using unpaired t test. The significance level was set at *p<0.05; p<0.01; *p<0.001.

References: Current Pharmaceutical Design 12, 671-676, 2006; Journal of Pharmacology and Experimental Therapeutics, 305, 864-871, 2003 and Journal of Pharmacology and Experimental Therapeutics, 317, 786-790, 2006.

Figure 7:
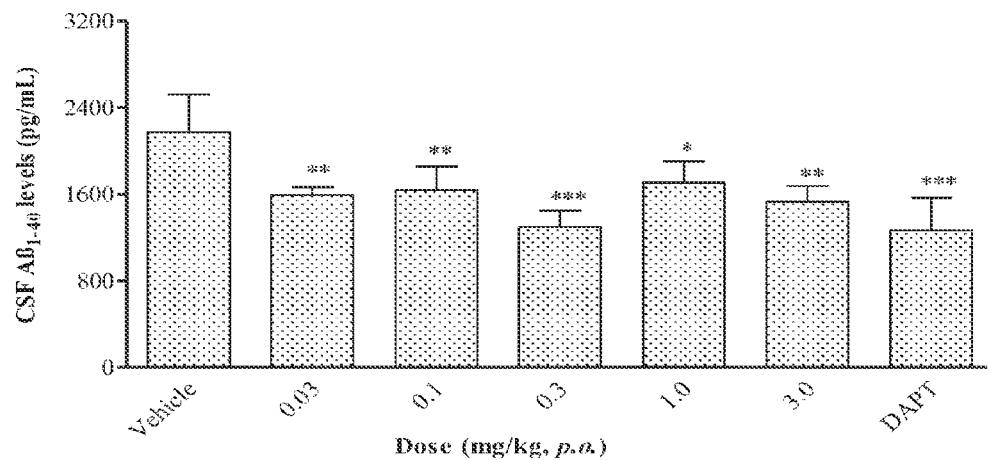
Figure 8:
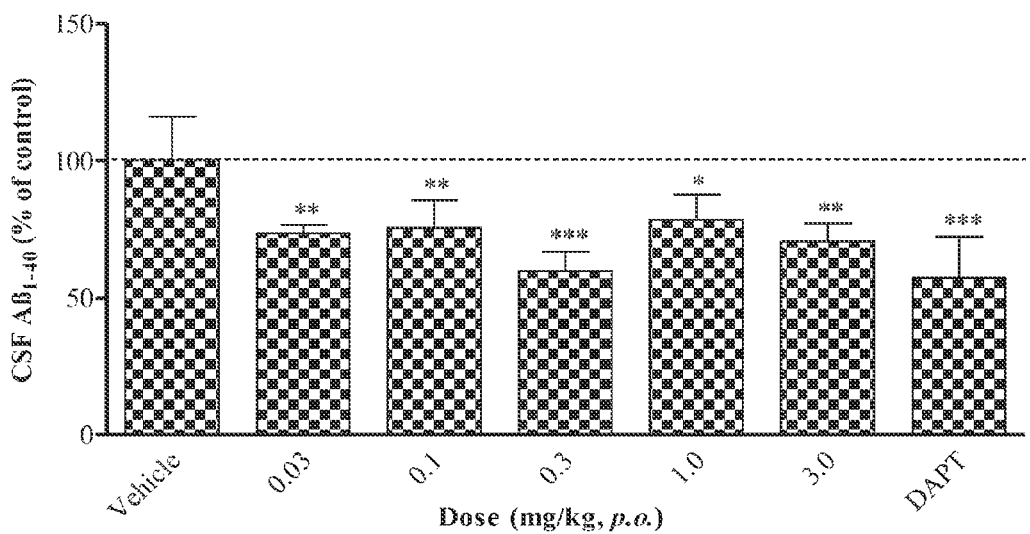

Results for Example 1 (FIGS. 7 and 8)

The compound of Example 1 shown significant decrease in the rat CSF $A\beta_{1-40}$ levels at two hour i.e. 27, 24, 40, 22, and 29% when tested at doses 0.03, 0.1, 0.3, 1.0, and 3.0 mg/kg, p.o. respectively.

The positive control DAPT significantly decreased the level of $A\beta_{1-40}$ in rat CSF at 50.0 mg/kg p.o. (In line with literature).

Example 70

To Evaluate the Effect of Compounds of Present Invention on CSF $A\beta_{1-42}$ Level in Male Sprague Dawley Rat Experimental Procedure:

The control group of male rats received a vehicle (reagent grade water) per orally by gavage at a dose volume of 10 mL/kg. The treated groups (6 rat per group) received a single dose of test compound (different doses) or DAPT (50.0 mg/kg). Two hour post dose of vehicle or test compounds, rats were anesthetized with isoflurane and CSF was collected by puncturing Cisterna magna using 0.5 mL syringes by utilizing stereotaxic frame. CSF samples were frozen in liquid nitrogen and stored at −80° C. until ELISA was performed.

Sample Preparation:
1. CSF samples were thawed to RT and diluted with Tris Buffer Saline containing protease inhibitors at 1:10 ratio [15:150 μL (15 μL CSF+ 135 μL TBS],
2. To this diluted CSF samples 0.15 mL of EIA buffer (1:1 ratio) was added. These diluted samples were subjected for $A\beta_{1-42}$ level measurement by ELISA.

Measurement of $A\beta_{1-42}$ by ELISA Kit:

To investigate the role of an acute treatment of test compound on $A\beta_{1-42}$ levels, expression of this protein was measured in CSF of treated and untreated rat by ELISA assay. The entire procedure was followed as described in ELISA kit manual (Mouse/Rat Amyloid-$\beta_{1-40}$ ELISA, Cat No: 27720, IBL International, Hamburg, Germany).

Statistical Analysis:

Statistical analyses were performed using the Graph Pad Prism (Version 4). Data are Mean±SD of $A\beta_{1-42}$ levels expressed as percentage of control values (rat which received regent grade water). Values were compared between the different groups by unpaired t test. The significance level was set at *p<0.05; p<0.01; *p<0.001.

References: Current Pharmaceutical Design 12, 671-676, 2006; Journal of Pharmacology and Experimental Therapeutics, 305, 864-871, 2003 and Journal of Pharmacology and Experimental Therapeutics, 317, 786-790, 2006.

Figure 9:
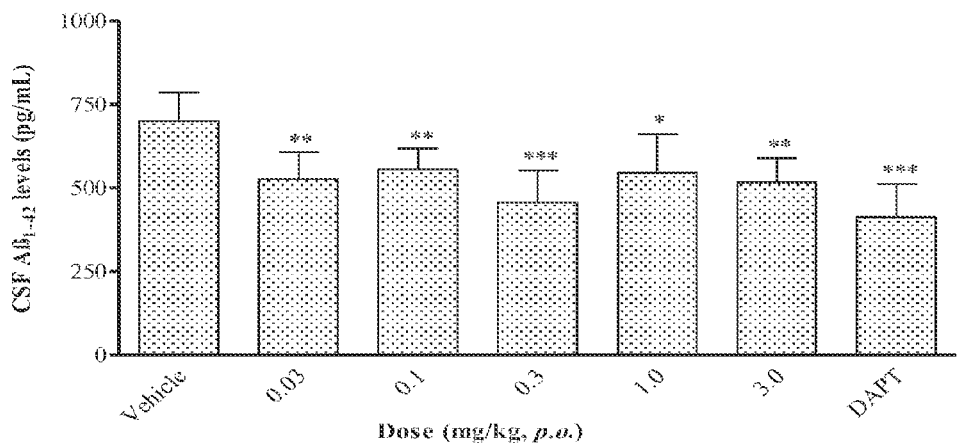
Figure 10:
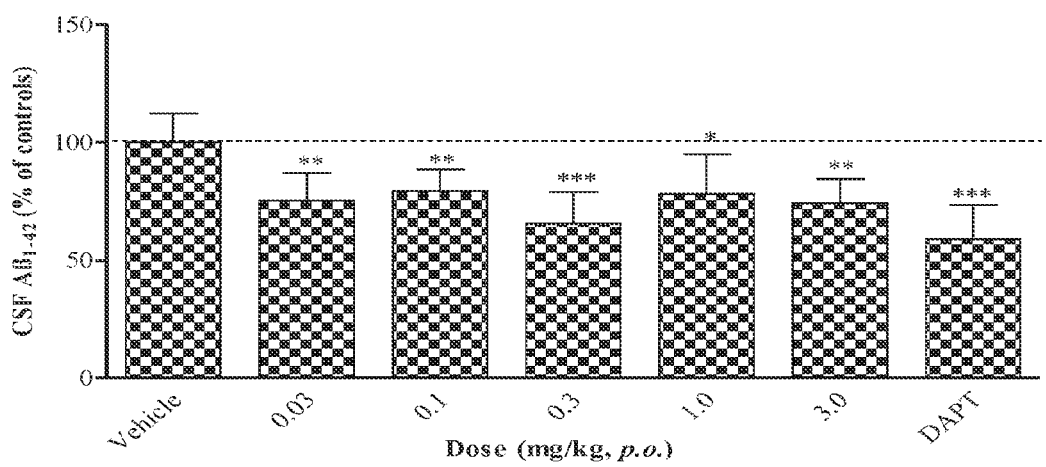

Results for Example 1 (FIGS. 9 and 10)

At two hour post treatment, the compound of Example 1 showed significant decrease in the rat CSF $A\beta_{1-42}$ levels i.e. 25, 21, 35, 22, and 26% when tested at doses 0.03, 0.1, 0.3, 1.0, and 3.0 mg/kg, p.o. dose respectively.

The positive control DAPT significantly decreased the levels of $A\beta_{1-42}$ in rat CSF at 50.0 mg/kg p.o. (In line with the literature).

Example 71

Object Recognition Task Model

The cognition enhancing properties of compounds of this invention were estimated by using this model.

Male Wistar rats (230-280 grams) were used as experimental animals. Four animals were housed in each cage. Animals were kept on 20% food deprivation before one day and given water ad libitum throughout the experiment and maintained on a 12 hours light/dark cycle. Also the rats were habituated to individual arenas for 1 hour in the absence of any objects.

One group of 12 rats received vehicle (1 mL/Kg) orally and another set of animals received compound of the formula (I) either orally or i.p., before one hour of the familiar (T1) and choice trial (T2).

The experiment was carried out in a 50×50×50 cm open field made up of acrylic. In the familiarization phase, (T1), the rats were placed individually in the open field for 3 minutes, in which two identical objects (plastic bottles, 12.5 cm height×5.5 cm diameter) covered in yellow masking tape alone (a1 and a2) were positioned in two adjacent corners, 10 cms from the walls. After 24 hours of the (T1) trial for long-term memory test, the same rats were placed in the same arena as they were placed in T1 trial. Choice phase (T2) rats were allowed to explore the open field for 3 minutes in presence of one familiar object (a3) and one novel object (b) (Amber color glass bottle, 12 cm high and 5 cm in diameter). Familiar objects presented similar textures, colors and sizes. During the T1 and T2 trial, explorations of each object (defined as sniffing, licking, chewing or having moving vibrissae whilst directing the nose towards the object at a distance of less than 1 cm) were recorded separately by stopwatch. Sitting on an object was not regarded as exploratory activity, however, it was rarely observed.

T1 is the total time spent exploring the familiar objects (a1+a2).

T2 is the total time spent exploring the familiar object and novel object (a3+b).

The object recognition test was performed as described by Behaviour Brain Research, (1988), 31, 47-59.

| Example Number | Dose mg/kg, p.o. | Exploration time mean ± S.E.M (sec) | | Inference |
| | | Familiar object | Novel object | |
|---|---|---|---|---|
| 1. | 0.1 mg/kg, p.o. | 5.94 ± 0.71 | 16.09 ± 1.75 | Active |
| 2. | 0.03 mg/kg, p.o. | 7.46 ± 1.30 | 15.75 ± 1.65 | Active |
| 4. | 0.03 mg/kg, p.o. | 6.96 ± 1.02 | 12.37 ± 1.22 | Active |
| 13. | 1 mg/kg, p.o. | 8.64 ± 1.33 | 15.11 ± 1.81 | Active |
| 23. | 0.01 mg/kg, p.o. | 8.80 ± 1.46 | 16.80 ± 2.45 | Active |
| 37. | 10 mg/kg, p.o. | 8.45 ± 1.65 | 17.81 ± 1.42 | Active |
| 43. | 0.3 mg/kg, p.o. | 9.30 ± 0.93 | 16.09 ± 2.63 | Active |

Example 72

Radial Arm Maze

The cognition enhancing properties of compounds of formula (I) of this invention were estimated by using this model.

Radial arm maze consists of a central hub of 45 cm diameter. Each arm was of dimension 42.5×15×24 cm. The maze was elevated to a height of 1 m above the ground. The animals were placed on a restricted diet until they reached approximately 85% of their free feeding weight. During this diet restriction period animals were habituated to the novel feed (pellets). Once the rats reached approximately 85% of their free feeding weight rats were habituated to the maze on the $1^{st}$ and $2^{nd}$ day. The animals that did not eat the pellets were rejected from the study. Animals were randomized on day 2. On the subsequent days the treatment was given as per the allotment: Each animal was introduced into the maze individually for a period of 10 minutes. The arms were baited only once and the animal had to learn the rule that repeated arm entries would not be rewarded. The trial ended once the rat had visited 16 arms or 10 minutes were over or all the pellets were eaten. The arm entries were recorded using the software. Once the trial was over the rat was removed and the maze was cleaned using soap water.

| Example Number | Reversal of Scopolamine Induced amnesia - Effective dose range |
|---|---|
| 13. | 0.1-1 mg/kg, p.o. |
| 23. | 0.01-0.1 mg/kg, p.o. |

We claim:
1. A compound of the general formula (I):

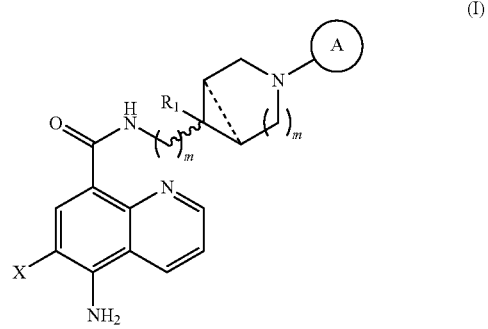

or a pharmaceutically acceptable salt thereof,
wherein,
"X" is halogen;
"⁓" is a bond represents racemic mixture, R-enantiomer, S-enantiomer, exo isomer, endo isomer or achiral;

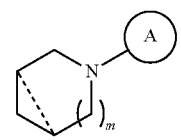

is

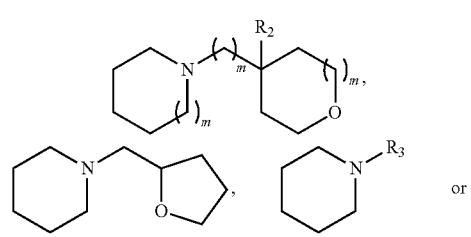

-continued

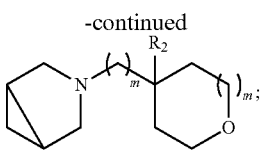

$R_1$ is hydrogen, hydroxy or fluoro;
$R_2$ is hydrogen, hydroxy or fluoro;
$R_3$ is

$R_5$ is fluoro, hydroxy or methoxy;
m is 0 or 1, both inclusive.

2. A compound selected from:
(a) a compound of formula (Ia):

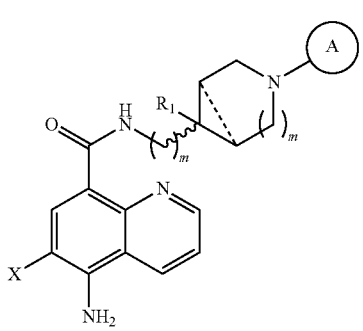

or a pharmaceutically acceptable salt thereof,
wherein,
"X" is halogen;
"⁓" is a bond represents a racemic mixture, R-enantiomer, S-enantiomer, exo isomer, endo isomer or achiral;

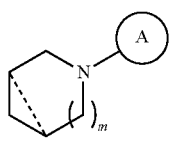

is

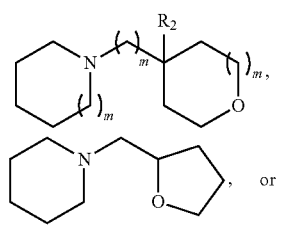

-continued

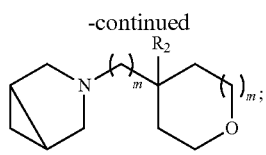

$R_1$ is hydrogen, hydroxy or fluoro;
"m" is 0 or 1, both inclusive;
$R_2$ is hydroxy or fluoro;
$R_3$ is

and
$R_5$ is fluoro, hydroxy or methoxy;
(b) a compound of formula (Ib-1):

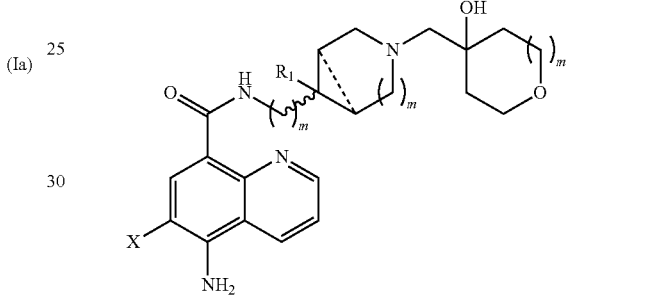

or a pharmaceutically acceptable salt thereof,
wherein,
"X" is halogen;
"⁓" is a bond which represents a racemic mixture, R-enantiomer, S-enantiomer, exo isomer, endo isomer or achiral;
$R_1$ is hydrogen, hydroxy or fluoro;
"m" is 0 or 1, both inclusive; and
"------" represents a bond or no bond;
(c) a compound of formula (Ib-2):

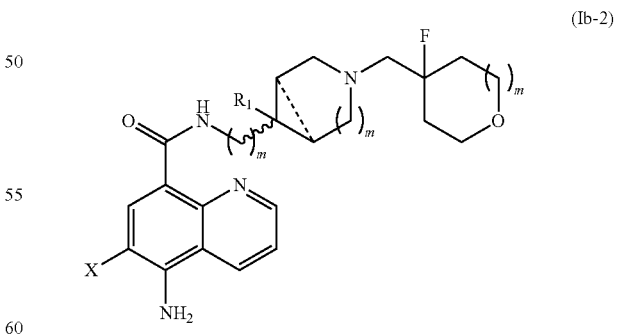

or a pharmaceutically acceptable salt thereof,
wherein,
"X" is halogen;
"⁓" is a bond which represents a racemic mixture, R-enantiomer, S-enantiomer, exo isomer, endo isomer or achiral;

$R_1$ is hydrogen, hydroxy or fluoro;
"m" is 0 or 1, both inclusive; and
"-------" represents a bond or no bond;
(d) compound of formula (Id-1):

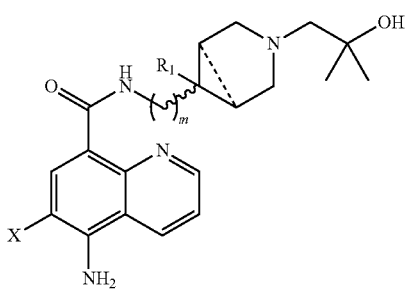

(Id-1)

or a pharmaceutically acceptable salt thereof,
wherein,
"X" is halogen;
"⁓" is a bond which represents a racemic mixture, R-enantiomer, S-enantiomer, exo isomer, endo isomer or achiral;
$R_1$ is hydrogen, hydroxy or fluoro;
"m" is 0 or 1, both inclusive; and
"-------" represents a bond or no bond;
(e) a compound of formula (Id-2):

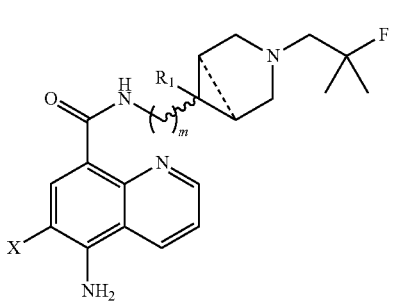

(Id-2)

or a pharmaceutically acceptable salt thereof,
wherein,
"X" is halogen;
"⁓" is a bond which represents a racemic mixture, R-enantiomer, S-enantiomer, exo isomer, endo isomer or achiral;
$R_1$ is hydrogen, hydroxy or fluoro;
"m" is 0 or 1, both inclusive; and
"-------" represents a bond or no bond.

3. The compound according to claim 1, which is selected from the group consisting of:

5-amino-6-chloro-N-{[1-(tetrahydro-2H-pyran-4-ylmethyl)-4-piperidinyl]methyl}quinoline-8-carboxamide hemifumarate;
5-amino-6-chloro-N-{[3-tetrahydro-2H-pyran-4-ylmethyl)-3-azabicyclo[3.1.0]hex-6-yl]methyl}quinoline-8-carboxamide L(+)-tartarate;
5-Amino-6-chloro-N-[1-(tetrahydro-2H-pyran-4-ylmethyl)] quinoline-8-carboxamide;
(R,S) 5-Amino-6-chloro-N-{[1-(tetrahydro-3-furanylmethyl)-4-piperidinyl]methyl}quinoline-8-carboximide L(+)-tartarate;
(R,S) 5-Amino-6-chloro-N-{[1-(tetrahydro-2-furanylmethyl)-4-piperidinyl]methyl}quinoline-8-carboxamide;
5-Amino-6-chloro-N-{[1-(tetrahydro-2H-pyran-4-yl)-4-piperidinyl]methyl}quinoline-8-carboxamide L(+)-tartarate;
5-Amino-6-chloro-N-{[3-(tetrahydro-3-furanylmethyl-3-azabicyclo[3.1.0]hex-6-yl]methyl}quinoline-8-carboxamide;
5-Amino-6-fluoro-N-{[1-(tetrahydro-2H-pyran-4-ylmethyl)-4-piperidinyl]methyl}quinoline-8-carboxamide L(+)-tartarate;
5-Amino-6-chloro-N-{[1-(tetrahydro-2H-pyran-4-ylmethyl)-3-pyrrolidinyl]methyl}quinoline-8-carboxamide L(+)-tartarate;
5-Amino-6-chloro-N-{[1-(tetrahydro-2H-pyran-4-ylmethyl)-4-piperidinyl]methyl}quinoline-8-carboxamide L(+)tartarate;
(Exo)5-Amino-6-chloro-N-{[3-(tetrahydro-2H-pyran-4-ylmethyl)-3-azabicyclo[3.1.0]hex-6-yl]methyl}quinoline-8-carboxamide;
5-Amino-6-chloro-N-{[3-(tetrahydro-2H-pyran-4-ylmethyl)-3-azabicyclo[3.1.0]hex-6-yl]methyl}quinoline-8-carboxamide;
5-Amino-6-bromo-N{[1-(tetrahydro-2H-pyran-4-ylmethyl)-4-piperidinyl]methyl}quinoline-8-carboxamide L(>)-tartarate;
5-Amino-6-bromo-N-{[3-(tetrahydro-2H-pyran-4-ylmethyl)-3-azabicyclo[3.1.0]hex-6-yl]methyl}quinoline-8-carboxamide L(+)-tartarate;
5-Amino-6-chloro-N-{[1-(tetrahydro-2-furanylmethyl)-4-piperidinyl]methyl}quinoline-8-carboxamide L(+)-tartarate;
5-Amino-6-fluoro-N-{[3-(tetrahydro-2H-pyran-4-yl methyl)-3-azabicyclo[3.1.0]hex-6-yl] methyl}quinoline-carboxamide L(+)-tartarate;
5-Amino-6-chloro-N-{[4-fluoro-1-(tetrahydro-2H-pyran-4-ylmethyl)-4-piperidinyl]methyl}quinoline-8-carboxamide L(+)-tartarate;
(R,S)5-Amino-6-chloro-N-{[4-fluoro-1-(tetrahydro-3-furanylmethyl)-4-piperidinyl]methyl}quinoline-8-carboxamide L(+)-tartarate;
5-Amino-6-chloro-N-{[4-hydroxy-1-(tetrahydro-2H-pyran-4-yl methyl)-4-piperidinyl]methyl}quinoline-8-carboxamide L(+)-tartarate;
5-Amino-6-chloro-N-{[1-(4-hydroxytetrahydro-2H-pyran-4-ylmethyl)-4-piperidinyl]methyl}quinoline-8-carboxamide L(+)tartarate;
5-Amino-6-chloro-N-[1-(4-hydroxytetrahydro-2H-pyran-4-ylmethyl)-4-piperidinyl] quinoline-8-carboxyamide;
5-Amino-6-chloro-N-{[1-(4-hydroxytetrahydro-2H-pyran-4-ylmethyl)-3-azabicyclo[3.1.0]hex-6-yl] methyl}quinoline-8-carboxamide L(+)-tartarate;
5-Amino-6-chloro-N-{[1-(4-hydroxytetrahydro-2H-pyran-4-ylmethyl)-4-piperidinyl]methyl}quinoline-8-carboxyamide;
5-Amino-6-Chloro-N-{[4-fluoro-1-(4-hydroxytetrahydro-2H-pyran-4-ylmethyl)-4-piperidinyl] methyl}quinoline-8-carboxamide L(+)-tartarate;
5-Amino-6-fluoro-N-{1-(1-(4-hydroxytetrahydro-2H-pyran-4-ylmethyl)-4-piperidinyl]methyl}quinoline-8-carboxamide L(+)-tartarate;
5-Amino-6-chloro-N-{[4-hydroxy-1-(4-hydroxy tetrahydro-2H-pyran-4-yl methyl)-4-piperidinyl] methyl}quinoline-8-carboxamide L(+)-tartarate;
5-Amino-6-chloro-N-{[1-(4-fluorotetrahydro-2H-pyran-4-ylmethyl)-4-piperidinyl]methyl}quinoline-8-carboxamide L(+)-tartarate;

5-Amino-6-chloro-N-{[1-(2-hydroxy-2-methyl propyl)-4-piperidinyl]methyl}quinoline-8-carboxamide L(+)-tartarate;
5-Amino-6-chloro-N-{[4-fluoro-1-(2-hydroxy-2-methyl propyl)-4-piperidinyl]methyl}quinoline-8-carboxamide;
5-Amino-6-chloro-N-{[4-fluoro-1-(2-hydroxy-2-methyl propyl)-4-piperidinyl]methyl}quinoline-8-carboxamide L(+)-tartarate;
5-Amino-6-chloro-N-{[4-fluoro-1-(2-hydroxy-2-methyl propyl)-4-piperidinyl]methyl}quinoline-8-carboxamide hydrochloride;
5-Amino-6-chloro-N-{[4-fluoro-1-(2-hydroxy-2-methyl propyl)-4-piperidinyl]methyl}quinoline-8-carboxamide fumarate;
5-Amino-6-chloro-N-{[3-(2-hydroxy-2-methyl propyl)-3-azabicyclo[3.1.0]hex-6-yl]methyl}quinoline-8-carboxamide L(+)-tartarate;
5-Amino-6-fluoro-N-{[1-(2-hydroxy-2-methyl propyl)-4-piperidinyl]methyl}quinoline-8-carboxamide L(+)-tartarate;
5-Amino-6-fluoro-N-{[4-fluoro-1-(2-hydroxy-2-methyl propyl)-4-piperidinyl]methyl}quinoline-8-carboxamide;
5-Amino-6-fluoro-N-{[4-fluoro-1-(2-hydroxy-2-methyl propyl)-4-piperidinyl]methyl}quinoline-8-carboxamide L(+)-tartarate;
5-Amino-6-bromo-N-{[1-(2-hydroxy-2-methyl propyl)-4-piperidinyl]methyl}quinoline-8-carboxamide L(+)-tartarate;
5-Amino-6-bromo-N-{[4-fluoro-1-(2-hydroxy-2-methyl propyl)-4-piperidinyl]methyl}quinoline-8-carboxamide L(+)-tartarate;
5-Amino-6-chloro-N-{[1-(4-fluoro-2-methyl propyl)-4-piperidinyl]methyl}quinoline-8-carboxamide;
5-Amino-6-chloro-N-{[3-(2-fluoro-2-methyl propyl)-3-azabicyclo[3.1.0]hex-6-yl]methyl}quinoline-8-carboxamide;
5-Amino-6-chloro-N-{[4-fluoro-1-(2-fluoro-2-methyl propyl)-4-piperidinyl]methyl}quinoline-8-carboxamide;
5-Amino-6-chloro-N-{[1-(2-methoxy-2-methyl propyl)-4-piperidinyl]methyl}quinoline-8-carboxamide;
5-Amino-6-fluoro-N-{[1-(2-methoxy-2-methyl propyl)-4-piperidinyl]methyl}quinoline-8-carboxamide;
5-Amino-6-bromo-N-{[1-(2-methoxy-2-methyl propyl)-4-piperidinyl]methyl}quinoline-8-carboxamide;
5-Amino-6-chloro-N-{[4-fluoro-1-(2-methoxy-2-methyl propyl)-4-piperidinyl]methyl}quinoline-8-carboxamide;
5-Amino-6-fluoro-N-{[4-fluoro-1-(2-methoxy-2-methyl propyl)-4-piperidinyl]methyl}quinoline-8-carboxamide; and
5-Amino-6-bromo-N-{[4-fluoro-1-(2-methoxy-2-methyl propyl)-4-piperidinyl]methyl}quinoline-8-carboxamide.

4. The compound according to claim 1, which is selected from the group consisting of:
5-Amino-6-chloro-N-{[1-(tetrahydro-2H-pyran-4-ylmethyl)-4-piperidinyl]methyl}quinoline-8-carboxamide hemifumarate;
5-Amino-6-chloro-N-{[3-(tetrahydro-2H-pyran-4-ylmethyl)-3-azabicyclo[3.1.0]hex-6-yl]methyl}quinoline-8-carboxamide L(+)-tartarate;
5-Amino-6-chloro-N-[1-(tetrahydro-2H-pyran-4-ylmethyl)-4-piperidinyl] quinoline-8-carboxamide;
(R,S) 5-Amino-6-chloro-N-{[1-(tetrahydro-3-furanylmethyl)-4-piperidinyl]methyl}quinoline-8-carboxamide L(+)-tartarate;
(R,S) 5-Amino-6-chloro-N-{[1-(tetrahydro-2-furanylmethyl)-4-piperidinyl]methyl}quinoline-8-carboxamide;
5-Amino-6-chloro-N-{[1-(tetrahydro-2H-pyran-4-yl)-4-piperidinyl]methyl}quinoline-8-carboxamide L(+)-tartarate;
5-Amino-6-chloro-N-{[3-(tetrahydro-3-furanylmethyl)-3-azabicyclo[3.1.0]hex-6-yl]methyl}quinoline-8-carboxamide;
5-Amino-6-fluoro-N-{[1-(tetrahydro-2H-pyran-4-ylmethyl)-4-piperidinyl]methyl}quinoline-8-carboxamide L(+)-tartarate;
5-Amino-6-chloro-N-{[1-(tetrahydro-2H-pyran-4-ylmethyl)-3-pyrrolidinyl]methyl}quinoline-8-carboxamide L(+)-tartarate;
5-Amino-6-chloro-N-{[1-(tetrahydro-2H-pyran-4-ylmethyl)-4-piperidinyl]methyl}quinoline-8-carboxamide L(+)-tartarate;
(Exo) 5-Amino-6-chloro-N-{[3-(tetrahydro-2H-pyran-4-ylmethyl)-3-azabicyclo[3.1.0]hex-6-yl]methyl}quinoline-8-carboxamide;
5-Amino-6-chloro-N-{[3-(tetrahydro-2H-pyran-4-ylmethyl)-3-azabicyclo[3.1.0]hex-6-yl]methyl}quinoline-8-carboxamide;
5-Amino-6-bromo-N-{[1-(tetrahydro-2H-pyran-4-ylmethyl)-4-piperidinyl]methyl}quinoline-8-carboxamide L(+)-tartarate;
5-Amino-6-bromo-N-{[3-(tetrahydro-2H-pyran-4-yl methyl)-3-azabicyclo[3.1.0]hex-6-yl]methyl}quinoline-B-carboxamide L(+)-tartarate;
5-Amino-6-chloro-N-{[1-(tetrahydro-2-furanylmethyl)-4-piperidinyl]methyl}quinoline-8-carboxamide L(+) tartarate;
5-Amino-6-fluoro-N-{[3-(tetrahydro-2H-pyran-4-yl methyl)-3-azabicyclo[3.1.0]hex-6-yl]methyl}quinoline-8-carboxamide L(+)-tartarate;
5-Amino-6-chloro-N-{[4-fluoro-1-(tetrahydro-2H-pyran-4-ylmethyl)-4-piperidin]methyl}quinoline-8-carboxamide L(+)-tartarate;
(R,S) 5-Amino-6-chloro-N-{[4-fluoro-1-(tetrahydro-3-furanylmethyl)-4-piperidinyl]methyl}quinoline-8-carboxamide L(+)-tartarate;
5-Amino-6-chloro-N-{[4-hydroxy-1-(tetrahydro-2H-pyran-4-yl methyl)-4-piperidinyl]methyl} quinoline-8-carboxamide L(+)-tartarate;
5-Amino-6-chloro-N-{[1-(4-hydroxytetrahydro-2H-pyran-4-yl methyl)-4-piperidinyl]methyl}quinoline-8-carboxamide L(+)-tartarate;
5-Amino-6-chloro-N-[1-(4-hydroxytetrahydro-2H-pyran-4-ylmethyl)-4-piperidinyl]quinoline-8-carboxamide;
5-Amino-6-chloro-N-{[3-(4=hydroxytetrahydro-2H-pyran-4-ylmethyl)-3-azabicyclo[3.1.0]hex-6-yl]methyl}quinoline-8-carboxamide L(+)-tartarate;
5-Amino-6-chloro-N-{[1-(4-hydroxytetrahydro-2H-pyran-4-ylmethyl)-4-piperidinyl]methyl}quinoline-8-carboxamide;
5-Amino-6-chloro-N-{[1-(4-fluoro-1-(4-hydroxytetrahydro-2H-pyran-4-ylmethyl)-4-piperidinyl]methyl}quinoline-8-carboxamide L(+)tartarate;
5-Amino-6-fluoro-N-{1-(4-hydroxytetrahydro-2H-pyran-4-ylmethyl)-4-piperazinyl]methyl}quinoline-8-carboxamide L(+)-tartarate;
5-Amino-6-chloro-N-{[4-hydroxy-1-(4-hydroxy tetrahydro-2H-pyran-4-yl methyl)-4-piperidinyl]methyl}quinoline-8-carboxamide L(+)-tartarate;

5-Amino-6-chloro-N-{[1-(4-fluorotetrahydro-2H-pyran-4-ylmethyl)-4-piperidinyl]methyl}quinoline-8-carboxamide L(+)-tartarate;
5-Amino-6-chloro-N-{[1-(2-hydroxy-2-methyl propyl)-4-piperidinyl]methyl}quinoline-8-carboxamide L(+)-tartarate;
5-Amino-6-chloro-N-{[4-fluoro-1-(2-hydroxy-2-methyl propyl)-4-piperidinyl]methyl}quinoline-8-carboxamide;
5-Amino-6-chloro-N-{[4-fluoro-1-(2-hydroxy-2-methyl propyl)-4-piperidinyl]methyl}quinoline-8-carboxamide L(+)-tartarate;
5-Amino-6-chloro-N-{[4-fluoro-1-(2-hydroxy-2-methyl propyl)-4-piperidinyl]methyl}quinoline-8-carboxamide hydrochloride;
5-Amino-6-chloro-N-{[4-fluoro-1-(2-hydroxy-2-methyl propyl)-4-piperidinyl]methyl}quinoline-8-carboxamide fumarate;
5-Amino-6-chloro-N-{[3-(2-hydroxy-2-methyl propyl)-3-azabicyclo[3.1.0]hex-6-yl]methyl}quinoline-8-carboxamide L(+)-tartarate;
5-Amino-6-fluoro-N-{[1-(2-hydroxy-2-methyl propyl)-4-piperidinyl]methyl}quinoline-8-carboxamide L(+)-tartarate;
5-Amino-6-fluoro-N-{[4-fluoro-1-(2-hydroxy-2-methyl propyl)-4-piperidinyl]methyl}quinoline-8-carboxamide;
5-Amino-6-fluoro-N-{[4-fluoro-1-(2-hydroxy-2-methyl propyl)-4-piperidinyl]methyl}quinoline-8-carboxamide L(+)-tartarate;
5-Amino-6-bromo-N-{[1-(2-hydroxy-2-methyl propyl)-4-piperidinyl]methyl}quinoline-8-carboxamide L(+)-tartarate; and
5-Amino-6-bromo-N-{[4-fluoro-1-(2-hydroxy-2-methyl propyl)-4-piperidinyl]methyl}quinoline-8-carboxamide L(+)-tartarate.

5. A pharmaceutical composition comprising a compound according to claim 1 and a pharmaceutically acceptable excipient.

6. A pharmaceutical composition comprising a compound according to claim 2 and a pharmaceutically acceptable excipient.

7. A pharmaceutical composition comprising a compound according to claim 3 and a pharmaceutically acceptable excipient.

8. A pharmaceutical composition comprising a compound according to claim 4 and a pharmaceutically acceptable excipient.

9. A method of treating Alzheimer's disease, comprising administering to a patient in need thereof an effective amount of a compound of claim 1 or pharmaceutically acceptable salt thereof.

10. A method of treating Alzheimer's disease, comprising administering to a patient in need thereof an effective amount of a compound of claim 2 or pharmaceutically acceptable salt thereof.

11. A method of treating Alzheimer's disease, comprising administering to a patient in need thereof an effective amount of a compound of claim 3 or pharmaceutically acceptable salt thereof.

12. A method of treating Alzheimer's disease, comprising administering to a patient in need thereof an effective amount, of a compound of claim 4 or pharmaceutically acceptable salt thereof.

13. A method of treating schizophrenia comprising administering to a patient in need thereof an effective amount of a compound of claim 1 or pharmaceutically acceptable salt therof.

14. A method of treating constipation comprising administering to a patient in need thereof an effective amount of a compound of claim 1 or pharmaceutically acceptable salt thereof.

15. A method of treating schizophrenia comprising administering to a patient in need thereof an effective amount of a compound of claim 2 or pharmaceutically acceptable salt thereof.

16. A method of treating constipation comprising administering to a patient in need thereof an effective amount of a compound of claim 2 or pharmaceutically acceptable salt thereof.

17. A method of treating schizophrenia comprising administering to a patient in need thereof an effective amount of a compound of claim 3 or pharmaceutically acceptable salt thereof.

18. A method of treating constipation compirising administering to a patient in need thereof an effective amount of a compound of claim 3 or pharmaceutically acceptable salt thereof.

19. A method of treating schizophrenia comprising administering to a patient in need thereof an effective amount of a compound of claim 4 or pharmaceutically acceptable salt thereof.

20. A method of treating constipation comprising administering to a patient in need thereof an effective amount of a compound of claim 4 or pharmaceutically acceptable salt thereof.

* * * * *